United States Patent
Kobayashi et al.

(10) Patent No.: US 8,952,116 B2
(45) Date of Patent: Feb. 10, 2015

(54) PARTICULATE WATER ABSORBENT AND PROCESS FOR PRODUCTION THEREOF

(75) Inventors: Taishi Kobayashi, Hyogo (JP); Motohiro Imura, Hyogo (JP); Taku Iwamura, Hyogo (JP); Katsuyuki Wada, Hyogo (JP); Kozo Nogi, Hyogo (JP); Yoshiro Mitsukami, Hyogo (JP); Masato Abe, Hyogo (JP); Hiroko Ueda, Hyogo (JP); Koji Honda, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 13/498,780

(22) PCT Filed: Sep. 29, 2010

(86) PCT No.: PCT/JP2010/066957
§ 371 (c)(1),
(2), (4) Date: Mar. 28, 2012

(87) PCT Pub. No.: WO2011/040472
PCT Pub. Date: Apr. 7, 2011

(65) Prior Publication Data
US 2012/0184670 A1   Jul. 19, 2012

(30) Foreign Application Priority Data

Sep. 29, 2009  (JP) .................................. 2009-224756
Mar. 31, 2010  (JP) .................................. 2010-084530

(51) Int. Cl.
*C08F 220/06*       (2006.01)
*C08K 5/098*        (2006.01)
(Continued)

(52) U.S. Cl.
CPC ............... *C08F 220/06* (2013.01); *C08K 5/098* (2013.01); *B01J 20/223* (2013.01); *B01J 20/267* (2013.01);
(Continued)

(58) Field of Classification Search
CPC ......... C08F 220/06; C08K 5/098; C08L 33/02
USPC ........................................................ 526/317.1
See application file for complete search history.

(56) References Cited

U.S. PATENT DOCUMENTS 625,488 A   5/1899  Auspitz
632,352 A   9/1899  Jones
(Continued)

FOREIGN PATENT DOCUMENTS

CA   2 433 044 A1   7/2002
CA   2 403 966 A1   9/2002
(Continued)

OTHER PUBLICATIONS

Japanese International Search Report for PCT/JP2010/066957 dated Jan. 18, 2011 with English Translation.
(Continued)

*Primary Examiner* — Michael M Bernshteyn
(74) *Attorney, Agent, or Firm* — Harness, Dickey & Pierce, P.L.C.

(57) ABSTRACT

A particulate water absorbing agent of the present invention is a water absorbing agent containing a water absorbing resin as a main component, the particulate water absorbing agent containing a polyvalent metal cation and satisfying: (1) the polyvalent metal cation is contained in an amount between 0.001 wt % and 5 wt % relative to the amount of the water absorbing agent; (2) an absorbency without pressure (CRC) is not less than 28 (g/g) and an absorbency against pressure (AAP 4.83 kPa) is not less than 10 (g/g); (3) the absorbency against pressure and the absorbency without pressure satisfy $77 \leq AAP\,(4.83\,kPa) + 1.8 \times CRC \leq 100$; and (4) a moisture content of the water absorbing agent is between 5 wt % and 20 wt %. This provides a water absorbing agent which has blocking resistance after moisture absorption, is excellent in stability to shock and suppresses Re-Wet when used in a diaper.

10 Claims, 1 Drawing Sheet

(51) Int. Cl.

| | | |
|---|---|---|
| *C08L 33/02* | (2006.01) | |
| *B01J 20/22* | (2006.01) | |
| *B01J 20/26* | (2006.01) | |
| *B01J 20/30* | (2006.01) | |
| *A61L 15/60* | (2006.01) | |
| *C08J 3/24* | (2006.01) | |

(52) U.S. Cl.
CPC ............... *B01J 20/30* (2013.01); *A61L 15/60* (2013.01); *C08J 3/245* (2013.01); *C08J 2300/14* (2013.01); *B01J 2220/44* (2013.01); *C08J 2333/02* (2013.01)
USPC ........ 526/317.1; 524/556; 524/557; 524/503; 524/437

(56) References Cited

U.S. PATENT DOCUMENTS

| | | |
|---|---|---|
| 670,141 A | 3/1901 | Shepard |
| 922,717 A | 5/1909 | Parker |
| 955,086 A | 4/1910 | Laux |
| 3,259,374 A | 7/1966 | Doebl et al. |
| 3,346,242 A | 10/1967 | List |
| 3,935,099 A | 1/1976 | Weaver et al. |
| 3,959,569 A | 5/1976 | Burkholder, Jr. |
| 4,043,952 A | 8/1977 | Ganslaw et al. |
| 4,076,663 A | 2/1978 | Masuda et al. |
| 4,090,013 A | 5/1978 | Ganslaw et al. |
| 4,093,776 A | 6/1978 | Aoki et al. |
| 4,124,748 A | 11/1978 | Fujimoto et al. |
| 4,190,563 A | 2/1980 | Bosley et al. |
| 4,224,427 A | 9/1980 | Mueller et al. |
| 4,286,082 A | 8/1981 | Tsubakimoto et al. |
| 4,320,040 A | 3/1982 | Fujita et al. |
| 4,351,922 A | 9/1982 | Yoshida et al. |
| 4,367,323 A | 1/1983 | Kitamura et al. |
| 4,389,513 A | 6/1983 | Miyazaki |
| 4,416,711 A | 11/1983 | Jessop et al. |
| 4,446,261 A | 5/1984 | Yamasaki et al. |
| 4,455,284 A | 6/1984 | Sizyakov et al. |
| 4,497,930 A | 2/1985 | Yamasaki et al. |
| 4,526,937 A | 7/1985 | Hsu |
| 4,558,091 A | 12/1985 | Hubbard |
| 4,587,308 A | 5/1986 | Makita et al. |
| 4,625,001 A | 11/1986 | Tsubakimoto et al. |
| 4,652,001 A | 3/1987 | Rathbun et al. |
| 4,654,039 A | 3/1987 | Brandt et al. |
| 4,666,983 A | 5/1987 | Tsubakimoto et al. ........ 525/119 |
| 4,683,274 A | 7/1987 | Nakamura et al. |
| 4,690,996 A | 9/1987 | Shih et al. |
| 4,693,713 A | 9/1987 | Chmelir et al. |
| 4,721,647 A | 1/1988 | Nakanishi et al. |
| 4,734,478 A | 3/1988 | Tsubakimoto et al. |
| RE32,649 E | 4/1988 | Brandt et al. |
| 4,738,867 A | 4/1988 | Itoh et al. |
| 4,748,076 A | 5/1988 | Saotome |
| 4,755,562 A | 7/1988 | Alexander et al. |
| 4,769,427 A | 9/1988 | Nowakowsky et al. |
| 4,771,105 A | 9/1988 | Shirai et al. |
| 4,783,510 A | 11/1988 | Saotome ................ 525/329.7 |
| 4,824,901 A | 4/1989 | Alexander et al. |
| 4,826,917 A | 5/1989 | Kondo et al. |
| 4,863,989 A | 9/1989 | Obayashi et al. |
| 4,873,299 A | 10/1989 | Nowakowsky et al. |
| 4,880,455 A | 11/1989 | Blank |
| 4,948,818 A | 8/1990 | Carmody et al. |
| 4,950,692 A | 8/1990 | Lewis et al. |
| 4,972,019 A | 11/1990 | Obayashi et al. |
| 4,973,632 A | 11/1990 | Nagasuna et al. |
| 4,985,514 A | 1/1991 | Kimura et al. |
| 4,985,518 A | 1/1991 | Alexander et al. |
| 5,002,986 A | 3/1991 | Fujiura et al. |
| 5,026,800 A | 6/1991 | Kimura et al. |
| 5,030,205 A | 7/1991 | Holdaway et al. |
| 5,051,259 A | 9/1991 | Olsen et al. |
| 5,061,259 A | 10/1991 | Goldman et al. |
| RE33,839 E | 3/1992 | Chmelir et al. |
| 5,124,416 A | 6/1992 | Haruna et al. |
| 5,140,076 A | 8/1992 | Hatsuda et al. |
| 5,145,906 A | 9/1992 | Chambers et al. |
| 5,147,343 A | 9/1992 | Kellenberger ................ 604/368 |
| 5,149,335 A | 9/1992 | Kellenberger et al. ........ 604/372 |
| 5,154,713 A | 10/1992 | Lind |
| 5,164,459 A | 11/1992 | Kimura et al. |
| 5,180,798 A | 1/1993 | Nakamura et al. |
| 5,185,413 A | 2/1993 | Yoshinaga et al. |
| 5,229,488 A | 7/1993 | Nagasuna et al. |
| 5,244,735 A | 9/1993 | Kimura et al. |
| 5,250,640 A | 10/1993 | Irie et al. |
| 5,264,495 A | 11/1993 | Irie et al. |
| 5,275,773 A | 1/1994 | Irie et al. |
| 5,288,814 A | 2/1994 | Long, II et al. |
| 5,296,650 A | 3/1994 | Kobayashi et al. |
| 5,300,192 A | 4/1994 | Hansen et al. |
| 5,308,896 A | 5/1994 | Hansen et al. |
| 5,314,420 A | 5/1994 | Smith et al. |
| 5,322,896 A | 6/1994 | Ueda et al. |
| 5,328,935 A | 7/1994 | Van Phan et al. |
| 5,338,766 A | 8/1994 | Phan et al. |
| 5,369,148 A | 11/1994 | Takahashi et al. |
| 5,371,148 A | 12/1994 | Taylor et al. |
| 5,380,808 A | 1/1995 | Sumiya et al. |
| 5,385,983 A | 1/1995 | Graham |
| 5,409,771 A | 4/1995 | Dahmen et al. |
| 5,419,956 A | 5/1995 | Roe |
| 5,422,405 A | 6/1995 | Dairoku et al. ................ 525/384 |
| 5,439,993 A | 8/1995 | Ito et al. |
| 5,447,727 A | 9/1995 | Graham |
| 5,447,977 A | 9/1995 | Hansen et al. |
| 5,453,323 A | 9/1995 | Chambers et al. |
| 5,455,284 A | 10/1995 | Dahmen et al. |
| 5,462,972 A | 10/1995 | Smith et al. |
| 5,475,062 A | 12/1995 | Ishizaki ........................ 525/384 |
| 5,478,879 A | 12/1995 | Kajikawa et al. |
| 5,506,324 A | 4/1996 | Gartner et al. |
| 5,532,323 A | 7/1996 | Yano et al. |
| 5,538,783 A | 7/1996 | Hansen et al. |
| 5,543,215 A | 8/1996 | Hansen et al. |
| 5,543,433 A | 8/1996 | Doetzer et al. |
| 5,562,646 A | 10/1996 | Goldman et al. ............. 604/368 |
| 5,571,618 A | 11/1996 | Hansen et al. |
| 5,574,121 A | 11/1996 | Irie et al. |
| 5,589,256 A | 12/1996 | Hansen et al. |
| 5,597,873 A | 1/1997 | Chambers et al. |
| 5,599,335 A | 2/1997 | Goldman et al. |
| 5,601,452 A | 2/1997 | Ruffa |
| 5,601,542 A | 2/1997 | Melius et al. ................. 604/368 |
| 5,609,727 A | 3/1997 | Hansen et al. |
| 5,610,208 E | 3/1997 | Dairoku et al. |
| 5,610,220 A | 3/1997 | Klimmek et al. |
| 5,614,570 A | 3/1997 | Hansen et al. |
| 5,624,967 A | 4/1997 | Hitomi et al. |
| 5,633,316 A | 5/1997 | Gartner et al. |
| 5,656,087 A | 8/1997 | Kikuchi et al. |
| 5,668,078 A | 9/1997 | Sumiya et al. ................ 502/402 |
| 5,669,894 A | 9/1997 | Goldman et al. |
| 5,672,633 A | 9/1997 | Brehm et al. |
| 5,684,072 A | 11/1997 | Rardon et al. |
| 5,712,316 A | 1/1998 | Dahmen et al. |
| 5,728,742 A | 3/1998 | Staples et al. |
| 5,744,564 A | 4/1998 | Stanley, Jr. et al. |
| 5,760,080 A | 6/1998 | Wada et al. |
| 5,795,893 A | 8/1998 | Bondinell et al. |
| 5,797,893 A | 8/1998 | Wada et al. |
| 5,801,238 A | 9/1998 | Tanaka et al. |
| 5,837,789 A | 11/1998 | Stockhausen et al. |
| 5,843,575 A | 12/1998 | Wang et al. |
| 5,849,405 A | 12/1998 | Wang et al. |
| 5,851,672 A | 12/1998 | Wang et al. |
| 5,853,867 A | 12/1998 | Harada et al. |
| 5,858,535 A | 1/1999 | Wang et al. |
| 5,861,429 A | 1/1999 | Sato et al. |
| 5,883,158 A | 3/1999 | Nambu et al. |
| 5,973,042 A | 10/1999 | Yoshinaga et al. |

(56) References Cited

U.S. PATENT DOCUMENTS

| | | | |
|---|---|---|---|
| 5,981,070 A | 11/1999 | Ishizaki et al. | |
| 5,985,944 A | 11/1999 | Ishizaki et al. | |
| 5,987,070 A | 11/1999 | Fimoff et al. | |
| 5,994,440 A | 11/1999 | Staples et al. | |
| 6,037,431 A | 3/2000 | Shioji et al. | |
| 6,054,541 A | 4/2000 | Wada et al. | |
| 6,071,976 A | 6/2000 | Dairoku et al. | |
| 6,076,277 A | 6/2000 | Eyerer et al. | |
| 6,087,002 A | 7/2000 | Kimura et al. | |
| 6,087,450 A | 7/2000 | Breitbach et al. | |
| 6,099,950 A | 8/2000 | Wang et al. | |
| 6,100,305 A | 8/2000 | Miyake et al. | |
| 6,107,358 A | 8/2000 | Harada et al. | |
| 6,110,992 A | 8/2000 | Wada et al. | |
| 6,124,391 A | 9/2000 | Sun et al. | |
| 6,127,454 A | 10/2000 | Wada et al. | |
| 6,133,193 A | 10/2000 | Kajikawa et al. | |
| 6,136,973 A | 10/2000 | Suzuki et al. | |
| 6,140,395 A | 10/2000 | Hatsuda et al. | |
| 6,143,821 A | 11/2000 | Houben | |
| 6,150,582 A | 11/2000 | Wada et al. | |
| RE37,021 E | 1/2001 | Aida | |
| 6,174,929 B1 | 1/2001 | Hahnle et al. | |
| 6,174,978 B1 | 1/2001 | Hatsuda et al. | |
| 6,180,724 B1 | 1/2001 | Wada et al. | |
| 6,184,433 B1 | 2/2001 | Harada et al. | |
| 6,194,531 B1 | 2/2001 | Hatsuda et al. | |
| 6,207,772 B1 | 3/2001 | Hatsuda et al. | |
| 6,228,930 B1 | 5/2001 | Dairoku et al. | |
| 6,232,520 B1 | 5/2001 | Hird et al. | |
| 6,239,230 B1 | 5/2001 | Eckert et al. | |
| 6,241,928 B1 | 6/2001 | Hatsuda et al. | |
| 6,251,950 B1 | 6/2001 | Durden et al. | |
| 6,251,960 B1 | 6/2001 | Ishizaki et al. | |
| 6,254,990 B1 | 7/2001 | Ishizaki et al. | |
| 6,284,362 B1 | 9/2001 | Takai et al. | |
| 6,297,319 B1 | 10/2001 | Nagasuna et al. | |
| 6,297,335 B1 | 10/2001 | Funk et al. | |
| 6,300,275 B1 | 10/2001 | Weir | 502/402 |
| 6,300,423 B1 | 10/2001 | Engelhardt et al. | |
| 6,310,156 B1 | 10/2001 | Maeda et al. | |
| 6,313,231 B1 | 11/2001 | Hosokawa et al. | |
| 6,323,252 B1 | 11/2001 | Gartner et al. | 521/149 |
| 6,335,406 B1 | 1/2002 | Nagasuna et al. | |
| 6,360,077 B2 | 3/2002 | Mizoguchi | |
| 6,372,852 B2 | 4/2002 | Hitomi et al. | |
| 6,376,618 B1 | 4/2002 | Mitchell et al. | |
| 6,388,000 B1 | 5/2002 | Irie et al. | 524/566 |
| 6,403,700 B1 | 6/2002 | Dahmen et al. | |
| 6,414,214 B1 | 7/2002 | Engelhardt et al. | 604/368 |
| 6,417,425 B1 | 7/2002 | Whitmore et al. | |
| 6,433,058 B1 | 8/2002 | Weir et al. | |
| 6,444,744 B1 | 9/2002 | Fujimaru et al. | |
| 6,448,320 B1 | 9/2002 | Igarashi et al. | |
| 6,455,600 B1 | 9/2002 | Hahnle et al. | |
| 6,458,921 B1 | 10/2002 | Dairoku et al. | |
| 6,469,080 B2 | 10/2002 | Miyake et al. | |
| 6,472,478 B1 | 10/2002 | Funk et al. | |
| 6,514,615 B1 | 2/2003 | Jones et al. | |
| 6,559,239 B1 | 5/2003 | Riegel et al. | |
| 6,562,743 B1 | 5/2003 | Cook et al. | |
| 6,562,879 B1 | 5/2003 | Hatsuda et al. | |
| 6,565,768 B1 | 5/2003 | Dentler et al. | |
| 6,579,958 B2 | 6/2003 | Wilson | |
| 6,586,549 B1 | 7/2003 | Hatsuda et al. | |
| 6,599,989 B2 | 7/2003 | Wada et al. | |
| 6,605,673 B1 | 8/2003 | Mertens et al. | |
| 6,620,889 B1 | 9/2003 | Mertens et al. | |
| 6,620,899 B1 | 9/2003 | Morken et al. | |
| 6,657,015 B1 | 12/2003 | Riegel et al. | |
| 6,667,372 B1 | 12/2003 | Miyake et al. | |
| RE38,444 E | 2/2004 | Wada et al. | |
| 6,716,894 B2 | 4/2004 | Kajikawa et al. | |
| 6,716,929 B2 | 4/2004 | Wilson | |
| 6,720,073 B2 | 4/2004 | Lange et al. | |
| 6,727,345 B2 | 4/2004 | Kajikawa et al. | |
| 6,730,387 B2 | 5/2004 | Rezai et al. | |
| 6,743,391 B2 | 6/2004 | Sun et al. | |
| 6,787,001 B2 | 9/2004 | Sakamoto et al. | |
| 6,809,158 B2 | 10/2004 | Ikeuchi et al. | |
| 6,831,142 B2 | 12/2004 | Mertens et al. | |
| 6,835,325 B1 | 12/2004 | Nakamura et al. | |
| 6,841,229 B2 | 1/2005 | Sun et al. | |
| 6,849,665 B2 | 2/2005 | Frenz et al. | 521/64 |
| 6,927,268 B2 | 8/2005 | Matsumoto et al. | |
| 6,930,221 B1 | 8/2005 | Strandqvist | |
| 6,951,895 B1 | 10/2005 | Qin et al. | |
| 6,992,144 B2 | 1/2006 | Dairoku et al. | |
| 7,049,366 B2 | 5/2006 | Nakahara et al. | |
| 7,157,141 B2 | 1/2007 | Inger et al. | |
| 7,169,843 B2 | 1/2007 | Smith et al. | 524/556 |
| 7,173,086 B2 | 2/2007 | Smith et al. | 524/556 |
| 7,179,875 B2 | 2/2007 | Fuchs et al. | |
| 7,282,262 B2 | 10/2007 | Adachi et al. | |
| 7,285,599 B2 | 10/2007 | Mertens et al. | |
| 7,307,132 B2 | 12/2007 | Nestler et al. | |
| 7,378,453 B2 | 5/2008 | Nogi et al. | |
| 7,435,477 B2 | 10/2008 | Adachi et al. | |
| 7,473,739 B2 | 1/2009 | Dairoku et al. | |
| 7,510,988 B2 | 3/2009 | Wada et al. | |
| 7,557,245 B2 | 7/2009 | Nordhoff et al. | |
| 7,572,864 B2 | 8/2009 | Mertens et al. | |
| 7,582,705 B2 | 9/2009 | Dairoku et al. | |
| 7,745,537 B2 * | 6/2010 | Nakashima et al. | 525/119 |
| 7,750,085 B2 | 7/2010 | Torii et al. | |
| 7,803,880 B2 | 9/2010 | Torii et al. | |
| 7,816,445 B2 | 10/2010 | Dairoku et al. | |
| 7,851,550 B2 | 12/2010 | Kadonaga et al. | |
| 7,879,923 B2 | 2/2011 | Matsumoto et al. | |
| 7,960,469 B2 | 6/2011 | Adachi et al. | |
| 8,198,209 B2 * | 6/2012 | Torii et al. | 502/402 |
| 8,309,654 B2 | 11/2012 | Miyake et al. | |
| 8,430,960 B2 | 4/2013 | Sumakeris et al. | |
| 8,497,226 B2 | 7/2013 | Torii et al. | |
| 8,552,134 B2 | 10/2013 | Fujimaru et al. | |
| 8,596,931 B2 | 12/2013 | Nagashima et al. | |
| 2001/0025093 A1 | 9/2001 | Ishizaki et al. | |
| 2001/0046867 A1 | 11/2001 | Mizoguchi | |
| 2001/0053807 A1 | 12/2001 | Miyake et al. | |
| 2001/0053826 A1 | 12/2001 | Hosokawa et al. | |
| 2002/0013394 A1 | 1/2002 | Dairoku et al. | |
| 2002/0040095 A1 | 4/2002 | Dairoku et al. | |
| 2002/0072471 A1 | 6/2002 | Ikeuchi et al. | |
| 2002/0120074 A1 | 8/2002 | Wada et al. | |
| 2002/0120085 A1 | 8/2002 | Matsumoto et al. | |
| 2002/0127166 A1 | 9/2002 | Bergeron et al. | |
| 2002/0128618 A1 | 9/2002 | Frenz et al. | |
| 2002/0161132 A1 | 10/2002 | Irie et al. | |
| 2002/0165288 A1 | 11/2002 | Frenz et al. | |
| 2002/0169252 A1 | 11/2002 | Wilson | |
| 2002/0193492 A1 | 12/2002 | Wilson | |
| 2003/0020199 A1 | 1/2003 | Kajikawa et al. | |
| 2003/0060112 A1 | 3/2003 | Rezai et al. | |
| 2003/0065215 A1 | 4/2003 | Sakamoto et al. | |
| 2003/0069359 A1 | 4/2003 | Torii et al. | |
| 2003/0092849 A1 | 5/2003 | Dairoku et al. | |
| 2003/0100830 A1 | 5/2003 | Zhong et al. | |
| 2003/0118820 A1 | 6/2003 | Sun et al. | |
| 2003/0118821 A1 | 6/2003 | Sun et al. | |
| 2003/0153887 A1 | 8/2003 | Nawata et al. | |
| 2003/0207997 A1 | 11/2003 | Mertens et al. | |
| 2004/0019342 A1 | 1/2004 | Nagasuna et al. | |
| 2004/0024104 A1 | 2/2004 | Ota et al. | |
| 2004/0042952 A1 | 3/2004 | Bergeron et al. | |
| 2004/0050679 A1 | 3/2004 | Hammon et al. | |
| 2004/0071966 A1 | 4/2004 | Inger et al. | |
| 2004/0106745 A1 | 6/2004 | Nakashima et al. | |
| 2004/0110006 A1 | 6/2004 | Ishizaki et al. | |
| 2004/0110897 A1 | 6/2004 | Sakamoto et al. | |
| 2004/0110913 A1 | 6/2004 | Kanto et al. | |
| 2004/0110914 A1 | 6/2004 | Nakahara et al. | |
| 2004/0157734 A1 | 8/2004 | Mertens et al. | |
| 2004/0176544 A1 | 9/2004 | Mertens et al. | |
| 2004/0180189 A1 | 9/2004 | Funk et al. | |

(56) References Cited

U.S. PATENT DOCUMENTS

| | | |
|---|---|---|
| 2004/0181031 A1 | 9/2004 | Nogi et al. |
| 2004/0213892 A1 | 10/2004 | Jonas et al. ............... 427/2.3 |
| 2004/0236049 A1 | 11/2004 | Fuchs et al. |
| 2004/0242761 A1 | 12/2004 | Dairoku et al. |
| 2005/0000671 A1 | 1/2005 | Ishii et al. |
| 2005/0013865 A1 | 1/2005 | Nestler et al. |
| 2005/0020780 A1 | 1/2005 | Inger et al. |
| 2005/0048221 A1 | 3/2005 | Irie et al. ............... 427/558 |
| 2005/0049379 A1 | 3/2005 | Adachi et al. |
| 2005/0070071 A1 | 3/2005 | Henley et al. |
| 2005/0070671 A1 | 3/2005 | Torii et al. |
| 2005/0080194 A1 | 4/2005 | Satake et al. |
| 2005/0101680 A1 | 5/2005 | Sun et al. |
| 2005/0113542 A1 | 5/2005 | Irie et al. |
| 2005/0118423 A1* | 6/2005 | Adachi et al. ............ 428/402 |
| 2005/0154146 A1 | 7/2005 | Burgert |
| 2005/0176910 A1 | 8/2005 | Jaworek et al. |
| 2005/0209352 A1 | 9/2005 | Dairoku ............... 521/50 |
| 2005/0209411 A1 | 9/2005 | Nestler et al. |
| 2005/0215734 A1 | 9/2005 | Dairoku et al. |
| 2005/0215752 A1 | 9/2005 | Popp et al. |
| 2005/0221980 A1 | 10/2005 | Adachi et al. |
| 2005/0222459 A1 | 10/2005 | Nordhoff et al. |
| 2005/0222547 A1 | 10/2005 | Beruda et al. |
| 2005/0234413 A1 | 10/2005 | Funk et al. |
| 2005/0256469 A1 | 11/2005 | Qin et al. ............... 604/358 |
| 2005/0272600 A1 | 12/2005 | Wada et al. |
| 2005/0288182 A1 | 12/2005 | Torii et al. |
| 2006/0020078 A1 | 1/2006 | Popp et al. |
| 2006/0025536 A1 | 2/2006 | Dairoku et al. |
| 2006/0036043 A1 | 2/2006 | Nestler et al. |
| 2006/0073969 A1 | 4/2006 | Torii et al. ............... 502/400 |
| 2006/0074160 A1 | 4/2006 | Handa et al. |
| 2006/0079630 A1 | 4/2006 | Himori et al. |
| 2006/0089512 A1 | 4/2006 | Bennett et al. |
| 2006/0204755 A1 | 9/2006 | Torii et al. ............... 428/402 |
| 2006/0229413 A1 | 10/2006 | Torii et al. |
| 2007/0078231 A1 | 4/2007 | Shibata et al. |
| 2007/0101939 A1 | 5/2007 | Sumakeris et al. |
| 2007/0106013 A1 | 5/2007 | Adachi et al. ............ 524/566 |
| 2007/0149691 A1 | 6/2007 | Ishizaki et al. |
| 2007/0149716 A1 | 6/2007 | Funk et al. |
| 2007/0203280 A1 | 8/2007 | Okochi |
| 2007/0207924 A1 | 9/2007 | Ikeuchi et al. |
| 2007/0225422 A1 | 9/2007 | Sakamoto et al. |
| 2007/0239124 A1 | 10/2007 | Handa et al. |
| 2007/0254177 A1 | 11/2007 | Smith et al. |
| 2008/0021131 A1 | 1/2008 | Mertens et al. |
| 2008/0032888 A1 | 2/2008 | Nakamura et al. |
| 2008/0119586 A1 | 5/2008 | Byerly et al. ............ 523/111 |
| 2008/0119626 A1 | 5/2008 | Fujimaru et al. |
| 2008/0125533 A1 | 5/2008 | Riegel et al. ............ 524/417 |
| 2008/0139693 A1 | 6/2008 | Ikeuchi et al. |
| 2008/0161512 A1 | 7/2008 | Kawano et al. |
| 2008/0166410 A1 | 7/2008 | Funk et al. |
| 2009/0036855 A1 | 2/2009 | Wada et al. |
| 2009/0186542 A1 | 7/2009 | Kondo et al. ............ 442/118 |
| 2009/0234314 A1 | 9/2009 | Nakamura et al. |
| 2009/0239966 A1 | 9/2009 | Matsumoto et al. ......... 522/24 |
| 2010/0119312 A1* | 5/2010 | Nagashima et al. ......... 406/46 |
| 2010/0160883 A1 | 6/2010 | Jonas et al. ............... 604/368 |
| 2011/0301560 A1 | 12/2011 | Fujimura et al. |
| 2012/0298913 A1 | 11/2012 | Kondo et al. |

FOREIGN PATENT DOCUMENTS

| | | | |
|---|---|---|---|
| CA | 2 426 514 A1 | 3/2003 | |
| CA | 2 426 802 A1 | 4/2003 | |
| CN | 1181272 A | 5/1998 | |
| CN | 1204665 A | 1/1999 | |
| CN | 1344756 A | 4/2002 | |
| CN | 1610707 A | 4/2005 | |
| DE | 10221202 A1 | 7/2003 | |
| EP | 0 001 706 A1 | 5/1979 | |
| EP | 0 205 674 A1 | 12/1986 | |
| EP | 0 304 319 A2 | 2/1989 | |
| EP | 0 339 461 A1 | 11/1989 | |
| EP | 0 349 240 A2 | 1/1990 | |
| EP | 0 450 923 A2 | 10/1991 | |
| EP | 0 456 136 A2 | 11/1991 | |
| EP | 0 461 613 A1 | 12/1991 | |
| EP | 0 481 443 A1 | 4/1992 | |
| EP | 0 493 011 A2 | 7/1992 | |
| EP | 0 521 355 A1 | 1/1993 | |
| EP | 0 530 517 A1 | 3/1993 | |
| EP | 0 532 002 A1 | 3/1993 | |
| EP | 0 603 292 A1 | 6/1994 | |
| EP | 0 605 150 A1 | 7/1994 | |
| EP | 0 605 215 A1 | 7/1994 | |
| EP | 0 621 041 A1 | 10/1994 | |
| EP | 0 627 411 A1 | 12/1994 | |
| EP | 0 629 411 A1 | 12/1994 | |
| EP | 0 629 441 A1 | 12/1994 | |
| EP | 0 668 080 A2 | 8/1995 | |
| EP | 0 695 763 A1 | 2/1996 | |
| EP | 0 707 603 A1 | 4/1996 | |
| EP | 0 712 659 A1 | 5/1996 | |
| EP | 0 761 241 A2 | 3/1997 | |
| EP | 0 811 636 A1 | 12/1997 | |
| EP | 0 837 076 A2 | 4/1998 | |
| EP | 0 844 270 A1 | 5/1998 | |
| EP | 0 889 063 A1 | 1/1999 | |
| EP | 0 922 717 A1 | 6/1999 | |
| EP | 0 937 739 A2 | 8/1999 | |
| EP | 0 940 148 A1 | 9/1999 | |
| EP | 0 942 014 A2 | 9/1999 | |
| EP | 0 955 086 A2 | 11/1999 | |
| EP | 1 029 886 A2 | 8/2000 | |
| EP | 1 072 630 A1 | 1/2001 | |
| EP | 1 113 037 A2 | 7/2001 | |
| EP | 1 130 045 A2 | 9/2001 | |
| EP | 1 153 656 A2 | 11/2001 | |
| EP | 1 169 379 A1 | 1/2002 | |
| EP | 1 178 059 A2 | 2/2002 | |
| EP | 1 191 051 A2 | 3/2002 | |
| EP | 1 302 485 A1 | 4/2003 | |
| EP | 1 315 770 A1 | 6/2003 | |
| EP | 1 364 985 A1 | 11/2003 | |
| EP | 1 374 919 A2 | 1/2004 | |
| EP | 1 422 257 A1 | 5/2004 | |
| EP | 1 457 541 A1 | 9/2004 | |
| EP | 1 462 473 A1 | 9/2004 | |
| EP | 1 510 229 A1 | 3/2005 | |
| EP | 1 516 884 A2 | 3/2005 | |
| EP | 1 577 349 A1 | 9/2005 | |
| EP | 1 589 040 A1 | 10/2005 | |
| EP | 1 598 392 A2 | 11/2005 | |
| EP | 1 801 128 A2 | 6/2007 | |
| EP | 2 135 669 A1 | 12/2009 | |
| GB | 0 235 307 A | 6/1925 | |
| GB | 2 088 392 A | 6/1982 | |
| GB | 2 267 094 A | 11/1993 | |
| JP | 53-046389 B2 | 4/1978 | |
| JP | 54-037188 | 3/1979 | |
| JP | 55-038863 | 3/1980 | |
| JP | 55-133413 | 10/1980 | |
| JP | 56-133028 | 10/1981 | |
| JP | 56-136808 | 10/1981 | |
| JP | 57-073007 | 5/1982 | |
| JP | 57-094011 | 6/1982 | |
| JP | 57-158209 | 9/1982 | |
| JP | 58-501107 | 7/1983 | |
| JP | 58-180233 | 10/1983 | |
| JP | 59-062665 | 4/1984 | |
| JP | 59 080459 | 5/1984 | ............ C08L 33/02 |
| JP | 59-129232 | 7/1984 | |
| JP | 60-055002 | 3/1985 | |
| JP | 60-071623 | 4/1985 | |
| JP | 60-158861 | 8/1985 | |
| JP | 60-163956 | 8/1985 | |
| JP | 60-245608 | 12/1985 | |
| JP | 60-245608 A | 12/1985 | |
| JP | 61-016903 | 1/1986 | |

(56) References Cited

FOREIGN PATENT DOCUMENTS

| | | | |
|---|---|---|---|
| JP | 61-046241 | 3/1986 | |
| JP | 61-087702 | 5/1986 | |
| JP | 61-97333 | 5/1986 | |
| JP | 61-257235 | 11/1986 | |
| JP | 62-007745 | 1/1987 | |
| JP | 62-227904 | 10/1987 | |
| JP | 62-270607 | 11/1987 | |
| JP | 63-105064 | 5/1988 | |
| JP | 63-270741 | 11/1988 | |
| JP | 63-297408 | 12/1988 | |
| JP | 64-056707 | 3/1989 | |
| JP | 01-126310 | 5/1989 | |
| JP | 01-126314 | 5/1989 | |
| JP | 02-049002 | 2/1990 | |
| JP | 02-191604 | 7/1990 | |
| JP | 02-196802 A | 8/1990 | |
| JP | 02-255804 | 10/1990 | |
| JP | 02-300210 | 12/1990 | |
| JP | 03-052903 | 3/1991 | |
| JP | 03-095204 | 4/1991 | |
| JP | 03-179008 | 5/1991 | |
| JP | 04-175319 B2 | 6/1992 | |
| JP | 04-227705 A | 8/1992 | |
| JP | 05-202199 B2 | 8/1993 | |
| JP | 05-508674 | 12/1993 | |
| JP | 06-041319 | 2/1994 | |
| JP | 06-039485 | 3/1994 | |
| JP | 06-057010 | 3/1994 | |
| JP | 06-080818 | 3/1994 | |
| JP | 06-107846 | 4/1994 | |
| JP | 06-122708 | 5/1994 | |
| JP | 06-158658 | 6/1994 | |
| JP | 06-199969 | 7/1994 | |
| JP | 06-211934 | 8/1994 | |
| JP | 6-220227 | 8/1994 | ................ C08J 7/00 |
| JP | 6-262072 | 9/1994 | ............... B01J 20/26 |
| JP | 07-008883 | 1/1995 | |
| JP | 07-145326 A | 6/1995 | |
| JP | 07-224204 | 8/1995 | |
| JP | 07-228788 | 8/1995 | |
| JP | 07-242709 | 9/1995 | |
| JP | 8-27278 | 1/1996 | ................ C08J 3/24 |
| JP | 08-052203 | 2/1996 | |
| JP | 08-057311 | 3/1996 | |
| JP | 2-530668 A | 6/1996 | ................ C08F 2/00 |
| JP | 08-143782 | 6/1996 | |
| JP | 08-176311 | 7/1996 | |
| JP | 08-188602 | 7/1996 | |
| JP | 08-283318 | 10/1996 | |
| JP | 09-077832 | 3/1997 | |
| JP | 09-124710 | 5/1997 | |
| JP | 9-124879 | 5/1997 | ............. C08L 33/02 |
| JP | 09-136966 | 5/1997 | |
| JP | 09-235378 | 9/1997 | |
| JP | 09-509591 | 9/1997 | |
| JP | 09-278900 | 10/1997 | |
| JP | 09-290000 | 11/1997 | |
| JP | 10-045812 | 2/1998 | |
| JP | 10-075999 | 3/1998 | |
| JP | 10-114801 | 5/1998 | |
| JP | 10-147724 | 6/1998 | |
| JP | 10-273602 | 10/1998 | |
| JP | 02-847113 B2 | 1/1999 | |
| JP | 11-071425 | 3/1999 | |
| JP | 11-071425 A | 3/1999 | |
| JP | 11-071529 | 3/1999 | |
| JP | 02-881739 B2 | 4/1999 | |
| JP | 02-883330 B1 | 4/1999 | |
| JP | 11-106514 | 4/1999 | |
| JP | 11-240959 | 9/1999 | |
| JP | 11-241030 | 9/1999 | |
| JP | 11-254429 | 9/1999 | |
| JP | 11-258229 | 9/1999 | |
| JP | 11-302391 | 11/1999 | |
| JP | 11-315147 | 11/1999 | |
| JP | 02-995276 B2 | 12/1999 | |
| JP | 2000-026738 A | 1/2000 | |
| JP | 2000-053729 A | 2/2000 | |
| JP | 03-023203 B2 | 3/2000 | |
| JP | 03-028203 B2 | 4/2000 | |
| JP | 03-031306 B2 | 4/2000 | |
| JP | 2000-093792 | 4/2000 | ............... B01J 20/26 |
| JP | 2000-095965 A | 4/2000 | |
| JP | 2000-290381 A | 10/2000 | |
| JP | 2000-302876 A | 10/2000 | |
| JP | 2000-327926 A | 11/2000 | |
| JP | 03-115313 B2 | 12/2000 | |
| JP | 2001-011341 A | 1/2001 | |
| JP | 2001-040013 A | 2/2001 | |
| JP | 2001-040014 A | 2/2001 | |
| JP | 2001-096151 A | 4/2001 | |
| JP | 2001-098170 A | 4/2001 | |
| JP | 2001 137704 | 5/2001 | ............... B01J 20/26 |
| JP | 2001-224959 A | 8/2001 | |
| JP | 2001-226416 A | 8/2001 | |
| JP | 2001-252307 A | 9/2001 | |
| JP | 2001-523287 | 11/2001 | ................ C08J 3/12 |
| JP | 2001-523289 | 11/2001 | ................ C08J 3/20 |
| JP | 2002-035580 A | 2/2002 | |
| JP | 2002-085959 A | 3/2002 | |
| JP | 2002-121291 A | 4/2002 | |
| JP | 03-283570 B2 | 5/2002 | |
| JP | 2002-513043 A | 5/2002 | |
| JP | 2002-513059 A | 5/2002 | |
| JP | 2002-515079 A | 5/2002 | |
| JP | 2002-212204 A | 7/2002 | |
| JP | 2002-523526 A | 7/2002 | |
| JP | 2002-241627 A | 8/2002 | |
| JP | 2002-527547 A | 8/2002 | |
| JP | 2002-265528 A | 9/2002 | |
| JP | 2002-538275 A | 11/2002 | |
| JP | 2002-539281 A | 11/2002 | |
| JP | 2003-503554 A | 1/2003 | |
| JP | 2003-062460 A | 3/2003 | |
| JP | 2003-082250 | 3/2003 | ............ C08L 101/14 |
| JP | 2003-088553 A | 3/2003 | |
| JP | 2003-088554 A | 3/2003 | |
| JP | 2003-511489 | 3/2003 | ................ C08F 8/00 |
| JP | 2003-105092 A | 4/2003 | |
| JP | 2003-516431 A | 5/2003 | |
| JP | 2003-165883 A | 6/2003 | |
| JP | 2003-206381 A | 7/2003 | |
| JP | 2003-523484 A | 8/2003 | |
| JP | 2003-246810 A | 9/2003 | |
| JP | 2003-261601 A | 9/2003 | |
| JP | 2003-306609 A | 10/2003 | |
| JP | 2003-529647 A | 10/2003 | |
| JP | 2004-001355 A | 1/2004 | |
| JP | 2004-002891 A | 1/2004 | |
| JP | 03-501493 B2 | 3/2004 | |
| JP | 2004-509196 A | 3/2004 | |
| JP | 2004-121400 A | 4/2004 | |
| JP | 2004-512165 A | 4/2004 | |
| JP | 2004-210924 A | 7/2004 | |
| JP | 2004-217911 A | 8/2004 | |
| JP | 2004-261796 | 9/2004 | ............... B01J 20/26 |
| JP | 2004-261797 A | 9/2004 | |
| JP | 2004-300425 A | 10/2004 | |
| JP | 2004-339678 A | 12/2004 | |
| JP | 2004-352941 A | 12/2004 | |
| JP | 2005-054050 A | 3/2005 | |
| JP | 2005-081204 A | 3/2005 | |
| JP | 2005-97585 | 4/2005 | ............... C08F 2/44 |
| JP | 2005-105254 | 4/2005 | ............. C08L 33/02 |
| JP | 2005-288265 A | 10/2005 | |
| JP | 2006-008963 A | 1/2006 | |
| JP | 2006-068731 A | 3/2006 | |
| JP | 04-046617 B2 | 2/2008 | |
| JP | 2008-523196 | 7/2008 | ................ C08J 3/28 |
| JP | 2008-534695 A | 8/2008 | |
| JP | 04-214734 B2 | 1/2009 | |
| JP | 2010-065107 | 3/2010 | ............. C08L 33/02 |
| JP | 05-040780 B2 | 10/2012 | |
| JP | 05-156034 B2 | 3/2013 | |

(56) References Cited

FOREIGN PATENT DOCUMENTS

| | | |
|---|---|---|
| JP | 05-200068 B2 | 5/2013 |
| JP | 05-209022 B2 | 6/2013 |
| RU | 1777603 | 11/1992 |
| RU | 2 106 153 C1 | 3/1998 |
| RU | 2 183 648 C2 | 6/2002 |
| RU | 2 193 045 C2 | 11/2002 |
| SU | 1797612 | 8/1988 |
| TW | 228528 | 8/1994 |
| TW | 396173 B | 7/2000 |
| TW | 399062 B | 7/2000 |
| TW | 422866 B | 2/2001 |
| TW | 432092 B | 5/2001 |
| WO | WO-89/05327 A1 | 6/1989 |
| WO | WO-92/01008 A1 | 1/1992 |
| WO | WO-93/05080 A1 | 3/1993 |
| WO | WO-95/02002 A1 | 1/1995 |
| WO | WO-95/05856 A1 | 3/1995 |
| WO | WO-95/22355 A1 | 8/1995 |
| WO | WO-95/22356 A1 | 8/1995 |
| WO | WO-95/22358 A1 | 8/1995 |
| WO | WO-95/26209 A1 | 10/1995 |
| WO | WO 95/33558 | 12/1995 ............... B01J 20/26 |
| WO | WO-96/07437 A1 | 3/1996 |
| WO | WO-96/38296 A1 | 12/1996 |
| WO | WO 97/37695 | 10/1997 ............... A61L 15/60 |
| WO | WO-98/37149 A1 | 8/1998 |
| WO | WO-98/48857 A1 | 11/1998 |
| WO | WO-98/49221 A1 | 11/1998 |
| WO | WO-98/52979 A1 | 11/1998 |
| WO | WO-99/55393 A1 | 11/1999 |
| WO | WO-99/55767 A1 | 11/1999 |
| WO | WO 00/10619 | 3/2000 ............... A61L 15/60 |
| WO | WO-00/38607 A1 | 7/2000 |
| WO | WO-00/53644 A1 | 9/2000 |
| WO | WO-00/53664 A1 | 9/2000 |
| WO | WO-00/55245 A1 | 9/2000 |
| WO | WO-01/45758 A1 | 6/2001 |
| WO | WO-01/66056 A1 | 9/2001 |
| WO | WO-01/68156 A1 | 9/2001 |
| WO | WO-01/68375 A2 | 9/2001 |
| WO | WO-01/74913 A1 | 10/2001 |
| WO | WO-01/89591 A2 | 11/2001 |
| WO | WO-01/98382 A1 | 12/2001 |
| WO | WO-02/20068 A1 | 3/2002 |
| WO | WO-02/22717 A1 | 3/2002 |
| WO | WO 02/34384 | 5/2002 ............... B01J 20/00 |
| WO | WO-02/053198 A1 | 7/2002 |
| WO | WO-02/053199 A1 | 7/2002 |
| WO | WO-02/100451 A2 | 12/2002 |
| WO | WO-03/004550 A1 | 1/2003 |
| WO | WO-03/014172 A2 | 2/2003 |
| WO | WO-03/051415 A1 | 6/2003 |
| WO | WO-03/051940 A1 | 6/2003 |
| WO | WO-03/078378 A1 | 9/2003 |
| WO | WO-03/095510 A1 | 11/2003 |
| WO | WO-2004/003036 A1 | 1/2004 |
| WO | WO-2004/018005 A1 | 3/2004 |
| WO | WO-2004/052819 A2 | 6/2004 |
| WO | WO-2004/052949 A1 | 6/2004 |
| WO | WO-2004/061010 A1 | 7/2004 |
| WO | WO-2004/069293 A1 | 8/2004 |
| WO | WO-2004/069404 A1 | 8/2004 |
| WO | WO-2004/069915 A2 | 8/2004 |
| WO | WO-2004/069936 A1 | 8/2004 |
| WO | WO-2004/113452 A1 | 12/2004 |
| WO | WO-2005/027986 A1 | 3/2005 |
| WO | WO 2005/075070 | 8/2005 ............... B01J 20/26 |
| WO | WO-2005/097313 A1 | 10/2005 |
| WO | WO-2006/062253 A1 | 6/2006 |
| WO | WO 2006/062258 | 6/2006 ............... C08F 8/00 |
| WO | WO-2006/063229 A2 | 6/2006 |
| WO | WO-2006/109844 A1 | 10/2006 |
| WO | WO-2006/109882 A1 | 10/2006 |
| WO | WO 2007/032565 | 3/2007 ............... B01J 20/30 |
| WO | WO 2007/037522 | 4/2007 ............... C08L 33/02 |
| WO | WO-2007/116777 A1 | 10/2007 |
| WO | WO 2008/015980 | 2/2008 ............... C08J 3/12 |
| WO | WO 2008/120742 | 10/2008 ............... B01J 20/26 |
| WO | WO 2009/048160 | 4/2009 ............... C08J 3/24 |
| WO | WO 2010/029074 | 3/2010 ............... C08J 3/24 |
| WO | WO 2010/073658 | 7/2010 ............... C08J 3/12 |

OTHER PUBLICATIONS

Office Action dated Mar. 21, 2014 issued in U.S. Appl. No. 11/723,822.
Supplementary European Search Report dated Jan. 17, 2014 issued in EP Application No. 10820587.3.
US 6,863,978, 03/2005, Inger et al. (withdrawn).
"Chemicals Used for Treatment of Water", European Standard, EN 878, European Committee for Standardization, Jun. 2004.
"Solubility Parameter Values", The Polymer Handbook 3rd Edition, published by Wiley Interscience Publication, pp. 524, 525, 527-539.
A1: *Characterization Analysis* of the patent claims of EP 1 512 712 B1, Apr. 27, 2011.
A6: *The step (B) and the step (D) are performed within 10 minutes in total*, Möglichkeiten zu Merkmal.
Abstract of JP 06-211934 published on Aug. 2, 1994.
Abstract of JP 2000-026738 published on Jan. 25, 2000.
BASF Acrylic Acid Glacial, Technical Data Sheet, Mar. 2001.
Belle Lowe (http://www.chestofbooks.com/food/science/Experimental-Cookery/Starch-Part-3.html). Book published 1943.
Buchholz et al., Solution Polymerization, Modern Superabsorbent Polymer Technology, p. 93, 1997.
*Chemistry/Engineering Handbook*, modified version No. 6, edited by Chemistry/Engineering Committee, Maruzen Co. 1999.
Chinese Office Action dated Jul. 17, 2009 issued in Chinese Application No. 200680011103.1 with English translation.
Chinese Office Action dated May 18, 2007 issued in Chinese Application No. 200510076831.8 with English translation.
Chinese Office Action dated Dec. 23, 2013 issued in Chinese Application No. 201210313591.9 with English translation.
Database WPI Week 200454, Thomas Scientific, London, UK, AN 2004-561593, XP0002555199.
Decision to Grant a Patent for an Invention dated Aug. 14, 2009 issued in Russian Application No. 2007140959 with English translation.
Decision to Grant a Patent for an Invention dated Dec. 6, 2007 issued in Russian Application No. 2005140797/04(045428) with English translation.
Decision to Grant dated Aug. 14, 2009 issued in Russian Application No. 2007140959 with English translation.
Definition of "contain" from Merriam-Webster online dictionary, Apr. 2009.
Definition of "involve" from Merriam-Webster online dictionary, Apr. 2009.
European Office Action dated Dec. 2, 2005 issued in European Application No. 05013153.1.
European Search Report dated Aug. 1, 2007 issued in European Application No. 07005807.8.
European Search Report dated Dec. 1, 2009 issued in European Application No. 06731732.1.
European Search Report dated Jun. 11, 2007 issed in European Application No. 07005807.8.
European Search Report dated Dec. 2, 2009 issued in European Application No. 06731728.9.
European Search Report dated Nov. 26, 2007 issued in European Application No. 06026348.0.
European Search Report dated Jun. 3, 2008 issued in European Application No. 06026110.4.
Hammer mill (Technology), <http://de.wikipedia.org/wiki/Hammermühle_(Technik)>, printed Apr. 24, 2011.
http://www.home-water-purifiers-and-filters.com/carbon-water-filter.php, 2011.
Indian Office Action dated Jun. 9, 2011 issued in Indian Application No. 564/CHENP/2008.

(56) References Cited

OTHER PUBLICATIONS

International Search Report and International Preliminary Examination Report dated Oct. 12, 2004 issued in PCT Application No. PCT/JP2004/009242.
International Search Report dated Apr. 25, 2006 issued in PCT Application No. PCT/JP2006/304895.
International Search Report dated Dec. 5, 2005 issued in PCT Application No. PCT/JP2005/018073.
International Search Report dated Sep. 5, 2006 issued in PCT Application No. PCT/JP2006/311637.
Japanese Office Action dated Jul. 10, 2012 in Japanese Application No. 2007-080101 with English Translation.
Japanese Office Action dated Apr. 23, 2013 issued in Japanese Application No. 2007-080101 with English translation.
Japanese Office Action dated Mar. 29, 2011 issued in Japanese Application No. 2005-127818 with English translation.
Japanese Office Action dated Dec. 7, 2010 issued in Japanese Application No. 2005-127818 with English translation.
Korean Office Action dated Oct. 27, 2008 issued in Korean Application No. 10-2007-7022676 with English translation.
Kurimoto Powder System, *Continuous Kneading & Reacting System: KRC Kneader*, <http://www.kurimoto.co.jp/english/powdersystem/products/krc_Kneader.html>, printed Apr. 24, 2011.
Notice of Opposition dated Oct. 17, 2012 issued in EP Application No. 04773399.3 with English translation.
Notice of Opposition dated Apr. 28, 2011 issued in European Application No. 04021015.5 with English translation.
Notice of Opposition dated Oct. 28, 2013 issued in European Application No. 06731728.9 with English translation.
Office Action dated Apr. 1, 2010 issued in U.S. Appl. No. 11/883,621.
Office Action dated Aug. 1, 2012 issued in U.S. Appl. No. 11/693,355.
Office Action dated Jun. 1, 2006 issued in U.S. Appl. No. 10/933,319.
Office Action dated Jan. 10, 2011 issued in U.S. Appl. No. 12/805,685.
Office Action dated Jul. 11, 2012 issued in U.S. Appl. No. 11/883,621.
Office Action dated Feb. 12, 2014 issued in U.S. Appl. No. 11/883,929.
Office Action dated Dec. 14, 2012 issued in U.S. Appl. No. 11/723,822.
Office Action dated Jul. 14, 2009 issued in U.S. Appl. No. 11/723,822.
Office Action dated Jun. 14, 2010 issued in U.S. Appl. No. 10/562,140.
Office Action dated Mar. 14, 2007 issued in U.S. Appl. No. 10/562,140.
Office Action dated May 14, 2008 issued in U.S. Appl. No. 11/152,195.
Office Action dated Sep. 14, 2009 issued in U.S. Appl. No. 11/883,929.
Office Action dated Apr. 15, 2008 issued in U.S. Appl. No. 10/562,140.
Office Action dated Apr. 15, 2009 issued in U.S. Appl. No. 11/373,215.
Office Action dated Jun. 15, 2009 issued in U.S. Appl. No. 11/693,355.
Office Action dated Oct. 15, 2009 issued in U.S. Appl. No. 11/152,195.
Office Action dated Oct. 16, 2008 issued in U.S. Appl. No. 10/933,319.
Office Action dated Sep. 16, 2008 issued in U.S. Appl. No. 10/562,140.
Office Action dated Dec. 17, 2013 issued in U.S. Appl. No. 11/883,929.
Office Action dated Feb. 17, 2012 issued in U.S. Appl. No. 10/933,319.
Office Action dated Mar. 17, 2009 issued in U.S. Appl. No. 10/572,565.
Office Action dated Nov. 17, 2009 issued in U.S. Appl. No. 11/579,603.
Office Action dated Dec. 18, 2009 issued in U.S. Appl. No. 11/638,580.
Office Action dated Jun. 18, 2007 issued in U.S. Appl. No. 11/049,995.
Office Action dated Mar. 18, 2010 issued in U.S. Appl. No. 11/883,929.
Office Action dated Mar. 18, 2011 issued in U.S. Appl. No. 11/883,621.
Office Action dated Nov. 18, 2008 issued in U.S. Appl. No. 11/049,995.
Office Action dated Nov. 18, 2010 issued in U.S. Appl. No. 10/562,140.
Office Action dated Oct. 18, 2007 issued in U.S. Appl. No. 10/933,319.
Office Action dated Oct. 18, 2010 issued in U.S. Appl. No. 11/883,621.
Office Action dated Sep. 18, 2009 issued in U.S. Appl. No. 11/641,885.
Office Action dated Mar. 2, 2009 issued in U.S. Appl. No. 11/579,603.
Office Action dated Nov. 2, 2007 issued in U.S. Appl. No. 11/449,666.
Office Action dated Jul. 20, 2011 issued in U.S. Appl. No. 10/933,319.
Office Action dated Mar. 20, 2008 issued in U.S. Appl. No. 10/933,319.
Office Action dated Dec. 21, 2009 issued in U.S. Appl. No. 11/723,822.
Office Action dated Dec. 21, 2010 issued in U.S. Appl. No. 11/579,603.
Office Action dated Jan. 21, 2009 issued in U.S. Appl. No. 11/638,580.
Office Action dated Jun. 21, 2007 issued in U.S. Appl. No. 11/449,666.
Office Action dated May 21, 2010 issued in U.S. Appl. No. 11/638,580.
Office Action dated Mar. 22, 2010 issued in U.S. Appl. No. 11/641,885.
Office Action dated Oct. 22, 2013 issued in U.S. Appl. No. 11/723,822.
Office Action dated Dec. 23, 2013 issued in U.S. Appl. No. 12/083,238.
Office Action dated Oct. 23, 2006 issued in U.S. Appl. No. 10/933,319.
Office Action dated Sep. 23, 2011 issued in U.S. Appl. No. 12/083,238.
Office Action dated Dec. 24, 2008 issued in U.S. Appl. No. 11/373,215.
Office Action dated Feb. 26, 2010 issued in U.S. Appl. No. 11/693,355.
Office Action dated Jun. 26, 2009 issued in U.S. Appl. No. 11/638,580.
Office Action dated Mar. 26, 2013 issued in U.S. Appl. No. 11/883,621.
Office Action dated Nov. 27, 2009 issued in U.S. Appl. No. 11/693,355.
Office Action dated Aug. 28, 2012 issued in U.S. Appl. No. 12/805,685.
Office Action dated Feb. 28, 2007 issued in U.S. Appl. No. 10/933,319.
Office Action dated Nov. 28, 2012 issued in U.S. Appl. No. 11/693,355.
Office Action dated Oct. 28, 2008 issued in U.S. Appl. No. 11/152,195.
Office Action dated Oct. 28, 2009 issued in U.S. Appl. No. 10/572,565.
Office Action dated Sep. 28, 2007 issued in U.S. Appl. No. 10/562,140.
Office Action dated Apr. 30, 2007 issued in U.S. Appl. No. 11/449,666.

(56) References Cited

OTHER PUBLICATIONS

Office Action dated Apr. 30, 2009 issued in U.S. Appl. No. 11/579,603.
Office Action dated Aug. 31, 2010 issued in U.S. Appl. No. 11/883,929.
Office Action dated May 31, 2011 issued in U.S. Appl. No. 12/805,685.
Office Action dated Apr. 4, 2011 issued in U.S. Appl. No. 12/083,238.
Office Action dated Nov. 4, 2010 issued in U.S. Appl. No. 12/805,685.
Office Action dated Sep. 4, 2007 issued in U.S. Appl. No. 11/049,995.
Office Action dated Apr. 5, 2013 issued in U.S. Appl. No. 11/152,195.
Office Action dated Mar. 5, 2013 issued in U.S. Appl. No. 11/693,355.
Office Action dated May 7, 2009 issued in U.S. Appl. No. 11/152,195.
Office Action dated Dec. 8, 2011 issued in U.S. Appl. No. 11/883,621.
Office Action dated Jul. 8, 2010 issued in U.S. Appl. No. 11/579,603.
Office Action dated May 8, 2008 issued in U.S. Appl. No. 11/449,666.
Office Action dated May 8, 2013 issued in U.S. Appl. No. 11/723,822.
Office Action dated Feb. 9, 2009 issued in U.S. Appl. No. 10/562,140.
Partial European Search Report dated May 25, 2007 issued in European Application No. 06026348.0.
Partial European Search Report dated Jun. 11, 2007 issued in European Application No. 07 10 5112.2.
*Particle Size Analysis and Characterization of Classification Process: 6. Classification Methods*, Ullmann's Enc. Ind. Chem., 6th e.d. (2002) Electronic Release.
Pharmco Products Inc., Sodium Hydroxide 50% Product Specification Sheet (2002).
S. Kishi, "Handbook of Food Additives Edition 1981", Food and Science Company, pp. 285. (Partial English Translation).
S. Kishi: "Handbook of Food Additives Edition 1983", Food and Science Company, pp. 214, 217, 219, 221. (Partial English Translation).
Saxena (ftp://ftp.fao.org/es/esn/jecfa/cta/CTA_61_PVA.pdf) published 2004.
State Intellectual Property Office of the P.R. China Examination Report dated Jan. 20, 2009.
Taiwan Office Action dated Nov. 8, 2011 issued in Taiwanese Application No. 095147238 with English translation.
The Polymer Handbook, 3rd Edition, p. 524 and p. 527-539.
Ulimann's Encyclopedia of Industrial Chemistry (2003, Bd 33:S. 241-242, Bd.8:S. 247-248).
Ulshöfer et al., *Mathematical formula collection for secondary school*, Verlag Konrad Wittwer Stuttgart, 3rd e.d., p. 4, 1988 (with English translation).
www.nichidene.com/Eng/kkh/b/b-2.htm.
Zschimmer & Schwarz (http://www.tandem-chemiscal.com/principles/zschimmer/ceramics_aux/special_info/E_PVAzubereitungen%5B1%5D.pdf) downloaded Dec. 4, 2009.
Affidavit, Dr. Christian Speyerer, pp. 1-3.
Buchholz, F.L., et al. (1997) "Modern superabsorbent polymer technology", *Wiley-VCH*, pp. 149-153.
Buchholz, F.L., et al. (1997) "Modern superabsorbent polymer technology", *Wiley-VCH*, pp. 178.
Buchholz, F.L., et al. (1997) "Modern superabsorbent polymer technology", *Wiley-VCH*, pp. 192-221.
Decision rejecting the opposition dated Jun. 24, 2014 issued in EP Application No. 04746711.3.
Delivery Note No. 89077237 dated May 19, 1999.
Delivery Note No. 89097648 dated Aug. 24, 1999.
Statement of Delivery No. 89055427 dated Feb. 10, 1999—with English Translation.
Statement of Delivery No. 89055472 dated Feb. 10, 1999—with English Translation.
Summons to attend oral proceedings dated Jun. 10, 2014 issued in EP Application No. 04773399.3.
Office Action dated Aug. 21, 2014 issued in U.S. Appl. No. 11/723,822.
Office Action dated Apr. 1, 2014 issued in Japanese Application No. 2007-080101 with full English translation.
Office Action dated Sep. 25, 2014 issued in U.S. Appl. No. 12/083,238.

\* cited by examiner

PARTICULATE WATER ABSORBENT AND PROCESS FOR PRODUCTION THEREOF

CROSS-REFERENCE TO RELATED APPLICATIONS

This application is a National Phase entry of International Application No. PCT/JP2010/066957 filed on 29 Sep. 2010, which claims priority under 35 U.S.C. §§119(a) and 365(b) to JP Application No. 2009-224756 filed on 29 Sep. 2009 and JP Application No. 2010-084530 filed on 31 Mar. 2010. Each of the above recited patent applications are incorporated herein by reference in their entirety.

TECHNICAL FIELD

The present invention relates to a particulate water absorbing agent suitable for use in sanitary materials such as disposable diapers, sanitary napkins and so-called incontinence pads, and relates to a method for producing the particulate water absorbing agent.

BACKGROUND ART

An absorbent core constituted by hydrophilic tissue (e.g., pulp) and a water absorbing resin has been in widespread use in sanitary materials such as disposable diapers, sanitary napkins and so-called incontinence pads. The absorbent core is used for the purpose of absorbing bodily fluids.

In recent years, such sanitary materials have been more functionalized and made thinner. The amount of a water absorbing resin used in each sanitary product shows an increasing trend, and the ratio of the water absorbing resin to the entire absorbent core constituted by the water absorbing resin and hydrophilic tissue shows an increasing trend. That is, the sanitary products have been reduced in thickness without a reduction in their absorbing capacity by increasing the ratio of the water absorbing resin in the absorbent core by (i) reducing the amount of hydrophilic tissue which is small in bulk density while (ii) increasing the amount of a water absorbing resin which is excellent in water absorbing property and is large in bulk density.

However, in order to produce sanitary products etc. such as disposable diapers which are to be highly-functionalized and reduced in thickness, it is necessary to incorporate a highly moisture-absorptive water absorbing resin into hydrophilic tissue. Depending on operating environment and climate conditions, the water absorbing resin may cause blocking in a storage hopper or in a transport line or may adhere to an apparatus or a pipe etc. This hinders stable production.

In view of this, there have been disclosed techniques of adding an inorganic substance such as amorphous silicon dioxide or kaoline etc. to a water absorbing resin to obtain a water absorbing agent that is excellent in fluidity after moisture absorption (Patent Literatures 1 to 4). However, the techniques of Patent Literatures 1 to 4 have a problem in which water absorbency against pressure of the water absorbing agent is reduced.

Further, there have been disclosed techniques of coating a surface of a water absorbing resin with polysiloxane or a specific surfactant etc. (Patent Literatures 5 to 8). However, the techniques of Patent Literatures 5 to 8 also have a problem in which, since the water absorbing resin is caused to be excessively hydrophobic or its surface tension is reduced, Re-Wet in disposable diapers is increased. Further, water absorbing resins obtained in Patent Literatures 1 to 15 have, in addition to the problem of fluidity (blocking resistance) after moisture absorption, a problem in which its moisture content is generally small and its particles are low in stability to shock.

Further, according to the technique described in Patent Literature 9, there has been a problem in which a rate of water absorption of a particulate water absorbing agent decreases because a metallic soap is hydrophobic. Therefore, an absorbing article using such a particulate water absorbing agent cannot have sufficient water absorbing property. Further, since the metallic soap is handled in a powdery state, there have been safety and health problems such as deterioration in operating environments due to powder dust or a high risk of dust explosion. Moreover, the techniques disclosed in Patent Literatures 11 and 12 are not sufficient to obtain a recent particulate water absorbing agent having excellent physical properties (e.g., high absorbency against pressure), and the technique described in Patent Literature 15 has a problem in which the yield and productivity are low although particle size is controlled.

In view of such circumstances, there have been disclosed techniques of adding, in order to improve stability to shock and prevent powder dust etc., a small amount of (several wt %) of) water to a surface-crosslinked water absorbing resin (Patent Literatures 16 to 20). However, such improved techniques also have a problem in which (i) adding water causes adhesive force between particles and thus applies a heavy load on a mixing apparatus, and as a result, the mixing apparatus tends to stop more frequently and (ii) adding a mixing auxiliary agent (e.g., inorganic salt) causes a reduction in physical properties (e.g., absorbency against pressure) of the water absorbing resin.

That is, the "stability to shock" and "water absorbing property (CRC, AAP) and fluidity after moisture absorption" are in a trade-off relationship. According to the conventional techniques, it has been extremely difficult to improve both of these properties.

The water absorbing agent or the water absorbing resin as has been described is desired to have for example the following properties: excellent free swelling capacity (CRC) and excellent absorbency against pressure (AAP), high liquid permeability (SFC and GBP etc.), high rate of water absorption (FSR and Vortex), high gel strength, and low extractable content (Extr). However, since the water absorbing properties depend on crosslink density, these properties may not be directly proportional to each other. For example, if the crosslink density is increased, the gel strength increases but the water absorbing capacity decreases. In order to suppress such phenomena and to obtain a water absorbing agent that has high absorption capacity and relatively high rate of absorption etc., there has been a method of coating surfaces of water absorbing resin particles with a surfactant or nonvolatile carbon hydride. This method improves dispensability of water absorbed in the initial stage; however, is not effective enough to improve the rate of absorption and suction of each of the particles.

In view of such circumstances, there has been proposed a method of imparting a crosslinked structure not only to inside a water absorbing resin but also to the surface of the water absorbing resin (i.e., surface crosslinking of a water absorbing resin). For example, there have been disclosed methods of increasing crosslink density on a surface of a water absorbing resin by using an organic surface crosslinking agent or an inorganic surface crosslinking agent (Patent Literatures 21 to 23).

Examples of a known crosslinking agent for use in such methods include: polyhydric alcohols; oxazolidinone; alkylene carbonate; polyhydric glycidyl ethers; haloepoxy compounds; polyhydric aldehydes; polyhydric amines; and polyvalent metal salts. However, using such surface crosslinking agents causes a problem in which for example a crosslinkage-forming reaction requires high temperature or takes a long time and some crosslinking agents will remain unreacted.

In view of circumstances, there has been also known a method of surface treatment utilizing a polyvalent metal ionic crosslinking reaction, which can occur at low temperature or room temperature (Patent Literature 23). However, such a method has a problem (i) in which a surface crosslinking agent made from a polyvalent metal generally has low physical properties such as absorbency against pressure (AAP) and (ii) the combined use of a polyvalent metal and some other surface treatment method causes a reduction in absorbency against pressure (AAP). Further, a surface crosslinking reaction, such as a dehydration reaction using a polyhydric alcohol serving as a surface crosslinking agent, requires heat treatment. This excessively reduces moisture content of the water absorbing resin and/or causes coloration of the water absorbing resin. Moreover, there has been a problem in which the reduction in moisture content due to surface crosslinkage reduces powder property (shock resistance).

In view of such circumstances, as an alternative to the surface crosslinkage using the surface crosslinking agent such as those described in Patent Literatures 21 to 23 etc., there have been proposed methods of surface crosslinking using a radical polymerization initiator (Patent Literatures 24, 29, 30) and methods of surface crosslinking for polymerizing monomers on a surface of a water absorbing resin (Patent Literatures 25 to 28). Specifically, for example, there has been known a method of bringing an aqueous solution containing a peroxide radical initiator into contact with resin and heating the resin to decompose the radical initiator, thereby introducing crosslinkage into polymer chains in a shallow surface of the resin (Patent Literature 24).

Further, there has been a method of impregnating a water absorbing resin with water-soluble unsaturated ethylene monomers and polymerizing the water-soluble unsaturated ethylene monomers, and heating the water absorbing resin to obtain a water absorbing resin improved so that the crosslink density in shallow surfaces of water absorbing resin particles is higher than that inside the particles (Patent Literature 25). Furthermore, there have been proposed surface treatment methods each of which is for use in a method of polymerizing monomers on a surface of a water absorbing resin. Each of the surface treatment methods includes adding a radical polymerizable compound to a water absorbing resin and thereafter irradiating the water absorbing resin with activating light (preferably with a ultraviolet ray) (Patent Literatures 26 to 28). Furthermore, there have been proposed surface treatment methods each of which is for use in a method of surface-crosslinking a water absorbing resin with a radical polymerization initiator. Each of the surface treatment methods includes irradiation with activating light (preferably with a ultraviolet ray) (Patent Literatures 29 and 30). Moreover, there has been proposed a surface treatment method using an ultraviolet ray, which method uses a transition metal such as Ag, Fe, Cr and/or Ce etc. (Patent Literature 31).

According to the methods of Patent Literatures 23 to 31, crosslinking can be achieved at low temperatures or room temperature, and a resulting surface-crosslinked water absorbing resin has high moisture content. However, these methods have a problem in which, generally, the absorbency against pressure (AAP), in particular absorbency against pressure under heavy load (AAP 0.7), is difficult to increase.

Further, the surface crosslinking methods described in Patent Literatures 21 to 30 have a problem in which a surface-crosslinked water absorbing resin generally has a low moisture content, and particles of such a water absorbing resin have low stability to shock etc. In order to improve the stability to shock and to prevent powder dust etc., there have been proposed techniques of adding about several percentage of water to a surface-crosslinked water absorbing resin (Patent Literatures 16, 17 and 20). However, such techniques have a problem in which adding water and its auxiliary agent (e.g., inorganic salt) reduces physical properties (e.g., absorbency against pressure) of the water absorbing resin. Further, there has been a problem in which the amount of residual monomers increases due to surface crosslinking (Patent Literature 32).

Further, conventionally, there have been proposed water absorbing resins mainly for disposable diapers, in which water absorbing resin many physical properties such as absorbency against pressure (AAP), water absorbency (CRC) and liquid permeability (GBP, SFC) are controlled (Patent Literatures 17, 20 and 33 to 43). Further, there have been known water absorbing resins each having a high moisture content, such as those described in Patent Literatures 17, 20 and 32. None of these water absorbing resins provide good performances, because a large amount of Re-Wet or leakage etc. occurs when these water absorbing resins are used in disposable diapers.

CITATION LIST

Patent Literatures

Patent Literature 1
Japanese Patent Application Publication, Tokukaisho, No 59-80459 A
Patent Literature 2
Japanese Patent Application Publication, Tokukai, No. 2000-093792 A
Patent Literature 3
Japanese Patent Application Publication, Tokukai, No. 2001-137704 A
Patent Literature 4
Pamphlet of International Publication, No. WO2000/010619
Patent Literature 5
Pamphlet of International Publication, No. WO95/033558
Patent Literature 6
Japanese Patent Application Publication, Tokukai, No. 2003-082250 A
Patent Literature 7
Pamphlet of International Publication, No. WO2002/034384
Patent Literature 8
Pamphlet of International Publication, No. WO97/37695
Patent Literature 9
Japanese Patent Application Publication, Tokukai, No. 2004-261796 A
Patent Literature 10
Japanese Patent Application Publication, Tokukaisho, No. 61-51658 A
Patent Literature 11
Pamphlet of International Publication, No. WO2010/073658
Patent Literature 12
Japanese Patent Application Publication, Tokukai, No. 2010-065107 A
Patent Literature 13
Japanese Patent Application Publication, Tokukaihei, No. 6-220227 A
Patent Literature 14
Japanese Patent Application Publication, Tokukaihei, No. 8-027278 A Patent Literature 15
Pamphlet of International Publication, No. WO2005/075070
Patent Literature 16
Japanese Translation of PCT Patent Application, Tokuhyo, No. 2003-511489 A
Patent Literature 17
Japanese Translation of PCT Patent Application, Tokuhyo, No. 2001-523287 A
Patent Literature 18
Japanese Patent No. 3103754
Patent Literature 19
Pamphlet of International Publication, No. WO2008/015980
Patent Literature 20
Japanese Patent Application Publication, Tokukaihei, No. 9-124879 A
Patent Literature 21
Specification of U.S. Pat. No. 4,666,983
Patent Literature 22
Specification of U.S. Pat. No. 5,422,405
Patent Literature 23
Specification of US Patent Application Publication, No. 2007/0106013
Patent Literature 24
Specification of U.S. Pat. No. 4,783,510
Patent Literature 25
Japanese Patent No. 2530668
Patent Literature 26
Specification of US Patent Application Publication No. 2005/048221
Patent Literature 27
Specification of US Patent Application Publication No. 2009/0239966
Patent Literature 28
Pamphlet of International Publication, No. WO2009/048160
Patent Literature 29
Pamphlet of International Publication, No. WO2006/062258
Patent Literature 30
Pamphlet of International Publication, No. WO2007/032565
Patent Literature 31
Pamphlet of International Publication, No. WO2010/029074
Patent Literature 32
Specification of U.S. Pat. No. 6,388,000
Patent Literature 33
Specification of U.S. Pat. No. 5,562,646
Patent Literature 34
Specification of US Patent Application Publication No. 2005/0256469
Patent Literature 35
Specification of U.S. Pat. No. 7,169,843
Patent Literature 36
Specification of U.S. Pat. No. 7,173,086
Patent Literature 37
Specification of U.S. Pat. No. 6,414,214
Patent Literature 38
Specification of U.S. Pat. No. 6,849,665
Patent Literature 39
Specification of US Patent Application Publication No. 2008/125533
Patent Literature 40
Specification of U.S. Pat. No. 5,147,343
Patent Literature 41
Specification of U.S. Pat. No. 5,149,335
Patent Literature 32
Specification of US Patent Application Publication No. 2008/119586
Patent Literature 43
Specification of U.S. Pat. No. 5,601,542

SUMMARY OF INVENTION

Technical Problem

An object of the present invention is to provide (i) a particulate water absorbing agent which is excellent in fluidity after moisture absorption and is excellent in absorbency against pressure, stability to shock and rate of water absorption and (ii) a method of producing the particulate water absorbing agent.

Another object of the present invention is to provide (i) a particulate water absorbing agent which reduces load applied on a mixing apparatus when water is added, which contains a certain amount of water, and whose physical properties are improved and kept and (ii) a method of producing the particulate water absorbing agent.

A further object of the present invention is to provide a method of easily and efficiently producing a particulate water absorbing agent without causing (i) deterioration due to powder dust in operating environment and/or (ii) dust explosion due to powder dust.

Providing such particulate water absorbing agents makes it possible to provide an absorbing article (i) in which the concentration of a water absorbent agent used in an absorbent core of a disposable diaper is between 20 wt % and 100 wt %, more preferably between 25 wt % and 90 wt %, and particularly preferably between 30 wt % and 80 wt % and (ii) which is excellent in Re-Wet and in urine absorption capacity etc. In particular, since the absorbent core is not affected by a damage on the water absorbing agent even if the water absorbing agent is damaged by an absorbent core production apparatus, it is possible to provide an absorbent core which is not affected by apparatuses, causes no leakage, and is excellent in performance. That is, it is possible to achieve excellent performance in a practical absorbent core.

Solution to Problem

In order to attain the above objects, the present invention provides the following first to fourth water absorbing agents. Further, in order to attain the above objects and further to provide the first to fourth water absorbing agents, the present invention provides the following water absorbing agent production methods 1 to 3.

It should be noted that each of the water absorbing agent production methods 1 to 3 of the present invention is a method of producing a particulate water absorbing agent which (i) contains a water absorbing resin as a main component and (ii) contains a polyvalent metal cation and a certain amount of water. Each of the first to fourth water absorbing agents of the present invention can be obtained by for example the production methods 1 to 3, and (i) contains a water absorbing resin as a main component and (ii) contains a polyvalent metal cation and a certain amount of water. Further, the first to fourth water absorbing agents and their production methods 1 to 3 have a common object and bring about the same effect.

<First Water Absorbing Agent>

A particulate water absorbing agent (first water absorbing agent) in accordance with the present invention is a particulate water absorbing agent containing a water absorbing resin as a main component, the particulate water absorbing agent containing a polyvalent metal (in its surface) and satisfying the following requirements (1) through (4):

(1) a polyvalent metal cation is contained in an amount between 0.001 wt % and 5 wt % relative to the amount of the particulate water absorbing agent;

(2) an absorbency without pressure (CRC) of the particulate water absorbing agent is not less than 28 (g/g) and an absorbency against pressure (AAP 4.83 kPa) of the particulate water absorbing agent is not less than 10 (g/g);
(3) the absorbency against pressure and the absorbency without pressure satisfy the inequality: 77≤Absorbency against pressure (AAP 4.83 kPa)+1.8×Absorbency without pressure (CRC)≤100; and
(4) a moisture content of the particulate water absorbing agent is between 5 wt % and 20 wt %.

The first water absorbing agent is preferably configured such that the polyvalent metal cation is a metallic soap or a water-soluble polyvalent metal salt.

<Second Water Absorbing Agent>

A particulate water absorbing agent (second water absorbing agent) in accordance with the present invention contains: water absorbing resin particles; a metallic soap (an organic salt of a polyvalent metal); water; and a dispersion stabilizer.

<Third Water Absorbing Agent>

A particulate water absorbing agent (third water absorbing agent) in accordance with the present invention contains: a water absorbing resin; and a metallic soap (an organic salt of a polyvalent metal), a moisture content of the particulate water absorbing agent being between 5 wt % and 20 wt %.

<Fourth Water Absorbing Agent>

A particulate water absorbing agent (fourth water absorbing agent) in accordance with the present invention is a particulate water absorbing agent containing, as a main component, a surface-treated polyacrylic acid (salt) water absorbing resin, the particulate water absorbing agent satisfying the following requirements (2), (4) and (5):
(2) an absorbency without pressure (CRC) of the particulate water absorbing agent is not less than 28 (g/g) and an absorbency against pressure (AAP 4.83 kPa) of the particulate water absorbing agent is not less than 10 (g/g);
(4) a moisture content of the particulate water absorbing agent is between 5 wt % and 20 wt %; and
(5) a vertical diffusion absorbency under pressure (VDAUP) of the particulate water absorbing agent is not less than 15 g.

The fourth water absorbing agent preferably contains a water-soluble polyvalent metal salt as a polyvalent metal cation.

Each of the second to fourth water absorbing agents preferably contains 0.001 wt % to 5 wt % of polyvalent metal cation(s). Further, each of the second to fourth water absorbing agents is preferably configured such that the absorbency against pressure and the absorbency without pressure satisfy the inequality: 77≤Absorbency against pressure (AAP 4.83 kPa)+1.8×Absorbency without pressure (CRC)≤100.

<Water Absorbing Agent Production Method 1>

A method of producing a particulate water absorbing agent (water absorbing agent production method 1) in accordance with the present invention includes mixing an aqueous dispersion containing a metallic soap (an organic salt of a polyvalent metal) and a dispersion stabilizer with a water absorbing resin.

<Water Absorbing Agent Production Method 2>

A method of producing a particulate water absorbing agent (water absorbing agent production method 2) in accordance with the present invention includes: the step of adding a metallic soap (an organic salt of a polyvalent metal) and water to a water absorbing resin; and controlling a moisture content of the water absorbing agent to between 5 wt % and 20 wt %.

<Water Absorbing Agent Production Method 3>

A method of producing a particulate water absorbing agent (water absorbing agent production method 3) in accordance with the present invention is a method of producing a particulate water absorbing agent which contains a water absorbing resin as a main component, the method including surface-treating the water absorbing resin by a surface treatment method including the steps of
(a) mixing an acid radical-containing radical-polymerizable monomer, a polyvalent metal compound and water with the water absorbing resin and
(b) polymerizing the acid radical-containing radical-polymerizable monomer.

<Relation Between Water Absorbing Agents and Water Absorbing Agent Production Methods>

A method of producing each of the foregoing water absorbing agents is not limited to the foregoing production methods. For example, each of the foregoing water absorbing agents can be obtained by the foregoing production method 1 to 3.

Specifically, the second water absorbing agent can be obtained by for example the water absorbing agent production method 1.

The third water absorbing agent can be obtained by for example the water absorbing agent production method 2.

Further, each of the first and fourth water absorbing agents can be obtained by for example the water absorbing agent production methods 1 to 3, which methods preferably include controlling physical properties so that a particulate water absorbing agent obtained by mixing a polyvalent metal compound or a metallic soap (an organic salt of a polyvalent metal) satisfies the following requirements (1), (2) and (4). The physical properties can be controlled as appropriate in accordance with the claims depending from the water absorbing agent production methods 1 to 3 or according to this Description etc.
(1) A polyvalent metal cation is contained in an amount between 0.001 wt % and 5 wt % relative to the amount of the particulate water absorbing agent.
(2) An absorbency without pressure (CRC) of the particulate water absorbing agent is not less than 28 (g/g) and an absorbency against pressure (AAP 4.83 kPa) of the particulate water absorbing agent is not less than 10 (g/g).
(4) A moisture content of the particulate water absorbing agent is between 5 wt % and 20 wt %.

Advantageous Effects of Invention

According to the present invention, i.e., according to the first to fourth water absorbing agents and their production methods 1 to 3, it is possible to provide (i) a particulate water absorbing agent which is excellent in fluidity after moisture absorption (blocking rate after moisture absorption), absorbency against pressure (AAP), stability to shock (dusting rate) and rate of water absorption and (ii) a method of producing the particulate water absorbing agent. That is, it is possible to provide an excellent particulate water absorbing agent containing a certain amount of water and a production method thereof, each of which is capable of improving the performances that are in a trade-off relationship, i.e., the "stability to shock (dusting rate)" and the "fluidity after moisture absorption (blocking rate after moisture absorption) and absorbency against pressure (AAP)".

Further, in a case where a particulate water absorbing agent in accordance with the present invention is used in a sanitary material such as a disposable diaper, it is possible to prevent the sanitary material from being destroyed due to damage caused to the particulate water absorbing agent during production of the sanitary material. Accordingly, it is possible to provide an excellent water absorbing property.

DESCRIPTION OF EMBODIMENTS

Figure 1:
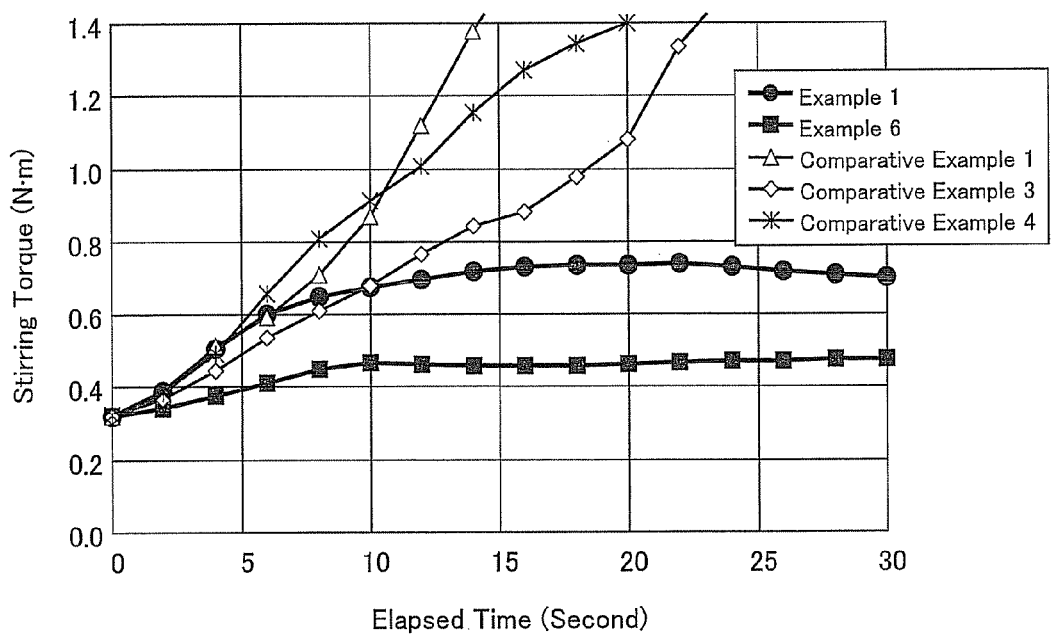
FIG. 1 is a graph illustrating elapsed time versus stirring torque after water starts being added in Examples 1 and 6 and Comparative Examples 1, 3 and 4.

The following description discusses, in detail, a particulate water absorbing agent and a production method thereof in accordance with the present invention. Note, however, that the scope of the present invention is not limited to the descriptions. Therefore, the present invention can be altered as appropriate so as to be implemented, provided that the objects of the present invention are attained. Specifically, the present invention is not limited to the following embodiments, but may be altered within the scope of the claims. An embodiment derived from a proper combination of technical means disclosed in different embodiments is encompassed in the technical scope of the present invention. It should be noted that, in this Description, the terms "mass" and "weight" have the same meaning.

[1] Definition of Terms (1-1) "Water Absorbing Resin", "Water Absorbing Resin Powder", "Water Absorbing Resin Precursor" and "Water Absorbing Resin Particles"

A "water absorbing resin" as used in the present invention means a water-swelling, water-insoluble gelatinizer in the form of a polymer. It should be noted here that the "water-swelling" means that a CRC (centrifugal retention capacity) specified in ERT 441.2-02 is not less than 5 [g/g], and the "water-insoluble" means that an Ext (extractable content) specified in ERT 470.2-02 is between 0 wt % and 50 wt %.

The water absorbing resin can be designed as appropriate depending on its use, and therefore is not particularly limited in its design. Note, however, that the water absorbing resin is preferably a hydrophilic crosslinked polymer obtained by polymerizing crosslinking unsaturated monomers each having a carboxyl group. Further, the water absorbing resin does not have to consist only of a polymer (i.e., 100 wt % polymer), and therefore can be the one that is surface-crosslinked or a composition containing an additive etc., provided that the foregoing performances are achieved.

Further, as used in the present invention, a water absorbing resin obtained by pulverizing the hydrophilic crosslinked polymer to powder, which water absorbing resin has not yet been surface-treated or surface-crosslinked, is referred to as a "water absorbing resin powder" or a "water absorbing resin precursor" (also referred to as a base polymer), and a water absorbing resin which has been surface-treated or surface-crosslinked is referred to as "water absorbing resin particles". Further, as used in the present invention, water absorbing resins having different shapes obtained in different steps and a water absorbing resin composition containing an additive etc. are collectively referred to as a "water absorbing resin".

(1-2) "Particulate Water Absorbing Agent" and "Hardened Product"

As used in the present invention, the "particulate water absorbing agent" means a gelatinizer for an aqueous liquid, which gelatinizer contains a water absorbing resin as a main component. It should be noted that the aqueous liquid is not limited to water, and is not limited to a particular kind provided that the aqueous liquid contains water. The aqueous liquid may be urine, blood, excrement, waste fluid, moisture and vapor, ice, a mixture of water and an organic solvent and/or an inorganic solvent, rainwater, ground water or the like. Out of these, urine, particularly human urine is more preferred as the aqueous liquid.

The water absorbing resin content in a particulate water absorbing agent in accordance with the present invention is preferably between 60 wt % and 95 wt %, more preferably between 75 wt % and 94 wt %, and further preferably between 85 wt % and 93 wt %, relative to the total weight of the particulate water absorbing agent. In addition to the water absorbing resin, the particulate water absorbing agent preferably contains a polyvalent metal compound (described later), a metallic soap and/or water (5 wt % to 20 wt %). The particulate water absorbing agent preferably further contains a dispersion stabilizer, and further contains other component(s) (described later) if needed.

It should be noted that, in the present invention, the one that is obtained by adding a polyvalent metal compound, a polyvalent metal cation (water-soluble polyvalent metal salt), a metallic soap and/or water, and optionally a dispersion stabilizer to a water absorbing resin is also referred to as a "particulate water absorbing agent".

In particular, according to the following first to third embodiments and the water absorbing agent production methods 1 to 3, a water absorbing resin powder to which water only or an aqueous dispersion of a metallic soap has just been added is so-called less fluid wet powder, because the surface of the power only is wetted with water (e.g., the foregoing 3 wt % to 25 wt % of water) or is gelatinized with water. Note however that, after a certain period of time, the powder becomes fluid dry powder, as the water on the surface of the powder spreads and is absorbed into the powder. According to the present invention, after the aqueous dispersion of the metallic soap is added, the water absorbing resin powder in the wet condition may be allowed to stand for a certain period of time, heated while the moisture content is being maintained, and/or partially dried, for the purpose of accelerating the spreading of water into the powder.

It should be noted that the water absorbing resin powder (wet powder), which has entered into the wet condition by addition of water, may cause some particle aggregations as the water spreads from the surface of the particles into the particles or the water disappears and thus the surface of the particles dries. In the case where particle aggregation occurs, although it depends on the degree of aggregation, disintegration may be carried out with respect to the water absorbing resin powder having some aggregations (aggregates are subjected to an operation of mechanically crumbling aggregates) before classification. The disintegration and classification are optional, and are carried out as appropriate. A usable disintegration apparatus and a usable classification apparatus are exemplified in the granulation methods described in U.S. Pat. No. 4,734,478 and U.S. Pat. No. 5,369,148.

Further, the process in which the surfaces of particles are dried by being allowed to stand for a certain period of time or dried by heating and thus the particles lightly aggregate may be referred to as "hardening" or "hardening step" for short. Note here that the fluidity of a hardened dry water absorbing resin powder can be represented as a flow rate specified in ERT 450.2-02. A lightly-aggregated water absorbing resin powder is subjected to disintegration and classification as appropriate to make a water absorbing resin powder (particulate water absorbing agent) having preferably a flow rate of for example not more than 30 [g/sec], more preferably not more than 20 [g/sec], and not more than 15 [g/sec]. That is, the water absorbing resin powder, to which an aqueous dispersion has been added and which is in the wet condition, may be allowed to stand for a certain period of time or be heated (or dried by heating), and may further be disintegrated and classified if needed, until the flow rate falls within the above range.

To what degree the particles aggregate depends on the hardening method, and is determined as appropriate. Note however that, generally, the degree of aggregation is small if the water absorbing resin powder is stirred immediately after water only or an aqueous dispersion of a metallic soap is added, whereas all the particles aggregate into a block if the water absorbing resin powder is allowed to stand or heated without stirring. It should be noted that the water absorbing resin powder, which has not yet been hardened but to which an aqueous dispersion of a metallic soap has been added, is in the wet condition and is poor in fluidity, and the flow rate of such a water absorbing resin powder is generally unmeasurable or 300 seconds or greater. In this regard, the flow rate is not particularly limited in the present invention.

(1-3) "Particles"

As used in the present invention, the term "particles" means a powder having fluidity, preferably a powder whose flow rate (ERT 450.2-02) is measurable or a powder that can be classified by sieve classification (ERT 420.2-02). Although the "water absorbing resin powder" described in the above (1-1) is also regarded as "particles" according to such a definition, the "water absorbing resin powder" is not referred to as "particles" in the present invention for the purpose of distinguishing whether surface crosslinkage is present or not.

(1-4) "Polyacrylic Acid (Salt)"

As used in the present invention, the term "polyacrylic acid (salt)" means a polymer that optionally has a graft component and contains, as main components, recurring units constituted by an acrylic acid and/or a salt thereof (hereinafter referred to as acrylic acid (salt)). Specifically, the "polyacrylic acid (salt)" means a polymer that contains, as monomers other than a crosslinking agent, acrylic acids (salts) essentially in an amount between 50 mol % and 100 mol %, preferably in an amount between 70 mol % and 100 mol %, further preferably in an amount between 90 mol % and 100 mol %, and particularly preferably in an amount of substantially 100 mol %.

(1-5) "EDANA" and "ERT"

The term "EDANA" stands for European Disposables and Nonwovens Associations. The term "ERT" stands for EDANA Recommended Test Methods, which is the European-standard (actually, the world-standard) method of measuring water absorbing resins. In the present invention, unless otherwise noted, the measurements are carried out in conformity with the original ERT (known document: revised in 2002).

(a) "CRC" (ERT 441.2-02)

The term "CRC" stands for a centrifuge retention capacity, and means absorbency without pressure (hereinafter may be referred to as "water absorbency"). Specifically, the "CRC" is water absorbency (Unit: [g/g]) observed when 0.2 g of a water absorbing resin is allowed to freely swell in a 0.9 wt % solution of sodium chloride and thereafter water is spun off with use of a centrifugal machine.

(b) "AAP" (ERT 442.2-02)

The term "AAP" stands for absorption against pressure, and means water absorbency under pressure. Specifically, the "AAP" is water absorbency (Unit: [g/g]) observed after a water absorbing resin is allowed to swell in a 0.9 wt % solution of sodium chloride under a load of 2.06 kPa (0.3 psi) for 1 hour. It should be noted that, although this term is mentioned as "absorption under pressure" in the ERT 442.2-02, the "absorption under pressure" has substantially the same meaning as the "absorption against pressure". Further, the AAP may be measured under a condition in which the load only is changed to 4.83 kPa (0.7 psi).

(c) "Ext" (ERT 470.2-02)

The term "Ext" stands for Extractables, and means a extractable content (the amount of extractable components). Specifically, the "Ext" is a value (Unit: wt %) obtained when (i) 1 g of a water absorbing resin is added to 200 g of a 0.9 wt % solution of sodium chloride and the solution is stirred at 500 rpm for 16 hours and thereafter (ii) the amount of polymers dissolved is measured by pH titration.

(d) "PSD" (ERT 420.2-02)

The term "PSD" stands for particle size distribution, and means a particle size distribution measured by sieve classification. It should be noted that weight median particle size (D50) and the particle size distribution are measured in the same manner as in the "(1) Average Particle Diameter and Distribution of Particle Diameter" described in the pamphlet of International Publication No. WO2004/69915.

(1-6) "Surface Treatment" and "Surface Crosslinking"

As used in the present invention, a surface treatment is a superordinate concept of a surface crosslinking, and encompasses the surface crosslinking. The surface treatment encompasses: addition and mix to the surface of a water absorbing resin powder (water absorbing resin precursor, base polymer); coating the surface of the water absorbing resin powder; forming a core-shell structure by polymerizing unsaturated monomers etc.; and crosslinking the surface of a water absorbing resin with a surface crosslinking agent.

For example, the surface treatment means causing an additive to adsorb to the surface of the water absorbing resin powder (physical binding) or coating the surface of the water absorbing resin powder by adding the additive to the surface of the water absorbing resin powder. The additive is for example inorganic fine particles or a surfactant. Further, the surface treatment means a surface crosslinking, which is a subordinate concept of the surface treatment. That is, the surface treatment encompasses (i) radical crosslinking which is carried out by using a polymerization initiator in a process of polymerizing unsaturated monomers in the surface of the water absorbing resin powder, (ii) physical crosslinking (tangle of polymer chains) which is formed in the surface of the water absorbing resin powder as a result of polymerization of unsaturated monomers, and (iii) covalent bond crosslinking or ionic bond crosslinking carried out by using a surface crosslinking agent.

Further, the surface crosslinking as used in the present invention means, out of the foregoing surface treatments, (i) covalent bond crosslinking or ionic bond crosslinking carried out by using a surface crosslinking agent or (ii) crosslinking between polymer chains constituting the surface of the water absorbing resin powder, which crosslinking is caused by irradiation with activating light or a radical initiator etc.

(1-7) Other

In this Description, the phrase "X to Y", which is indicative of a range, means that "not less than X but not more than Y". Further, the term "t (ton)", which is a unit of weight, means a "metric ton". Further, unless otherwise noted, the term "ppm" means "ppm by weight", and the term "meth(acryl)" means "acryl and/or methacryl".

[2] Particulate Water Absorbing Agent of the Present Invention (First to Fourth Water Absorbing Agents)

In order to attain the foregoing objects, the present invention provides the following first to fourth water absorbing agents.

(First Water Absorbing Agent)

A particulate water absorbing agent (first water absorbing agent) in accordance with the present invention has a polyvalent metal on its surface, and satisfies the following requirements (1) through (4):

(1) a polyvalent metal cation is contained in an amount between 0.001 wt % and 5 wt % relative to the amount of the particulate water absorbing agent;

(2) an absorbency without pressure (CRC) of the particulate water absorbing agent is not less than 28 (g/g) and an absorbency against pressure (AAP 4.83 kPa) of the particulate water absorbing agent is not less than 10 (g/g);

(3) the absorbency against pressure and the absorbency without pressure satisfy the inequality: 77≤Absorbency against pressure (AAP 4.83 kPa)+1.8×Absorbency without pressure (CRC)≤100; and (4) a moisture content of the particulate water absorbing agent is between 5 wt % and 20 wt %.

(Second Water Absorbing Agent)

A particulate water absorbing agent (second water absorbing agent) in accordance with the present invention contains: water absorbing resin particles; a metallic soap (an organic salt of a polyvalent metal); water; and a dispersion stabilizer.

(Third Water Absorbing Agent)

A particulate water absorbing agent (third water absorbing agent) in accordance with the present invention contains a water absorbing resin and a metallic soap (an organic salt of a polyvalent metal), and has a moisture content of between 5 wt % and 20 wt %.

(Fourth Water Absorbing Agent)

A particulate water absorbing agent (fourth water absorbing agent) in accordance with the present invention is a particulate water absorbing agent which contains, as a main component, a surface-treated polyacrylic acid (salt) water absorbing resin, and satisfies the following requirements (2), (4) and (5):

(2) an absorbency without pressure (CRC) of the particulate water absorbing agent is not less than 28 (g/g) and an absorbency against pressure (AAP 4.83 kPa) of the particulate water absorbing agent is not less than 10 (g/g);

(5) a vertical diffusion absorbency under pressure (VDAUP) of the particulate water absorbing agent is not less than 15 g; and (4) a moisture content of the particulate water absorbing agent is between 5 wt % and 20 wt %.

Each of the second to fourth water absorbing agents preferably contains 0.001 wt % to 5 wt % of a polyvalent metal cation(s). Further, each of the second to fourth water absorbing agents is preferably configured such that the absorbency against pressure and the absorbency without pressure satisfy the inequality: 77≤Absorbency against pressure (AAP 4.83 kPa)+1.8×Absorbency without pressure (CRC)≤100.

<Further Preferable Particulate Water Absorbing Agent>

The first particulate water absorbing agent in accordance with the present invention is a water absorbing agent in which (i) a polyvalent metal is present on the surface, (ii) the amount of polyvalent metal cations relative to the amount of the water absorbing agent is between 0.001 and 5 parts by weight and the absorbency without pressure (CRC) is not less than 28 (g/g), and the absorbency against pressure (AAP 4.83 kPa) is not less than 10 (g/g), (iii) the absorbency against pressure and the absorbency without pressure satisfy the inequality: 77≤Absorbency against pressure (AAP 4.83 kPa)+1.8×Absorbency without pressure (CRC)≤100, and (iv) the moisture content is between 5 wt % and 20 wt %.

<Polyvalent Metal Cation>

The first particulate water absorbing agent in accordance with the present invention is configured such that a polyvalent metal is essentially present on the surface, and the amount of a polyvalent metal cation(s) relative to the amount of the water absorbing agent is between 0.001 wt % and 5 wt %, preferably between 0.005 wt % and 3 wt %, particularly preferably between 0.005 wt % and 2 wt %, and most preferably between 0.1 wt % and 2 wt %. Controlling the polyvalent metal present on the surface of the water absorbing agent so that the amount of the polyvalent metal cation(s) falls within the above range makes it possible to (i) achieve an optimum powder property (powder friction) and thus improve blendability with pulp etc. when the particulate water absorbing agent is used in a disposable diaper etc. and (ii) bring about an effect of improving shock resistance. If the amount of the polyvalent metal cation(s) is less than 0.001 wt %, then it is not possible to bring about the above effect. An amount of the polyvalent metal cation(s) of more than 5 wt % is not preferable, because such an amount cause a reduction in the water absorbing properties (CRC and AAP etc.). Each of the second to fourth water absorbing agents preferably contains also the foregoing amount of polyvalent metal cation(s) (polyvalent metal cation(s) derived from a metallic soap or a polyvalent metal compound). What is important for the first particulate water absorbing agent is that it contains a specific amount of polyvalent metal cation(s), and therefore a counter anion(s) of the cation(s) is not limited to a particular type. Examples of the counter anion(s) of the polyvalent metal cation(s) include anionic functional groups of a water absorbing resin. In particular, in a case of a polyacrylic acid water absorbing resin, the counter anion(s) may be carboxy anion(s). Alternatively, the counter anion(s) may be counter anion(s) of a metallic soap or of a polyvalent metal compound (described later).

It should be noted that the amount of polyvalent metal cation(s) in the particulate water absorbing agents of the first to fourth embodiments (first to fourth water absorbing agents) of the present invention can be found by fluorescent X-ray. In measuring the amount of polyvalent metal cation(s) by fluorescent X-ray, its measurement conditions etc. can be selected as appropriate. For example, the particulate water absorbing agent is subjected to pre-treatment such as pulverization and/or trituration. Further, the amount of polyvalent metal cation(s) on the surface or in a shallow surface of the particulate water absorbing agent can also be found by grinding and peeling the surfaces of particles with a grinder etc. and then measuring peeled products by fluorescent X-ray.

<CRC>

The CRC of each of the first to fourth particulate water absorbing agents of the present invention is as follows. That is, the CRC of each of the first and fourth water absorbing agents is essentially not less than 28 g/g, whereas the CRC of each of the second and third water absorbing agents and the production methods 1 to may be preferably not less than 10 (g/g), more preferably not less than 15 (g/g), not less than 18 (g/g), further preferably not less than 20 (g/g), and further more preferably not less than 25 (g/g). According to the first to fourth particulate water absorbing agents each having a CRC of not less than 28 g/g, the CRC is particularly preferably not less than 30 (g/g), and most preferably not less than 33 (g/g). The CRC is not particularly limited in its upper limit; however, the upper limit is preferably not more than 60 (g/g), more preferably not more than 50 (g/g), further preferably not more than 45 (g/g), and particularly preferably not more than 40 (g/g). Since the CRC is not less than 10 (g/g), it is possible to achieve water absorbing capacity and therefore such a particulate water absorbing agent is suitable for use in sanitary materials such as disposable diapers. Further, since the CRC is not more than 60 (g/g), it is possible to secure gel strength, and thus possible to obtain high absorbency against pressure. The CRCs are measured in the manner described in Examples.

<AAP>

The absorbency against pressure (AAP 4.83 kPa) of each of the first to fourth particulate water absorbing agents of the present invention is not less than 10 (g/g), more preferably not less than 15 (g/g), particularly preferably not less than 20 (g/g), and most preferably not less than 25 (g/g). The absorbency against pressure (AAP 4.83 kPa) is not particularly limited in its upper limit; however, in order to be balanced with the other physical properties, the upper limit is not more than 40 (g/g), and further not more than about 35 (g/g). The absorbency against pressure is measured in the manner described in Examples. Therefore, the AAPs are controlled to between 10 g/g and 40 g/g, between 15 g/g and 35 g/g, between 20 g/g and 30 g/g, between 23 g/g and 30 g/g, and between 25 g/g and 30 g/g. The AAPs can be controlled by surface crosslinking or surface treatment. This makes it possible to obtain, by each of the water absorbing agent production methods 1 to 3, a water absorbing agent which has physical properties as high as those of conventional agents and whose AAP is less reduced (substantially no reduction occurs) even though the water absorbing agent contains a polyvalent metal cation(s).

<Relation Between CRC and AAP>

Further, the CRC and the AAP are related to each other such that the "absorbency against pressure (AAP 4.83 kPa)+ 1.8× the absorbency without pressure (CRC)" is between 77 (g/g) and 100 (g/g), preferably between 77 (g/g) and 90 (g/g), and more preferably between 77 (g/g) and 85 (g/g). Controlling the CRC and the AAP so that they satisfy the above condition allows the particulate water absorbing agent to be excellent in Re-Wet and urine absorption capacity when the particulate water absorbing agent is used in an absorbent core of a disposable diaper, in particular when used in an amount between 30 wt % and 80 wt %. The CRC and the AAP out of the above range are not preferable, because desired properties of a disposable diaper such as Re-Wet may not be obtained.

For example, it is possible to obtain the first and fourth water absorbing agents by controlling, in the water absorbing agent production methods 1 to 3, the CRC and the AAP such that a particulate water absorbing agent obtained by preferably mixing thereto a polyvalent metal compound or a metallic soap (an organic salt of a polyvalent metal) satisfies the following requirements (1), (2) and (4):
(1) a polyvalent metal cation is contained in an amount between 0.001 wt % and 5 wt % relative to the amount of the particulate water absorbing agent;
(2) an absorbency without pressure (CRC) of the particulate water absorbing agent is not less than 28 (g/g) and an absorbency against pressure (AAP 4.83 kPa) of the particulate water absorbing agent is not less than 10 (g/g); and
(4) a moisture content of the particulate water absorbing agent is between 5 wt % and 20 wt %.

<Moisture Content>

The moisture content of each of the first to fourth particulate water absorbing agents of the present invention is between 5 wt % and 20 wt %, preferably between 5 wt % and 18 wt %, more preferably between 6 wt % and 18 wt %, further preferably between 7 wt % and 15 wt %, and particularly preferably between 8 wt % and 13 wt %. A moisture content of less than 5% is not preferable, because the particulate water absorbing agent becomes difficult to handle due to insufficient stability to shock and further a reduction in fluidity after moisture absorption. Further, a moisture content of more than 20 wt % is not preferable, because the water absorbing properties (AAP and CRC etc.) decrease and the fluidity after moisture absorption decreases.

It is preferable that each of the second and third water absorbing agents satisfy the above moisture content.

<Particle Size>

The particle size of each of the first to fourth particulate water absorbing agents of the present invention is as follows. That is, each of the first to fourth particulate water absorbing agents preferably includes (i) particles of not less than 106 μm but less than 850 μm in diameter in an amount between 90 wt % and 100 wt % relative to the total amount of particles and (ii) particles of not less than 300 μm in diameter in an amount of not less than 60 wt % relative to the total amount of particles.

It is more preferable that the particulate water absorbing agent contain particles of not less than 106 μm but less than 850 μm in diameter in amount of between 95 wt % and 100 wt %, and particularly between 98 wt % and 100 wt %, relative to the total amount of particles.

Further, it is preferable that the particulate water absorbing agent contain particles of not less than 300 μm in diameter in an amount between 65 wt % and 100 wt %, more preferably between 70 wt % and 100 wt %, and particularly preferably between 75 wt % and 100 wt %, relative to the total amount of particles.

Further, the weight median particle size (D50) of each of the first to fourth particulate water absorbing agents is preferably between 200 μm and 700 μm, further preferably between 300 μm and 600 μm, and particularly preferably between 400 μm and 500 μm. Further, the logarithmic standard deviation ($\sigma\zeta$), which is an index of uniformity of particle size distribution of a particulate water absorbing agent, is preferably between 0 and 0.40, more preferably between 0 and 0.35, and particularly preferably between 0 and 0.30.

If a particulate water absorbing agent contains particles of not less than 850 μm in diameter in an amount of more than 10 wt % relative to the total amount of particles, such a particulate water absorbing agent will cause discomfort in a user, e.g., cause a user a feeling of a foreign body or a feeling of roughness, when used for producing a sanitary material such as a disposable diaper. Further, if a particulate water absorbing agent contains particles of less than 106 μm in diameter in an amount of more than 10 wt % relative to the total amount of particles and/or has a logarithmic standard deviation ($\sigma\zeta$) of more than 0.40, such a particulate water absorbing agent is not preferable because many problems occur such as dramatic reductions in absorbency against pressure and fluidity after moisture absorption, deterioration in operating environments due to powder dust generated during production of sanitary materials such as disposable diapers, and an increase in segregation due to wide particle size distribution.

<VDAUP>

The inventors of the present invention found that vertical diffusion absorbency under pressure (VDAUP), which is a novel parameter indicative of a physical property, is important for disposable diapers. Specifically, there have been proposed water absorbing resins in which many physical properties such as absorbency against pressure (AAP), water absorbency (CRC) and liquid permeability (GBP, SFC) are controlled. Under the circumstances, the inventors of the present invention found out the vertical diffusion absorbency under pressure (VDAUP), which is closely correlated to physical properties of diapers and with which it is possible to evaluate properties that cannot be evaluated with use of the above parameters.

The vertical diffusion absorbency under pressure VDAUP of the fourth particulate water absorbing agent of the present invention is preferably not less than 15 g, more preferably not less than 20 g, further preferably not less than 25 g, further more preferably not less than 30 g, particularly preferably not less than 33 g, and most preferably not less than 35 g. In order to be balanced with other physical properties, the upper limit of the VDAUP is not more than 100 g, and further preferably not more than about 80 g. The vertical diffusion absorbency under pressure is measured in the manner described in Examples. In particular, a VDAUP exceeding the upper limit is not preferable, because the CRC dramatically decreases, the desired performance is not obtained, and thus such a particulate water absorbing agent is not suitable for practical use in a diaper. The above VDAUPs are suitably applicable also to the first to third water absorbing agents. A water absorbing agent satisfying the above VDAUP can be obtained by for example the production methods 1 to 3 of the present invention.

The present invention as has been described encompasses the following preferred embodiments (A) to (D).

(A) First Embodiment

Second Water Absorbing Agent

A water absorbing agent that contains a water absorbing resin, a metallic soap, water, and a dispersion stabilizer.

(B) Second Embodiment

Water Absorbing Agent Production Method 1

(i) A water absorbing agent obtained by mixing an aqueous dispersion containing a metallic soap and a dispersion stabilizer with a water absorbing resin or (ii) a particulate water absorbing agent production method including mixing an aqueous dispersion containing a metallic soap and a dispersion stabilizer with a water absorbing resin.

(C) Third Embodiment

Water Absorbing Agent Production Method 2

(i) A particulate water absorbing agent which contains a water absorbing resin and a metallic soap and has a moisture content of between 5 wt % and 20 wt % or (ii) a particulate water absorbing agent production method including: the step of adding a metallic soap and water to a water absorbing resin; and controlling the moisture content of the water absorbing agent to between 5 wt % and 20 wt %.

(D) Fourth Embodiment

Water Absorbing Agent Production Method 3

A water absorbing agent obtained by a water absorbing resin surface treatment method including the steps of: mixing an acid radical-containing radical-polymerizable monomer, a polyvalent metal compound and water with a water absorbing resin which is a polyacrylic acid (salt) crosslinked polymer; and polymerizing the acid radical-containing radical-polymerizable monomer.

According to the first to third embodiments, it is possible to cause a particulate water absorbing agent to contain a certain amount of water and have further improved absorbing properties (AAP and CRC etc.) while preventing formation of coarse particles and reducing load applied on a mixing apparatus when water is added. That is, the method of the present invention is remarkably suitable in view of continuous production, because the load applied on the mixing apparatus when water is added is dramatically reduced. Further, the method of the present invention is remarkably suitable also in view of safety and health, because, since the metallic soap is handled in the form of an aqueous dispersion, there is no problem of powder dust generation.

Note that, according to the fourth embodiment (water absorbing agent production method 3), since a surface crosslinking agent that necessitates heating at high temperatures is not essential, it is possible to carry out surface treatment at low temperatures within a short period of time. Further, the "surface-treated water absorbing resin", which is obtained by using a combination of two different surface treatment methods respectively including polymerizing a radical-polymerizable compound and carrying out ionic crosslinking of a polyvalent metal, has excellent water absorbing properties such as absorbency against pressure (AAP, VDAUP) as compared to a conventional water absorbing resin. Moreover, the surface-treated water absorbing resin obtained by the foregoing method has absorption capacity better than a conventional water absorbing resin, when in practical use in an absorbing article such as a disposable diaper.

The following description discusses, in more detail, the first to fourth embodiments each of which is a preferable embodiment of a particulate water absorbing agent of the present invention.

[3] Method of Producing Water Absorbing Resin for Use in First to Fourth Water Absorbing Agents and Water Absorbing Agent Production Methods 1 to 3

It should be noted that the following (3-1) to (3-4) of [3] describe an embodiment of a water absorbing resin powder (water absorbing resin precursor, base polymer), which is for use in the first to fourth water absorbing agents and the production methods 1 to 3.

(3-1) Polymerization Step

This step is a step of polymerizing an aqueous solution containing unsaturated monomers to obtain a hydrous gel crosslinked polymer (hereinafter referred to as a "hydrous gel").

(a) Unsaturated Monomer (Other than Crosslinking Agent)

Examples of the water absorbing resin of the present invention include: polyacrylic acid (salt) crosslinked polymers; hydrolysates of starch-acrylonitrile-grafted polymers; starch-acrylic acid-grafted polymers; saponified vinyl acetate-acrylic acid ester copolymers; hydrolysates of acrylonitrile copolymers and hydrolysates of acrylamide copolymers, and crosslinked acrylonitrile copolymers and crosslinked acrylamide copolymers; denatured crosslinked polyvinyl alcohols each having a carboxyl group; and isobutylene-maleic anhydride crosslinked copolymers. These water absorbing resins may be used solely or two or more water absorbing resins can be used in combination. That is, an unsaturated monomer for use in obtaining the water absorbing resin particles in accordance with the present invention may be any monomer, provided that it is possible to achieve desired physical properties. It should be noted that, in view of physical properties of the water absorbing resin particles to be obtained, it is particularly preferable to use a polyacrylic acid (salt) crosslinked polymer (also referred to as a polyacrylic acid (salt) water absorbing resin) as the water absorbing resin.

In a case where the polyacrylic acid (salt) crosslinked polymer is to be used, an acrylic acid (salt) (which is an unsaturated monomer) may be used as a main component. In addition, a monomer other than the acrylic acid (salt) (such a monomer is hereinafter referred to as "the other monomer") may be used as a copolymerization component. This makes it possible to impart properties (e.g., anti-bacterial property and deodorant property) other than the water absorbing property to a final particulate water absorbing agent, and also makes it possible to produce the particulate water absorbing agent at lower costs. Such a polyacrylic acid (salt) water absorbing resin optionally has a graft component (e.g., starch, polyvinyl alcohol) in an amount between 0 wt % and 50 wt %, and further preferably in an amount between 0 wt % and 40 wt %. Such a graft polymer and the foregoing polyacrylic acid (salt) crosslinked polymer are collectively referred to as a polyacrylic acid (salt) water absorbing resin.

The foregoing other monomer is not particularly limited. Examples of the other monomer include water-soluble unsaturated monomers and hydrophobic unsaturated monomers such as methacrylic acid, maleic acid (anhydride), fumaric acid, crotonic acid, itaconic acid, vinyl sulfonic acid, 2-(meth)acrylamide-2-methylpropanesulfonic acid, (meth)acryloxy alkane sulfonic acid and its alkali metal salt and its ammonium salt, N-vinyl-2-pyrrolidone, N-vinylacetamide, (meth)acrylamide, N-isopropyl (meth)acrylamide, N,N-dimethyl (meth)acrylamide, 2-hydroxyethyl (meth)acrylate, methoxy polyethylene glycol (meth)acrylate, polyethylene glycol (meth)acrylate, isobutylene, and lauryl (meth)acrylate.

Further, the amount of the other monomer to be used is between 0 mol % and 50 mol %, preferably between 0 mol % and 30 mol %, more preferably between 0 mol % and 10 mol %, and further preferably between 0 mol % and 5 mol %, relative to the total number of moles of unsaturated monomers. In other words, the amount of the acrylic acid (salt) serving as a main component is preferably between 70 mol % and 100 mol %, more preferably between 90 mol % and 100 mol %, and further preferably between 95 mol % and 100 mol %. Note however that, in view of water absorbing properties (e.g., AAP) of the particulate water absorbing agent to be obtained, it is most preferable that the amount of the acrylic acid (salt) be substantially 100 mol %.

In a case where a monomer having an acid radical is used as an unsaturated monomer (including the other monomer), an alkali metal salt, an alkali earth metal salt, and/or an ammonium salt may be used as a salt of the unsaturated monomer. Out of these, in view of properties of the particulate water absorbing agent to be obtained, availability in industry of the unsaturated monomer salt and safety etc., a monovalent salt is preferable, and a monovalent metal salt is particularly preferable. Out of these, a sodium salt or a potassium salt is preferable.

Further, in a case where an acrylic acid (salt) is used as an unsaturated monomer, the ratio of an acrylic acid to an acrylic acid salt is preferably 0 mol %-50 mol % to 100 mol %-50 mol % (provided that a sum of the acrylic acid and acrylic acid salt is not more than 100 mol %), and is more preferably 10 mol %-40 mol % to 90 mol %-60 mol %. That is, the "degree of neutralization", which is a molar ratio of an acrylic acid salt to the total amount of the acrylic acid and the acrylic acid salt, is preferably between 50 mol % and 100 mol %, and more preferably between 60 mol % and 90 mol %.

The acrylic acid salt is produced for example by (i) neutralizing an acrylic acid in the form of a monomer before polymerization, (ii) neutralizing the acrylic acid in the form of a polymer during or after polymerization, or (iii) carrying out a combination of the foregoing (i) and (ii). Further, it is possible to produce an acrylic acid (salt) by mixing an acrylic acid and an acrylic acid salt.

(b) Internal Crosslinking Agent

The water absorbing resin in accordance with the present invention can be regarded as having an internal crosslinked structure, provided that the water absorbing resin is water-swelling and water-insoluble as described in the foregoing (1-1). Therefore, the water absorbing resin may be the one obtained by self-crosslinking of unsaturated monomers without using an internal crosslinking agent. Note, however, that the water absorbing resin is preferably the one obtained by copolymerizing or reacting unsaturated monomers with an internal crosslinking agent. Examples of the internal crosslinking agent include the one having two or more unsaturated polymerizable groups or two or more reactive groups per molecule.

Specific examples of the internal crosslinking agent include: N,N'-methylenebis (meth)acrylamide, (poly)ethyleneglycol di(meth)acrylate, (poly)propyleneglycol di(meth)acrylate, trimethylolpropane tri(meth)acrylate, glycerin tri (meth)acrylate, glycerin acrylate methacrylate, ethyleneoxide-denatured trimethylolpropane tri(meth)acrylate, pentaerythritol hexa(meth)acrylate, triallyl cyanurate, triallyl isocyanurate, triallyl phosphate, triallyl amine, poly (meth)allyloxy alkane, (poly)ethyleneglycol diglycidyl ether, glycerol diglycidyl ether, ethylene glycol, polyethylene glycol, propylene glycol, glycerin, pentaerythritol, ethylenediamine, ethylene carbonate, propylene carbonate, polyethyleneimine, and glycidyl (meth)acrylate.

These internal crosslinking agents may be used solely or two or more internal crosslinking agents may be mixed to be used in combination as appropriate. Further, the internal crosslinking agent may be added to a reaction system all at once or may be added in several batches. Further, in view of water absorbing properties etc. of the finished particulate water absorbing agent, it is preferable to use, when carrying out polymerization, an internal crosslinking agent having two or more unsaturated polymerizable groups.

In view of obtaining good physical properties of the water absorbing resin, the amount of the internal crosslinking agent to be used is preferably between 0.001 mol % and 2 mol %, more preferably between 0.005 mol % and 0.5 mol %, further preferably between 0.01 mol % and 0.2 mol %, and particularly preferably between 0.03 mol % and 0.15 mol %, relative to the amount of monomers other than the crosslinking agent. An amount of the internal crosslinking agent of less than 0.001 mol % or more than 2 mol % is not preferable, because it may be impossible to obtain sufficient water absorbing properties of the water absorbing resin.

In a case where an internal crosslinked structure is to be introduced into the water absorbing resin with use of the internal crosslinking agent, the internal crosslinking agent may be added to a reaction system before, during or after polymerization of the unsaturated monomers or after neutralization of the unsaturated monomers.

(c) Polymerization Initiator

A polymerization initiator for use in the polymerization step is selected appropriately depending on the type of polymerization, and is not particularly limited. Examples of the polymerization initiator include photodegradable polymerization initiators, pyrolytic polymerization initiators, and redox polymerization initiators.

Examples of the photodegradable polymerization initiators include benzoin derivatives, benzyl derivatives, acetophenone derivatives, benzophenone derivatives and azo compounds. Examples of the pyrolytic polymerization initiators include persulfates (sodium persulfate, potassium persulfate, and ammonium persulfate), peroxides (hydrogen peroxide, t-butyl peroxide, methyl-ethyl-ketone peroxide), and azo compounds (2,2'-azobis (2-amidinopropane)dihydrochloride, 2,2'-azobis[2-(2-imidazoline 2-yl)propane]dihydrochloride). Examples of the redox polymerization initiators include systems each of which is a combination of (i) a reducing compound such as L-ascorbic acid or sodium hydrogen sulfite and (ii) the foregoing persulfate or peroxide. Further, it is also a preferable embodiment to use the combination of a photodegradable polymerization initiator and a pyrolytic polymerization initiator.

The amount of the polymerization initiator to be used is preferably between 0.001 mol % and 2 mol %, and more preferably between 0.01 mol % and 0.1 mol %, relative to the amount of the monomers. An amount of the polymerization initiator of more than 2 mol % is not preferable, because this makes it difficult to control polymerization. Further, an amount of the polymerization initiator less than 0.001 mol % is not preferable, because the residual monomer content may increase.

(d) Polymerization Method

According to the foregoing polymerization step, it is possible to carry out bulk polymerization or precipitation polymerization to polymerize the unsaturated monomers. Note however that, in view of properties of the water absorbing resin to be obtained, polymerization controllability and water absorbing properties of a hydrous gel etc., it is preferable to employ aqueous polymerization or reversed phase suspension polymerization, each of which is carried out by using an aqueous solution of unsaturated monomers. Note that the unsaturated monomers encompass also the foregoing other monomer and the internal crosslinking agent.

In a case of preparing the aqueous solution of unsaturated monomers, the concentration of monomers in the aqueous solution is determined in consideration of the temperature of the aqueous solution or the type of monomers, and is not particularly limited. The concentration is preferably between 10 wt % and 70 wt %, and more preferably between 20 wt % and 60 wt %.

Polymerization of unsaturated monomers is initiated by (i) addition of a polymerization initiator, (ii) irradiation with activating light such as an ultraviolet ray, an electron ray or a gamma ray or (iii) a combination of the foregoing (i) and (ii). A reaction temperature in the polymerization reaction may be selected as appropriate depending on a polymerization initiator to be used or the type of activating light to be used, and is not particularly limited. The reaction temperature is preferably between 15° C. and 130° C., and more preferably between 20° C. and 120° C. A reaction temperature outside the above range is not preferable, because the residual monomer content in the water absorbing resin to be obtained may increase and/or self-crosslinking reaction may proceed excessively, and thus the water absorbing properties of the water absorbing resin may decrease.

It should be noted that the reversed phase suspension polymerization is a method of carrying out polymerization by suspending a monomer aqueous solution in a hydrophobic organic solvent. Such reversed phase suspension polymerization is disclosed in for example U.S. Pat. No. 4,093,776, U.S. Pat. No. 4,367,323, U.S. Pat. No. 4,446,261, U.S. Pat. No. 4,683,274, and U.S. Pat. No. 5,244,735.

Further, the aqueous polymerization is a method of polymerizing a monomer aqueous solution without using a dispersion solvent. Such aqueous polymerization is disclosed in for example U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, U.S. Pat. No. 5,380,808 and the like, and European Patent No. 0811636, European Patent No. 0955086, European Patent No. 0922717, and the like. Note that, if needed, a solvent other than water may be used in combination. The type etc. of solvent is not particularly limited.

That is, by applying the foregoing unsaturated monomers or the polymerization initiator etc. to the polymerization method disclosed in the foregoing patent literatures, it is possible to obtain a water absorbing resin in accordance with the present invention.

(3-2) Drying Step

This step is a step of drying a hydrous gel crosslinked polymer (hydrous gel) obtained in the polymerization step. Note that, in a case where the polymerization step employs aqueous polymerization, pulverization is usually carried out before and/or after the hydrous gel is dried.

The drying step is not particularly limited provided that the drying step achieves a desired moisture content, and therefore can employ a variety of methods. Specifically, the drying step may employ drying by heating, hot-air drying, drying under reduced pressure, infrared drying, microwave drying, azeotropic dehydration with a hydrophobic organic solvent, high humidity drying with use of high-temperature vapor and/or the like. Out of these, in a case where the hot-air drying is employed, the temperature of the hot air is usually between 60° C. and 250° C., preferably between 100° C. and 220° C., and more preferably between 120° C. and 200° C. Further, a drying time depends on the surface area of and the moisture content in the hydrous gel, and the type of drying apparatus. Therefore, the drying time may be selected as appropriated for example within a range of 1 minute to 5 hours so that a desired moisture content is achieved.

It should be noted that a hydrous gel obtained by reversed phase suspension polymerization can be dried in the following manner, without carrying out any pulverization. For example, a hydrocarbon organic solvent such as a hexane, in which a hydrous gel is dispersed, is subjected to azeotropic dehydration so that the moisture content of the hydrous gel is not more than 40 wt % and preferably not more than 30 wt %. After that, the organic solvent and the hydrous gel are separated from each other by decantation or evaporation to obtain a water absorbing resin in accordance with the present invention. Even in this case, a drying step may further be carried out if needed. Note that, during the foregoing drying steps, it is possible to carry out surface crosslinking simultaneously with drying.

The moisture content [wt %] after the drying step is calculated from loss on drying (1 g of powder or particles is heated at 180° C. for 3 hours). The solid content (100-Moisture content) of a dried resin is controlled to be preferably not less than 80 wt %, more preferably between 85 wt % and 99 wt %, and further preferably between 90 wt % and 98 wt %. In this way, it is possible to a dried polymer.

(3-3) Pulverization Step, Classification Step

This step is a step of pulverizing and/or classifying a dried polymer obtained in the drying step to obtain a water absorbing resin powder. A water absorbing resin obtained after a pulverization step may be referred to as a pulverized resin.

It should be noted that, in the case of the reversed phase suspension polymerization, the pulverization step is carried out optionally because the particle size is controlled during dispersion polymerization. Note, however, that pulverization or disintegration of aggregates (operation of crumbling aggregates) may be carried out if needed. Also in the case of the aqueous polymerization, it is possible to omit the pulverization step after drying, depending on the degree of crush of the gel during or after polymerization. Note, however, that it is preferable to further carry out pulverization and classification.

That is, although a dried polymer obtained in the drying step may be directly used as a water absorbing resin powder, the dried polymer is preferably controlled to have a specific particle size by preferably being pulverized and classified so as to obtain a particulate water absorbing agent of the present invention. The control of the particle size can be carried out not only in the pulverization step and the classification step, but also in the polymerization step, a fine powder collection step, a granulation step, or the like. In the following, the particle size is specified by use of a JIS standard sieve (JIS Z8801-1 (2000)).

(3-4) Surface Crosslinking Step

As has been described, crosslinking polymerization and drying are carried out, and if needed, pulverization is carried out to obtain a water absorbing resin powder in accordance with the present invention. It is preferable that the surface of the water absorbing resin powder be further subjected to crosslinking (secondary crosslinking) to obtain water absorbing resin particles. This increases the crosslink density in the shallow surface so as to improve various physical properties of the water absorbing resin powder.

The following description discusses surface treatment composition (material for surface crosslinking) suitably used in the water absorbing agent production methods 1 and 2. Note that, although the production method 3 (described later) of the present invention employs surface polymerization as the surface treatment, the production method 3 may further employ the surface crosslinking, optionally.

According to the water absorbing agent production methods 1 and 2 (and further the water absorbing agent production method 3), a surface crosslinking agent for use in the surface crosslinking step is not particularly limited provided that good physical properties of the resulting water absorbing resin particles are achieved. Examples of the surface crosslinking agent include polyhydric alcohol compounds, epoxy compounds, polyhydric amine compounds, condensates of a polyhydric amine compound and a haloepoxy compound, oxazoline compounds, monooxazolidinone compounds, dioxazolidinone compounds, polyoxazolidinone compounds, polyvalent metal salts, and alkylene carbonate compounds. It is preferable that these surface crosslinking agents be used solely or two or more surface crosslinking agents be used in combination.

More specifically, it is possible to use the surface crosslinking agent disclosed in U.S. Pat. No. 6,228,930, U.S. Pat. No. 6,071,976, or U.S. Pat. No. 6,254,990 etc. That is, examples of the surface crosslinking agent include: polyhydric alcohol compounds such as monoethylene glycol, diethylene glycol, triethylene glycol, tetraethylene glycol, polyethylene glycol, monopropylene glycol, 1,3-propanediol, dipropylene glycol, 2,3,4-trimethyl-1,3-pentanediol, polypropylene glycol, glycerin, polyglycerin, 2-butene-1,4-diol, 1,4-butanediol, 1,3-butanediol, 1,5-pentanediol, 1,6-hexanediol, and 1,2-cyclohexane dimethanol; epoxy compounds such as ethylene glycol diglycidyl ether and glycidol; polyhydric amine compounds such as ethylenediamine, diethylenetriamine, triethylenetetramine, tetraethylenepentamine, pent a ethylene hex amine, polyethyleneimine, and polyamide polyamine; haloepoxy compounds such as epichlorohydrin, epibromohydrin and alpha-methylepichlorohydrin; condensates of a polyhydric amine compound and a haloepoxy compound; oxazolidinone compounds such as 2-oxazolidinone; and alkylene carbonate compounds such as ethylene carbonate.

Further, an ionic bond surface crosslinking agent, a polyvalent metal salt and/or a polyamine polymer may be used in addition to the foregoing surface crosslinking agent. Furthermore, an inorganic surface crosslinking agent may be used in addition to the foregoing organic surface crosslinking agent to improve liquid permeability etc. of the water absorbing agent. Examples of the inorganic surface crosslinking agent to be used include salts (organic salts or inorganic salts) of bivalent or multivalent, and preferably trivalent or tetravalent metals; and hydroxides of bivalent or multivalent, and preferably trivalent or tetravalent metals. Examples of usable polyvalent metals include aluminum and zirconium, and aluminum lactate and aluminum sulfate.

The inorganic surface crosslinking agent and the organic surface crosslinking agent are used simultaneously with or separately from each other. Surface crosslinking using a polyvalent metal is exemplified in International Publication No. 2007/121037, International Publication No. 2008/09843, International Publication No. 2008/09842, U.S. Pat. No. 7,157,141, U.S. Pat. No. 6,605,673, U.S. Pat. No. 6,620,889, US Patent Application Publication No. 2005/0288182, US Patent Application Publication No. 2005/0070671, US Patent Application Publication No. 2007/0106013, and US Patent Application Publication No. 2006/0073969, etc.

Further, in addition to the organic surface crosslinking agent, a polyamine polymer, particularly a polyamine polymer having an weight-average molecular weight of 5000 to 1,000,000, may be added simultaneously with or separately from the organic surface crosslinking agent to improve liquid permeability etc of the water absorbing agent. The polyamine polymer to be used is exemplified in for example U.S. Pat. No. 7,098,284, International Publication No. 2006/082188, International Publication No. 2006/082189, International Publication No. 2006/082197, International Publication No. 2006/111402, International Publication No. 2006/111403, and International Publication No. 2006/111404 etc.

Out of these surface crosslinking agents, in order to improve various properties of water absorbing resin particles as much as possible, it is preferable to use a covalent bond surface crosslinking agent. Further, in order to prevent a reduction in moisture content during surface treatment (to improve stability to shock of water absorbing resin particles), it is preferable to use an epoxy compound, a haloepoxy compound or an oxazolidinone compound which can react even at low temperatures, and further preferable to use at least an epoxy compound or a haloepoxy compound.

It should be noted that, in a case where the surface crosslinking is carried out at high temperatures with use of a dehydration-reactive surface crosslinking agent selected from alkylene carbonates and polyhydric alcohols, the moisture content is controlled so as to fall within the range (described later) by further adding water as appropriate after the surface crosslinking. In a case where a polyhydric alcohol is used as the dehydration-reactive surface crosslinking agent, the polyhydric alcohol is a $C_2$-$C_{10}$ polyhydric alcohol, and preferably a $C_3$-$C_8$ polyhydric alcohol.

The amount of the surface crosslinking agent to be used depends on (i) the type of surface crosslinking agent to be used and (ii) a combination of a water absorbing resin precursor and a surface crosslinking agent etc. Note, however, that the amount of the surface crosslinking agent is preferably between 0.001 and 10 parts by weight, and more preferably between 0.01 and 5 parts by weight, relative to 100 parts by weight of the water absorbing resin powder.

When carrying out the surface crosslinking, it is preferable to use water in combination with the surface crosslinking agent. The amount of water to be used here depends on the moisture content of the water absorbing resin powder to be used. Note however that, usually, the amount of water to be used is between 0.5 and 20 parts by weight, and preferably between 0.5 and 10 parts by weight, relative to 100 parts by weight of the water absorbing resin powder.

When the surface crosslinking agent or an aqueous solution of the surface crosslinking agent is to be mixed, a hydrophilic organic solvent or a third material may be used as a mixing auxiliary agent.

In a case of using a hydrophilic organic solvent, examples of such a hydrophilic organic solvent include: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and methoxy (poly)ethylene glycol; amides such as epsilon-caprolactam and N,N-dimethylformamide; sulfoxides such as dimethyl sulfoxide; and polyhydric alcohols such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,3-butanediol, 1,4-butanediol, 1,5-pentanediol, 1,6-hexanediol, 1,2-cyclohexane dimethanol, 1,2-cyclohexanol, trimethylolpropane, diethanolamine, triethanolamine, polyoxypropylene, oxyethylene-oxypropylene block copolymers, pentaerythritol, and sorbitol.

It should be noted that a polyhydric alcohol is categorized as a surface crosslinking agent under the condition where it reacts with a water absorbing resin, whereas it is categorized as a hydrophilic organic solvent under the condition where it does not react with the water absorbing resin. Whether the polyhydric alcohol has reacted with the water absorbing resin or not can be easily determined on the basis of the remaining amount of the polyhydric alcohol or an increase in ester (e.g., IR analysis).

The amount of the hydrophilic organic solvent to be used depends on the type, particle size and moisture content etc. of the water absorbing resin powder. The amount of the hydrophilic organic solvent to be used is preferably not more than 10 parts by weight, and more preferably between 0.1 and 5 parts by weight, relative to 100 parts by weight of the solid content of the water absorbing resin powder. Further, an inorganic acid, organic acid and/or polyamino acid etc. shown in the specification of European Patent No. 0668080 may be caused to exist as a third material. Each of these mixing auxiliary agents may be caused to serve as a surface crosslinking agent, but is preferably the one that does not cause a reduction in water absorbing properties of surface-crosslinked water absorbing resin particles. In particular, volatile alcohols each having a boiling point of lower than 150° C. are preferable, because the volatile alcohols evaporate during the surface crosslinking and therefore no residue will remain.

For the purpose of mixing the water absorbing resin powder and the surface crosslinking agent more evenly, non-crosslinkable, water-soluble inorganic salts (preferably an alkali metal salt, an ammonium salt, a hydroxide of an alkali metal, and ammonia or a hydroxide of ammonia) or an irreducible-alkali-metal-salt pH buffer (preferably bicarbonate, dihydrogen phosphate, hydrogen phosphate etc.) may be caused to coexist when the water absorbing resin powder and the surface crosslinking agent are mixed with each other. The amount of a non-crosslinkable, water-soluble inorganic salt or an irreducible-alkali-metal-salt pH buffer to be used depends on the type and particle size etc. of the water absorbing resin powder, but is preferably between 0.005 and 10 parts by weight, and more preferably between 0.05 and 5 parts by weight, relative to 100 parts by weight of the solid content of the water absorbing resin powder.

(How to Add Surface Crosslinking Agent)

The surface crosslinking agent can be added by various methods. For example, in a case where the water absorbing resin powder is obtained by aqueous polymerization, it is preferable to (i) if needed, mix the surface crosslinking agent with water and/or with a hydrophilic organic solvent in advance during or after the drying step and (ii) mix the surface crosslinking agent dropwise to the water absorbing resin powder. It is more preferable to spray the surface crosslinking agent to the water absorbing resin powder. The size of droplets to be sprayed is preferably between 0.1 µm and 300 µm, and more preferably between 1 µm and 200 µm, in a mean diameter of droplets.

In order to evenly and thoroughly mix the water absorbing resin powder, the surface crosslinking agent, water and/or the hydrophilic organic solvent, a mixing apparatus to be used to mix these compounds is preferably the one that has high mixing power. Preferable examples of such a mixing apparatus include: cylindrical mixers, double-wall conical mixers, high-speed stirring mixers, V-shaped mixers, ribbon mixers, screw type mixers, double-arm kneaders, pulverizing type kneaders, rotating mixers, air mixers, Turbulizer, batch-type Loedige mixers, and continuous-type Loedige mixers.

After the surface crosslinking agent and the water absorbing resin powder are mixed with each other, the mixture is preferably subjected to heat treatment. The heat treatment is carried out under the condition where the temperature of the water absorbing resin powder or the temperature of a heat medium used in the heat treatment is preferably between 60° C. and 250° C., more preferably between 60° C. and 150° C., and further preferably between 80° C. and 120° C. Further, a heating time for the heat treatment is preferably between 1 minute and 2 hours. Examples of a preferable combination of the heating temperature and the heating time include: 180° C. and 0.1 to 1.5 hours; and 100° C. and 0.1 to 1 hour.

It should be noted that, in a case where an alkylene carbonate or a polyhydric alcohol is used as the surface crosslinking agent, the temperature of the water absorbing resin powder or the temperature of the heat medium to be used in the heat treatment is preferably between 100° C. and 250° C., more preferably between 150° C. and 250° C., and further preferably between 170° C. and 210° C. In the case where an alkylene carbonate or a polyhydric alcohol is used as the surface crosslinking agent and is heated at a temperature falling within the above range, the moisture content is controlled, after the surface crosslinking, to the moisture content (described later) of the particulate water absorbing agent.

In a case where the water absorbing resin powder is obtained by reversed phase suspension polymerization, it is possible to obtain surface-crosslinked water absorbing resin particles in the following manner. That is, the surface crosslinking agent, preferably a glycidyl ether compound is dispersed in a hydrophobic organic solvent used in the reversed phase suspension polymerization, for example during azeotropic dehydration and/or after completion of the azeotropic dehydration after completion of the polymerization. That is, the surface crosslinking agent is dispersed in the hydrophobic organic solvent for example when the moisture content of the hydrous gel is not more than 50 wt %, preferably not more than 40 wt %, and more preferably not more than 30 wt % (the lower limit is preferably not less than 5 wt %, further preferably not less than 10 wt %, and particularly preferably not less than 15 wt %).

(Moisture Content after Surface Crosslinkings)

According to these surface crosslinkings, in particular a surface crosslinking using a dehydration-reactive surface crosslinking agent (dehydration-reactive crosslinking agent) or a high-temperature surface crosslinking (e.g., at a temperature between 150° C. and 250° C.), a resulting water absorbing resin will have excellent physical properties (in particular, AAP 4.83 kPa is excellent). However, the water present in the water absorbing resin after the drying step and the water added to the water absorbing resin as a solvent for the crosslinking agent will be mostly removed. Accordingly, the moisture content of the water absorbing resin after the surface crosslinking reaction is usually as low as 0 wt % to 5 wt %, 0 wt % to 3 wt %, or 0 wt % to 1 wt %. That is, (i) excellent physical properties that generally necessitate high-temperature surface treatment and (ii) high moisture content are in a trade-off relationship.

For this reason, although there has been proposed a conventional technique of adding water after the high-temperature treatment of the surface, it has been difficult to produce a water absorbing agent stably in production processes.

That is, such a water absorbing resin having a low moisture content has a problem of stability to shock. In view of this, there have been proposed techniques of adding an approximately several percentage of water to a surface-crosslinked water absorbing resin (Patent Literatures 15 to 20). However, such techniques have (i) a problem in which particles stick to one another when water is added, and as the amount of water added is increased, a higher load is applied on a mixer and thereby the mixer often stops operating and (ii) a problem in which adding a mixing auxiliary agent (e.g., inorganic salt) causes a reduction in physical properties (e.g., absorbency against pressure) of the water absorbing resin. In order to solve such problems, a production method of the present invention includes adding water in the form of an aqueous dispersion of a metallic soap so that the water absorbing resin have a predetermined moisture content (between 5 wt % and 20 wt %). As such, the present invention is preferable because, even if water is added to a surface-crosslinked water absorbing resin having a low moisture content (between 0 wt % and 5 wt %, between 0 wt % and 3 wt %, between 0 wt % and 1 wt %), the physical properties after surface crosslinking are not reduced substantially.

[4] Preferable Physical Properties of Water Absorbing Resin Particles in Water Absorbing Agent Production Methods 1 to 3

It is preferable to obtain the first to fourth water absorbing agents of the present invention by the water absorbing agent production methods 1 to 3 using water absorbing resin particles having the following physical properties, in particular by the production methods 1 and 2 in which the water absorbing resin particles are surface-crosslinked so as to have the following physical properties.

(4-1) Particle Size

Water absorbing resin particles in accordance with the present invention, which are obtained by being subjected to a surface crosslinking as appropriate, are controlled to have a certain particle size in order to secure fluidity after moisture absorption and to suppress a reduction in water absorbing properties and a reduction in fluidity after moisture absorption caused by mechanical shock. Specifically, the water absorbing resin particles are controlled to have a weight median particle size (D50) of preferably between 200 µm and 700 µm, more preferably between 300 µm and 600 µm, and further preferably between 400 µm and 500 µm.

Further, the particulate water absorbing agent of the present invention preferably contains particles of not less than 106 µm but less than 850 µm in diameter in an amount between 90 wt % and 100 wt %, more preferably between 95 wt % and 100 wt %, and further preferably between 98 wt % and 100 wt %, relative to the total amount of water absorbing resin particles contained in the particulate water absorbing agent. Furthermore, the particulate water absorbing agent preferably contains particles of not less than 300 µm in diameter in an amount between 60 wt % and 100 wt %, more preferably between 65 wt % and 100 wt %, further preferably between 70 wt % and 100 wt %, and particularly preferably between 75 wt % and 100 wt %. Moreover, as to particle size distribution of the water absorbing resin particles, logarithmic standard deviation ($\sigma\zeta$), which is an index indicative of uniformity, is preferably between 0 and 0.40, more preferably between 0 and 0.35, and most preferably between 0 and 0.30.

Therefore, if the amount of water absorbing resin particles of not less than 850 µm in diameter is more than 10 wt % relative to the total amount of the water absorbing resin particles contained in the particulate water absorbing agent, such a particulate water absorbing agent is not preferable because it will cause discomfort in a user, e.g., cause a user a feeling of a foreign body or a feeling of roughness, when used in a sanitary material such as a disposable diaper. Further, if the amount of water absorbing particles of less than 106 µm in diameter is more than 10 wt % relative to the total amount of water absorbing resin particles contained in the particulate water absorbing agent and/or the logarithmic standard deviation ($\sigma\zeta$) is more than 0.40, such a particulate water absorbing agent is not preferable because many problems occur such as a dramatic reduction in absorbency against pressure and a reduction in fluidity after moisture absorption, deterioration in operating environments due to powder dust generation, and an increase in segregation due to wide particle size distribution.

It should be noted that the weight median particle size (D50) and the amount of particles having a certain particle size can be controlled as appropriate by controlling the particle size of a water absorbing resin which has not yet been surface-treated during the polymerization step (particularly reversed phase suspension polymerization), the pulverization and classification steps, the granulation step or the fine powder collection step etc. A surface-treated water absorbing resin may also be subjected to a disintegration step (step of crumbling aggregates formed during surface treatment), a particle sizing step (classifying with use of a sieve or blending particle components having different particle sizes), granulation step and/or fine powder collection step etc. as appropriate so as to have a predetermined amount of particles having a certain particle size. The control to obtain a predetermined particle size is for example carried out by any of the steps described in US Patent Application Publication No. 2004/181031, US Patent Application Publication No. 2004/242761, and US Patent Application Publication No. 2006/247351 etc.

(4-2) CRC

Water absorbing resin particles in accordance with the present invention have a centrifugal retention capacity (CRC) of preferably not less than 10 [g/g], more preferably not less than 15 [g/g], further preferably not less than 25 [g/g], particularly preferably not less than 28 [g/g], more particularly preferably not less than 30 [g/g], and most preferably not less than 33 [g/g]. The upper limit of the CRC is not particularly limited, but is preferably not more than 60 [g/g], more preferably not more than 50 [g/g], further preferably not more than 45 [g/g], and particularly preferably not more than 40 [g/g]. If the centrifugal retention capacity (CRC) is less than 10 [g/g], water absorbing capacity is too small and such water absorbing resin particles are not suitable for use in a sanitary material such as a disposable diaper. On the other hand, if the centrifugal retention capacity (CRC) is more than 60 [g/g], it may be impossible to obtain a particulate water absorbing agent that is excellent in rate of liquid absorption into an absorbent core when the particulate water absorbing agent is used in the absorbent core. Note that, according to the present invention, in a case where the first or fourth water absorbing agent whose CRC is also not less than 28 [g/g] is to be obtained, usually, a water absorbing resin also having a CRC of not less than 28 [g/g] is selected as appropriate.

(4-3) AAP 4.83 kPa

Water absorbing resin particles in accordance with the present invention have an absorbency under a pressure (load) of 4.83 kPa (AAP 4.83 kPa) of not less than 10 [g/g], preferably not less than 15 [g/g], more preferably not less than 18 [g/g], further preferably not less than 20 [g/g], further preferably not less than 25 [g/g], particularly preferably not less than 28 [g/g], and most preferably not less than 30 [g/g].

Such an AAP can be achieved by for example surface-crosslinking the water absorbing resin particles having the foregoing particle size, in particular, by surface-crosslinking the water absorbing resin particles so as to control the CRC to a predetermined CRC. Note, however, that this does not imply any limitation.

(4-4) Moisture Content

The moisture content of a water absorbing resin (water absorbing resin precursor, base polymer, surface-crosslinked water absorbing resin particles) in accordance with the present invention is not particularly limited. Note however that, in order to obtain a powder having fluidity even at room temperature so as to obtain a particulate water absorbing agent of the present invention, it is preferable to control the moisture content. Accordingly, the moisture content of the water absorbing resin particles is more than 0 wt % but not more than 20 wt %, preferably more than 0 wt % but not more than 10 wt %, more preferably between 0.1 wt % and 7 wt %, and particularly preferably between 0.1 wt % and 5 wt %. The moisture content of the surface-crosslinked water absorbing resin particles is between 0 wt % and 5 wt %, more preferably between 0 wt % and 3 wt %, and particularly preferably between 0 wt % and 1 wt %.

It should be noted that the moisture content of a particulate water absorbing agent (third water absorbing agent) of the present invention obtained by the water absorbing agent production method 1 or 2, i.e., the moisture content of a particulate water absorbing agent obtained by adding a metallic soap to water absorbing resin particles, falls within a predetermined range. That is, the moisture content of the particulate water absorbing agent is between 5 wt % and 20 wt %, preferably between 5 wt % and 18 wt %, and more preferably between 6 wt % and 18 wt % (this is described later).

Further, the moisture content of a particulate water absorbing agent (fourth water absorbing agent) of the present invention obtained by the water absorbing agent production method 3 also falls within a predetermined range. That is, the moisture content of the particulate water absorbing agent is between 5 wt % and 20 wt %, preferably between 5 wt % and 18 wt %, and more preferably between 6 wt % and 18 wt %.

How to control the moisture content of a particulate water absorbing agent of the present invention so that the moisture content falls within a predetermined range is also described later.

[5] Particulate Water Absorbing Agent Production Methods Related to First to Fourth Water Absorbing Agents (a) Production Methods
(Water Absorbing Agent Production Method 1)

A method of producing a particulate water absorbing agent (water absorbing agent production method 1) of the present invention includes mixing an aqueous dispersion containing a metallic soap (an organic salt of a polyvalent metal) and a dispersion stabilizer with a water absorbing resin.

(Water Absorbing Agent Production Method 2)

A method of producing a particulate water absorbing agent (water absorbing agent production method 2) of the present invention includes the steps of adding a metallic soap (an organic salt of a polyvalent metal) and water to a water absorbing resin and controlling a moisture content of the particulate water absorbing agent to between 5 wt % and 20 wt %.

(Second Water Absorbing Agent)

A particulate water absorbing agent (second water absorbing agent) of the present invention includes: water absorbing resin particles; a metallic soap (an organic salt of a polyvalent metal); water; and a dispersion stabilizer.

(Third Water Absorbing Agent)

A particulate water absorbing agent (third water absorbing agent) of the present invention include: a water absorbing resin and a metallic soap (an organic salt of a polyvalent metal), and has a moisture content of between 5 wt % and 20 wt %.

A method of producing each of the water absorbing agents is not limited to the above production methods. For example, each of the water absorbing agents can be obtained by the production methods 1 to 3. That is, the second water absorbing agent can be obtained by for example the water absorbing agent production method 1. The third water absorbing agent can be obtained by for example the water absorbing agent production method 2.

Further, each of the first and fourth water absorbing agents can be obtained by for example the water absorbing agent production methods 1 to 3, each of which methods preferably includes carrying out control so that a particulate water absorbing agent obtained by mixing a polyvalent metal compound or a metallic soap (an organic salt of a polyvalent metal) with a water absorbing resin satisfies the following requirements (1), (2) and (4):

(1) a polyvalent metal cation is contained in an amount between 0.001 wt % and 5 wt % relative to the amount of the particulate water absorbing agent;

(2) an absorbency without pressure (CRC) of the particulate water absorbing agent is not less than 28 (g/g) and an absorbency against pressure (AAP 4.83 kPa) of the particulate water absorbing agent is not less than 10 (g/g); and (4) a moisture content of the particulate water absorbing agent is between 5 wt % and 20 wt %.

A method of producing a particulate water absorbing agent (production method 3) in accordance with the present invention includes controlling the moisture content of a particulate water absorbing agent, which is obtained by adding a metallic soap and water to the water absorbing resin (water absorbing resin powder or water absorbing resin particles), so that the moisture content is between 5 wt % and 20 wt %.

A method of adding the metallic soap and water is not particularly limited. For example, it is possible to employ any of the following production methods a to g.

It should be noted that a water absorbing resin contained in a particulate water absorbing agent of the present invention is not particularly limited, and may either be a water absorbing resin powder that has not been surface-crosslinked or surface-crosslinked water absorbing resin particles.

(Production Method a)

A metallic soap is added to a water absorbing resin powder to obtain a mixture. After that, the mixture is surface-crosslinked to obtain water absorbing resin particles. After that, water is added to obtain a particulate water absorbing agent of the present invention.

(Production Method b)

A water absorbing resin powder is surface-crosslinked to obtain water absorbing resin particles. After that, a metallic soap is added. After that, water is added to obtain a particulate water absorbing agent of the present invention.

(Production Method c)

A water absorbing resin powder is surface-crosslinked to obtain water absorbing resin particles. After that, an aqueous dispersion of a metallic soap is added to obtain a particulate water absorbing agent of the present invention.

(Production Method d)

A water absorbing resin powder is surface-crosslinked to obtain water absorbing resin particles. After that, water is added. After that, a metallic soap is added to obtain a particulate water absorbing agent of the present invention.

(Production Method e)

When a water absorbing resin powder is surface-crosslinked, a surface crosslinking agent and a metallic soap are simultaneously added to obtain a particulate water absorbing agent of the present invention.

(Production Method f)

A metallic soap in a powdery state or an aqueous dispersion of a metallic soap is added to a hydrous gel that has not yet been dried (i.e., a hydrous gel having a moisture content of between 10 wt % and 80 wt %, preferably between 20 wt % and 70 wt %). After that, a resultant hydrous gel is dried to obtain a particulate water absorbing agent of the present invention.

(Production Method g)

The same operations as in the production method f are repeated except that, after the metallic soap in the powdery state or the aqueous dispersion of the metallic soap is added to the hydrous gel that has not yet been dried and then the resultant hydrous gel is dried, a metallic soap in a powdery state or an aqueous dispersion of a metallic soap is further added to a dried gel or added during or after surface treatment. In this way, a particulate water absorbing agent of the present invention is produced.

According to the water absorbing agent production methods 1 and 2, it is possible to obtain the third particulate water absorbing agent of the present invention by controlling, after adding a metallic soap by the production method a, b, c, d, e, f or g, the moisture content so that the moisture content of a final product will fall within the foregoing range, i.e., between 5 wt % and 20 wt %, preferably between 5 wt % and 18 wt %, and more preferably between 6 wt % and 18 wt %.

Instead of the foregoing production methods a to g, a metallic soap can be added by for example (i) a dry blending method by which to directly mix a metallic soap in a powdery state to a water absorbing resin or (ii) a method of dispersing a metallic soap in a powdery state in water with use of a dispersion stabilizer to obtain an aqueous dispersion of the metallic soap and then mixing the aqueous dispersion of the metallic soap with a water absorbing resin. Out of these, in the present invention, the method of adding the aqueous dispersion of the metallic soap is more preferable than the dry blending method, because the dry blending method entails a risk of deterioration in operating environments due to powder dust and a risk of dust explosion due to powder dust.

In the production methods a to g, in a case where a metallic soap is added in the form of an aqueous dispersion, the metallic soap and water are added simultaneously. Accordingly, the metallic soap efficiently adhere to the surface of a water absorbing resin, and particles of the water absorbing resin becomes less adhesive to each other. This attains the objects of the present invention to a greater extent.

The aqueous dispersion of the metallic soap to be added preferably contains water and a dispersion stabilizer (preferably a surfactant) in amounts described later. Adding such an aqueous dispersion will provide a water absorbing agent that contains the water and the dispersion stabilizer in amounts falling within the preferable ranges. Further, before or after the aqueous dispersion of the metallic soap is added, the water and/or the dispersion stabilizer in a water absorbing resin may be dried as appropriate, or water or a dispersion stabilizer may further be added to the water absorbing resin. It is preferable that the water and the dispersion stabilizer (surfactant) which were added simultaneously with the metallic soap remain contained in a water absorbing agent for use, provided that the amount thereof falls within the range described later.

Further, in an aqueous dispersion containing a metallic soap and a dispersion stabilizer for use in the present invention, an additive (described later, e.g., a chelating agent, a deodorizer, an anti-coloring agent) serving as the other component may be dissolved or dispersed so as to further modify the water absorbing agent, provided that the amount of the additive falls within the range described later. Furthermore, granulation and/or suppression of fine powder (the fine powder is for example made up of water absorbing resin particles of less than 150 μm in diameter) may be carried out by adding an aqueous dispersion of a metallic soap.

The granulation may be carried out by heating the foregoing mixture, pulverizing the mixture if needed, and essentially classifying the mixture. Further, the granulation is carried out such that the weight median particle size of a particulate water absorbing agent becomes preferably 1.01 to 10 times, more preferably 1.02 to 2 times, and particularly preferably 1.05 to 1.5 times the weight median particle size before the aqueous dispersion of the metallic soap is added. It should be noted that the granulation is carried out by binding a plurality of water absorbing resins at their surfaces. The granulation is suitably applicable to the water absorbing agent production method 3 and to the first to fourth water absorbing agents.

The amounts of a metallic soap, water and a dispersion stabilizer contained in each of the second and third (and further the first and fourth) particulate water absorbing agents and/or the amounts of a metallic soap, water and a dispersion stabilizer to be added to a water absorbing resin are determined relatively to 100 parts by weight of the water absorbing resin. The amount of a metallic soap is preferably between 0.001 and 5 parts by weight, more preferably between 0.001 and 3 parts by weight, and further preferably between 0.01 and 3 parts by weight. An amount of a metallic soap contained and/or an amount of a metallic soap to be added falling within the above range are/is preferable, because fluidity after moisture absorption is dramatically improved and load to be applied on a mixer when water is added is significantly reduced. The amount of water is preferably between 3 and 25 parts by weight, more preferably between 3 and 20 parts by weight, and further preferably between 5 and 10 pats by weight. Further, the amount of a dispersion stabilizer to be added simultaneously or separately is preferably between 0.0001 and 1 part by weight, more preferably between 0.001 and 1 part by weight, and particularly preferably between 0.002 and 0.5 part by weight. An amount of a dispersion stabilizer contained and/or an amount of a dispersion stabilizer to be added falling within the above range are/is preferable, because the rate of water absorption is dramatically improved.

Accordingly, in a case where the second and third (and further first or fourth) particulate water absorbing agents are to be obtained by adding a metallic soap and water to a water absorbing resin, it is preferable that the metallic soap be added in an amount between 0.001 and 5 parts by weight and the water be added in an amount between 3 and 25 parts by weight, relative to 100 parts by weight of the water absorbing resin.

According to the present invention, in a case where a metallic soap is added in the form of an aqueous dispersion, (i) the concentration of the metallic soap in the aqueous dispersion is preferably between 1 wt % and 90 wt %, more preferably between 1 wt % and 60 wt %, and further preferably between 1 wt % and 40 wt % and (ii) the concentration of a dispersion stabilizer in the aqueous dispersion is preferably more than 0 wt % but not more than 10 wt %, more preferably more than 0 wt % but not more than 5 wt %, and further preferably more than 0 wt % but not more than 3 wt %. Further, the amounts of the metallic soap, dispersion stabilizer and water contained in the aqueous dispersion are controlled to fall within the above range relative to 100 parts by weight of the water absorbing resin. By adding the foregoing amount(s) of (a) water and a metallic soap or (b) an aqueous dispersion of a metallic soap as above and further controlling the moisture content so as to achieve the moisture content described later, stability to shock and dusting rate are dramatically improved.

According to the production method 1 (and further the production method 2) of the present invention, stirring torque (defined in the measurement method in Examples) after an aqueous dispersion is added is low. Accordingly, no excessive load is applied during stirring when water is added, and water absorbing resin particles are not destroyed. This achieves excellent physical properties and prevents an increase in generation of powder dust. The stirring torque is not more than 1.5 [N·m], preferably not more than 1.0 [N·m], and further preferably not more than 0.70 [N·m].

Further, according to the production method 1 (and further the production method 2) of the present invention using an aqueous dispersion of a metallic soap, few coarse particles (aggregated particles, excessively-aggregated particles) are generated even if water is added to a water absorbing resin powder. Therefore, a resulting water absorbing resin contains few coarse particles. Specifically, the amount of coarse particles contained in the water absorbing resin is between 0 wt % and not more than 5 wt %, further not more than 2 wt %, and particularly not more than 1 wt %. Therefore, no cost increase is caused by disposition and/or separation of coarse particles, and no reduction occurs in physical properties of the water absorbing agent by pulverization of the coarse particles. Note here that the coarse particles can be distinguished in the following manner. With use of a JIS standard sieve having a mesh opening size of 850 µm, the amounts of 850 µm-on particles (i.e., the amounts of particles remaining on the 850-µm sieve) of (i) a water absorbing resin powder to which water has not yet been added and of (ii) a water absorbing agent to which water has been added are measured. Then, the amount of 850 µm-on particles (i.e., the amount of particles remaining on the 850-µm sieve) [wt %], which amount is a difference between the amounts obtained before and after water is added, is calculated.

According to the present invention, an apparatus to be used for mixing the metallic soap or the aqueous dispersion of the metallic soap with the water absorbing resin is for example, but not limited to, a cylindrical mixer, a screw-type mixer, a screw-type extruder, Turbulizer, a Nauter mixer, a V-shaped mixer, a ribbon mixer, a double-arm kneader, a fluidization mixer, an air mixer, a rotating disc mixer, a roll mixer, a tumbling mixer, a Loedige mixer, or the like. The method of mixing is for example a batch method, a continuous method, or a combination of the batch and continuous methods. In view of industrial productivity, the continuous method is more preferable.

According to the particulate water absorbing agent production method 1 (and further the production method 2) of the present invention, the metallic soap or the aqueous dispersion of the metallic soap is mixed with the water absorbing resin under the following conditions.

That is, although a generally used mixing apparatus is a rotating mixer, the rotation speed of the mixing apparatus is not particularly limited provided that the water absorbing resin is not damaged. Specifically, the rotation speed is preferably between 5 rpm and 3000 rpm, more preferably between 10 rpm and 500 rpm, and further preferably between 15 rpm and 300 rpm. A rotation speed of more than 3000 rpm is not preferable, because powder dust of the water absorbing resin is generated and water absorbing properties are reduced. On the other hand, a rotation speed of less than 5 rpm is not preferable, because materials are not thoroughly mixed and a desired effect of improving fluidity after moisture absorption cannot be obtained.

The temperature of a water absorbing resin powder before being mixed with the metallic soap or with the aqueous dispersion of the metallic soap is, but not particularly limited to, between room temperature and 120° C., more preferably between 50° C. and 100° C., and further preferably between 50° C. and 80° C. A temperature of the water absorbing resin powder of more than 120° C. is not preferable for the following reason. That is, the added water evaporates, thereby necessitating addition of a large amount of water to achieve a desired moisture content and further increasing load applied on the mixing apparatus.

The mixing time during which the metallic soap or the aqueous dispersion of the metallic soap is mixed with the water absorbing resin is, but not particularly limited to, preferably between 1 second and 20 minutes, more preferably between 10 seconds and 10 minutes, and further preferably between 20 seconds and 5 minutes. A mixing time of more than 20 minutes is not preferable for the following reason. That is, the resulting effect is not so good relatively to the period of time and, on the contrary, the water absorbing resin turns into a powder state. This causes an increase in the amount of fine powder (fine particles that can pass through a sieve having a mesh opening size of 150 µm) and an increase in the amount of powder dust.

As is clear from above, the most preferable mixing condition to obtain a particulate water absorbing agent of the present invention is as follows: the temperature of a water absorbing resin powder is between 50° C. and 80° C., the rotation speed of a mixing apparatus is between 30 rpm and 300 rpm, and the mixing time is between 20 seconds and 5 minutes. A particulate water absorbing agent obtained under this condition is excellent in handleability, and does not cause a problem of adhesion or aggregation etc. Therefore, it is not necessary to carry out the drying step for improving handleability.

(b) Metallic Soap

According to the second and third (and further the first and fourth) water absorbing agents and the water absorbing agent production methods 1 and 2 (and further the production method 3), a metallic soap usable in the present invention means an organic acid polyvalent metal salt, which is a metal salt other than alkali metal salts such as a fatty acid, a petroleum acid and a polyacid each having 7 or more carbon atoms. The metallic soap to be used generally contains a polyvalent metal cation(s), and is not or hardly soluble in water. According to the water absorbing agent production methods 1 and 2 using a metallic soap, a resulting water absorbing agent will contain a predetermined amount of a polyvalent metal cation(s) originating from a metallic soap or a polyvalent metal compound. Note here that the metallic soap and a water-soluble polyvalent metal compound (described later) may remain in the water absorbing agent or change by a reaction with the water absorbing resin. Note, however, that the polyvalent metal cation(s) originating from the metallic soap or the water-soluble polyvalent metal compound will be contained in the resulting water absorbing agent, usually almost all of them will be contained in the resulting water absorbing agent. For example, the amount of the polyvalent metal cation(s) is between 0.001 wt % and 5 wt %, and further between 0.005 wt % and 3 wt %. These amounts can be easily determined by the method described later.

An organic acid constituting the metallic soap is not particularly limited, provided that the organic acid is the one that forms a salt with a polyvalent metal. The organic acid is preferably an organic carboxylic acid, an organic sulfonic acid, or an organic sulfinic acid. The organic acid is particularly preferably an organic carboxylic acid having a carboxyl group within a molecule.

The number of carbon atoms in the organic acid is preferably not less than 7, more preferably between 7 and 20, and further preferably between 12 and 20. An organic acid having less than 7 carbon atoms is not preferable, because the solubility of the metallic soap in water is increased and the metallic soap may seep into urine or blood etc. when a disposable diaper or an absorbent core etc. is in use. Further, for example in a case where an acid such as an oxalic acid or a citric acid is used, a polyvalent metal salt constituted by such acids has a high degree of hardness. This may cause a reduction in water absorbing properties upon mechanical shock. Further, using an oxalic acid is not preferable in view of safety. Further, using an organic acid having more than 20 carbon atoms is not preferable, because such an organic acid is difficult to obtain and is expensive.

The organic carboxylic acid is not particularly limited provided that the organic carboxylic acid is a saturated or unsaturated aliphatic carboxylic acid or a saturated or unsaturated aromatic carboxylic acid, and may have a substituent other than carboxyl groups, for example a hydroxyl group or a halogen atom etc. Further, the organic carboxylic acid may be a polyhydric carboxylic acid having a plurality of carboxyl groups within a molecule, and is more preferably a monocarboxylic acid. Specific examples of the organic carboxylic acid include: linear fatty acids and branched fatty acids such as octylic acid, octynoic acid, decanoic acid, lauric acid, myristic acid, palmitic acid, oleic acid, stearic acid, beef fatty acid, and hardened castor oil fatty acid; petroleum acids such as benzoic acid, naphthenic acid, naphthoic acid, and naphthoxyacetic acid; and polyacids such as poly(meth)acrylic acid and polysulfonic acid.

Out of those described above, a long-chain fatty acid such as octylic acid, octynoic acid, decanoic acid, lauric acid, myristic acid, palmitic acid, oleic acid, stearic acid, beef fatty acid, or hardened castor oil fatty acid is preferable; a long-chain saturated fatty acid having no unsaturated bond within a molecule such as octylic acid, decanoic acid, lauric acid, myristic acid, palmitic acid or stearic acid is more preferable; and a $C_{12}$-$C_{20}$ long-chain saturated fatty acid having no unsaturated bond within a molecule such as lauric acid, myristic acid, palmitic acid or stearic acid is most preferable.

It should be noted that using a fatty acid having an unsaturated bond as the organic carboxylic acid is not preferable, because a particulate water absorbing agent of the present invention deteriorates in color tone or generates an odor etc. when subjected to heat or oxidation during storage.

A metal salt constituting the metallic soap is not particularly limited, provided that the metal salt is other than alkali metal salts, i.e., a polyvalent metal salt such as an alkali earth metal salt or a transition metal salt etc. Note however that, in view of availability, barium salt, calcium salt, magnesium salt, aluminium salt, and zinc salt are preferable; and calcium salt, magnesium salt, zinc salt, and aluminium salt are more preferable.

Accordingly, specific examples of the metallic soap include: calcium laurate, magnesium laurate, zinc laurate, aluminium laurate, calcium myristate, magnesium myristate, zinc myristate, aluminium myristate, calcium palmitate, magnesium palmitate, zinc palmitate, aluminum palmitate, calcium stearate, magnesium stearate, zinc stearate and aluminum stearate. Note, however, that the metallic soap is not limited to the above, and any organic acid can be used in combination with a metal salt. These metallic soaps may be used solely or two or more metallic soaps may be used in combination.

Further, part of the metallic soap may be a hydroxide or the like. Specifically, the metallic soap may have a salt structure represented by for example (Organic Acid)$_x$M$^{n+}$(OH)$_{n-x}$, wherein M$^{n+}$ represents a n– valent metal ion, x is an integer between 1 and n, and n is an integer of 2 or greater.

According to the metallic soap in accordance with the present invention, not all of the acid radicals necessarily have to be salts. The metallic soap may contain a few organic acid(s) or may contain excess polyvalent metal. Note, however, that it is preferable that the metallic soap be a salt in which not less than mol % of acid radicals (carboxyl groups) are neutralized, more preferably 95 mol % to 105 mol %, further preferably 98 mol % to 102 mol %, and particularly preferably 99 mol % to 101 mol % of acid radicals (carboxyl groups) are neutralized.

In a case where a polyacid such as polyacrylic acid is used as the organic acid, it is preferable that not less than 95 mol %, more preferably not less than 98 mol %, and further preferably not less than 99 mol % of acid radicals (carboxyl groups) of the polyacid are neutralized to form a salt with a polyvalent metal. Further, the weight-average molecular weight of the polyacid is preferably between 10,000 and 5,000,000, and more preferably between 50,000 and 1,000,000.

The metallic soap is in a powdery state, and its particle size is not particularly limited. Usually, it is preferable that the particle size be smaller than the weight median particle size (D50) of the water absorbing resin particles. Specifically, the particle size of the metallic soap contained in the particulate water absorbing agent of the present invention is preferably more than 0 μm but less than 100 μm, more preferably not less than 0.01 μm but less than 50 μm, and further preferably not less than 0.01 μm but less than 10 μm in median diameter. It should be noted that the median diameter means a particle diameter (cumulative average diameter) corresponding to 50% on a cumulative distribution curve. The particle diameter is found by (i) plotting a cumulative curve assuming that all the particles serve as a single group and regarding the total volume of the group as 100% and (ii) finding a point where the cumulative curve is 50%. The median diameter can be measured by dispersing a metallic soap in a solvent such as methanol and measuring the median diameter with use of a particle size distribution measuring apparatus LS-920 (HORIBA, Ltd.) or the like.

According to the present invention, the melting point of the metallic soap is preferably between 20° C. and 250° C., more preferably between 40° C. and 250° C., further preferably between 50° C. and 250° C., further more preferably between 60° C. and 250° C., particularly preferably between 70° C. and 250° C., and most preferably between 80° C. and 250° C. If the melting point of the metallic soap is higher than 250° C., the metallic soap less adheres to the surface of the water absorbing resin, and a larger amount of metallic soap may fall off from the water absorbing resin. Further, a melting point of the metallic soap of lower than 20° C. is not preferable, because fluidity of a resulting particulate water absorbing agent decreases and thus handleability degreases. For this reason, when the particulate water absorbing agent is handled industrially, a method is employed by which to add heat and keep the heat in a hopper for storing the particulate water absorbing agent or water absorbing resin, in a transport pipe and/or in a metering feeder etc. for the purpose of preventing the particulate water absorbing agent from absorbing moisture. In this case, usually the temperature is kept (heated or the heat is kept) at between 30° C. and 80° C.

Conventionally, most of additives such as polyethylene glycol and surfactants generally have a low melting point or a low glass transition temperature. The additives are used for improving a powder property after moisture absorption or a property of a powder having a moisture content of between 0 wt % and 20 wt %, in particular for improving fluidity. Accordingly, there has been a problem in which, even if the fluidity of the particulate water absorbing agent is excellent at room temperature, the fluidity of a powder of the particulate water absorbing agent decreases and thus handleability decreases because the forgoing additive is melted by heat added to a production apparatus and/or transport line etc. during production of the particulate water absorbing agent or a disposable diaper etc. In this regard, according to the present invention, since a metallic soap having the foregoing melting point is used, no reduction occurs in industrial handleability of the particulate water absorbing agent when heating is carried out.

It should be noted that the melting point of the metallic soap may be actually measured or the melting point shown in Encyclopedia Chimica (Kagaku Daijiten, Edited by The Editing Committee for Encyclopedia Chimica, published by KYORITSU SHUPPAN CO., LTD) etc. may be used. For example, according to Encyclopedia Chimica, the melting point of zinc stearate is between 128° C. and 130° C., the melting point of aluminum stearate is 103° C., the melting point of calcium stearate is 180° C., and the melting point of magnesium stearate is 200° C. Accordingly, such metallic soaps are suitably usable, because each of them has a melting point most suitable for use in a particulate water absorbing agent of the present invention. In addition, appropriately selecting a metallic soap to be used makes it possible to control the melting point so that the melting point ranges widely. Note however that, when putting a metallic soap into practical use, it is preferable to select and use a metallic soap having a melting point equal to or higher than a temperature at which the particulate water absorbing agent of the present invention is used.

The metallic soap is preferably insoluble or hardly soluble in deionized water at 25° C. For example, the solubility of the metallic soap is preferably between 0 [g/L] and 10 [g/L], more preferably between 0 [g/L] and 5 [g/L], and further preferably between 0 [g/L] and 2 [g/L], relative to 1000 mL of deionized water. A solubility of the metallic soap of more than 10 [g/L] is not preferable, because, as described earlier, the metallic soap may seep into urine or blood etc.

When implementing the present invention, it is preferable to add a metallic soap and water in the form of an aqueous dispersion of a metallic soap. As used herein, the aqueous dispersion means a water in which a metallic soap is evenly dispersed with use of a dispersion stabilizer (described later), which water has fluidity. It is preferable that the aqueous dispersion have a viscosity of up to 10000 cps (25° C.). Note, however, that an aqueous dispersion having low viscosity is also usable in the present invention. An aqueous dispersion having a viscosity substantially the same as that of water can be used. For example, a slurry, a suspension liquid, and an emulsion etc. are encompassed in the aqueous dispersion in accordance with the present invention. Further, in a case where the metallic soap is produced in the form of an aqueous dispersion, the aqueous dispersion can be used directly without being dried or can be used after being concentrated or diluted to some extent.

(c) Dispersion Stabilizer

According to the second and third (and further the first and fourth) water absorbing agents and the water absorbing agent production methods 1 and 2 (and further the production method 3), in a case where a metallic soap is used in the form of an aqueous dispersion, a dispersion stabilizer is preferably used for the purpose of dispersing the metallic soap in water stably without aggregation and particularly for causing the metallic soap to be stable in colloidal form in water. The dispersion stabilizer may be added separately from the metallic soap for the propose of improving physical properties of a resulting water absorbing agent.

The dispersion stabilizer is not particularly limited, provided that it has conventionally been used for stably dispersing water-insoluble fine particles in water. The dispersion stabilizer is for example a water-soluble polymer, a hydrophilic organic solvent, or a surfactant etc. (described later), and is preferably a surfactant. Further, according to the water absorbing agent production methods 1 and 2 (and further the production method 3), such a dispersion stabilizer used will remain on the surface of a resulting water absorbing agent or will be contained in the resulting water absorbing agent in a predetermined amount. This further improves physical properties (e.g., shock resistance, transportability) of the resulting water absorbing agent.

(c-1) Water-Soluble Polymer

According to the second and third (and further the first and fourth) water absorbing agents and the water absorbing agent production methods 1 and 2 (and further the production method 3) of the present invention, a water-soluble polymer used as a dispersion stabilizer for a metallic soap is for example, but not particularly limited to, polyvinyl alcohol, starch, (carboxy)methyl cellulose, hydroxyethyl cellulose, polyacrylic acid (salt) or the like. The water-soluble polymer to be used is preferably soluble in water (25° C.) in an amount of preferably not less than 1 wt %, more preferably not less than 5 wt %, and further preferably not less than 10 wt %. The molecular weight of the water-soluble polymer is preferably between 500 and 50,000,000, more preferably between 1000 and 5,000,000, and further preferably between 10,000 and 1,000,000.

(c-2) Hydrophilic Organic Solvent

According to the second and third (and further the first and fourth) water absorbing agents and the water absorbing agent production methods 1 and 2 (and further the production method 3) of the present invention, a hydrophilic organic solvent used as a dispersion stabilizer for a metallic soap is for example, but not particularly limited to, a hydrophilic organic solvent etc. used in combination with the crosslinking agent in the foregoing surface crosslinking. Specifically, polyhydric alcohols such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,3-butanediol, 1,4-butanediol, 1,5-pentanediol, 1,6-hexanediol, 1,2-cyclohexane dimethanol, 1,2-cyclohexanol, trimethylolpropane, diethanolamine, triethanolamine, polyoxypropylene, oxyethylene-oxypropylene block copolymers, pentaerythritol, and sorbitol are preferable, $C_2$-$C_{10}$ polyhydric alcohols are more preferable, and $C_3$-$C_8$ polyhydric alcohols are further preferable. Further, hydroxy groups of such polyhydric alcohols may be partially alkoxylated (e.g., methoxy polyethylene glycol).

Out of the above polyhydric alcohols, it is preferable to use ethylene glycol, propylene glycol, propanediol, butanediol, pentanediol, hexanediol, glycerin and/or trimethylolpropane. These polyhydric alcohols may be used solely or two or more polyhydric alcohols may be used in combination.

(c-3) Surfactant

According to the second and third (and further the first and fourth) water absorbing agents and the water absorbing agent production methods 1 and 2 (and further the production method 3) of the present invention, a surfactant used as a dispersion stabilizer for a metallic soap is not particularly limited. Examples of the surfactant include: polyoxyalkylene alkyl ethers such as polyoxyethylene lauryl ether, polyoxyethylene cetyl ether, polyoxyethylene stearyl ether, and polyoxyethylene oleyl ether; polyoxyalkylene alkylphenyl ethers such as polyoxyethylene octylphenyl ether and polyoxyethylene nonylphenyl ether; polyoxyalkylene alkylamino ethers such as polyoxyethylene laurylamino ether and polyoxyethylene stearylamino ether; sorbitan fatty acid esters such as sorbitan monolaurate, sorbitan monopalmitate, sorbitan monostearate, and sorbitan monooleate; polyoxyalkylene sorbitan fatty acid esters such as polyoxyethylene sorbitan monolaurate, polyoxyethylene sorbitan monopalmitate, polyoxyethylene sorbitan monostearate, and polyoxyethylene sorbitan monooleate; polyalkylene glycol fatty acid esters such as polyethylene glycol monolaurate, polyethylene glycol monooleate, polyethylene glycol monostearate, polyethylene glycol dilaurate, and polyethylene glycol distearate; nonionic surfactants, for example glycerine fatty acid esters such as monoglyceride laurate, monoglyceride stearate, and monoglyceride oleate; sulfuric ester salts such as sodium polyoxyethylene laurylether sulfate, sodium polyoxyethylene octylphenylether sulfate, sodium polyoxyethylene nonylphenylether sulfate, triethanolamine lauryl sulfate, sodium lauryl sulfate, potassium lauryl sulfate, and ammonium lauryl sulfate; sulfonates such as sodium dodecylbenzenesulfonate, alkyl sodium naphthalene sulfonate, and dialkyl sulfo sodium succinate; anionic surfactants, for example phosphoric acid ester salts such as alkyl potassium phosphate; and cationic surfactants, for example quarternary ammonium salts such as lauryl trimethylammonium chloride, stearyl trimethylammonium chloride, cetyl trimethylammonium chloride, and stearyl trimethylammonium chloride. These surfactants may be used solely or two or more surfactants may be used in combination. Out of these surfactants, it is preferable to use an nonionic surfactant or an anionic surfactant.

It is preferable to use a surfactant as a dispersion stabilizer for a metallic soap. A method for producing an aqueous dispersion of a metallic soap in which a surfactant is used as a dispersion stabilizer may be for example a method described in Japanese Patent Application Publication "Tokukaisho No. 59-219400" or a method described in Translation of PCT Patent Application "Tokuhyohei, No. 4-7260". Further, commercially available aqueous dispersions such as Zinc Stearate N (manufactured by NOF CORPORATION.), Hidorin Z-7-30, Hidorin O-128 (manufactured by CHUKYO YUSHI CO., LTD), Afco-Disper ZD, Afco-Disper C (manufactured by ADEKA CHEMICAL SUPPLY CO., LTD.) and/or the like may be used directly.

(d) Controlling Moisture Content

The second and third (and further the first and fourth) particulate water absorbing agents in accordance with the present invention can be obtained by adding a metallic soap and water to a water absorbing resin by the foregoing method so as to control the moisture content to a predetermined moisture content. The predetermined moisture content is between 5 wt % and 20 wt %, preferably between 5 wt % and 18 wt %, more preferably between 6 wt % and 17 wt %, further preferably between 7 wt % and 15 wt %, and particularly preferably between 8 wt % and 13 wt %.

How to control the moisture content is not particularly limited. For example, the amount of water or the amount of an aqueous dispersion of a metallic soap to be added may be controlled as appropriate depending on the moisture content of a water absorbing resin to be used. Alternatively, a predetermined amount of water may be allowed to remain in a particulate water absorbing agent.

Alternatively, after the foregoing amount of water or the foregoing amount of an aqueous dispersion of a metallic soap is added to a water absorbing resin, the water absorbing resin is dried by heating or dried under reduced pressure so that its moisture content is controlled.

Alternatively, after water or an aqueous dispersion of a metallic soap is added to a water absorbing resin, the absorbing resin may be heated and/or dried as needed. In a case where the moisture content is to be controlled by drying by heating etc., infiltration of water into the water absorbing resin is promoted, and the surface is dried so that the water absorbing resin can quickly turn into particles.

Alternatively, in a case where a metallic soap is added together with water to a hydrous gel or a case where an aqueous dispersion of a metallic soap is added to a hydrous gel, the heating condition etc. of the drying step or the surface crosslinking step are determined as appropriate so that the moisture content becomes a predetermined moisture content of the particulate water absorbing agent.

By controlling the moisture content of the particulate water absorbing agent so that the moisture content falls within the above range, it is possible to obtain a particulate absorbing agent which has improved fluidity after moisture absorption and improved water absorbing property (AAP) and is excellent in shock resistance (abrasion resistance). Further, it is possible to suppress the particulate water absorbing agent from being charged, and thus possible to dramatically improve handleability of powder.

In a case where the moisture content is controlled by drying by heating, the heating temperature is preferably between 30° C. and 100° C., more preferably between 50° C. and 90° C., and further preferably between 60° C. and 80° C. The heating time is preferably between 1 second and 3 hours, and further is determined as appropriate to between 1 minute and 1 hour. A water absorbing agent that has entered into a powder state by being heated as needed may be used directly, or may be further disintegrated, classified and/or granulated as needed.

(e) Particle Size Control Step (Granulation Step, Particle Sizing Step, Fine Powder Collection Step)

Each of the second and third (and further the first and fourth) particulate water absorbing agents of the present invention may be subjected to an appropriate process(es) such as the particle sizing step, granulation step and/or fine powder collection step etc. so that the particulate water absorbing agent has a predetermined particle size (described later), as needed. It should be noted that the particle size control step is for example the step described in US Patent Application Publication, No. 2004/181031, US Patent Application Publication, No. 2004/242761, or US Patent Application Publication, No. 2006/247351 etc.

(f) Other Component Contained in Particulate Water Absorbing Agent

To the second and third (and further the first and fourth) particulate water absorbing agents of the present invention, for the purpose of further imparting various properties, insoluble fine particles such as an inorganic powder or a hydrophilic solvent such as water may be added in addition to the foregoing components (water absorbing resin, organic polyvalent metal salt, internal crosslinking agent, polymerization initiator, surface crosslinking agent etc.), and the water absorbing resin etc. may be granulated.

Specific examples of the inorganic powder include: metallic oxides such as silicon dioxide and titanium oxide; silicic acids (salts) such as natural zeolite and synthetic zeolite; kaolin; talc; clay; and bentonite. Out of these, silicon dioxide and silicic acids (salts) are more preferable, and silicon dioxide and silicic acids (salts) each having a mean particle size of not more than 200 μm measured by Coulter counter are preferable.

The amount of the inorganic powder to be added depends on a combination of the inorganic powder with various components contained in the particulate water absorbing agent. The amount of the inorganic powder is not particularly limited provided that the amount is between 0 an 6 parts by weight relative to 100 parts by weight of the water absorbing resin. The amount of the inorganic powder is more preferably between 0.001 and 5 parts by weight, and particularly preferably between 0.01 and 3 parts by weight. If the amount of the inorganic powder to be added is outside the above range, the shock absorption capacity of the metallic soap may become insufficient, and it may become difficult to prevent water absorbing properties from decreasing upon shock.

How to mix the water absorbing resin and the inorganic powder is not particularly limited. The inorganic powder may be mixed with the water absorbing resin simultaneously with or separately from an aqueous dispersion of a metallic soap. For example, it is possible to employ a dry blending method by which to blend powders or a wet blending method etc. The dry blending method is more preferable.

Further, the present invention may further include as needed a step of adding, simultaneously with or separately from an aqueous dispersion of a metallic soap, various additives as needed to impart various functions to a particulate water absorbing agent of the present invention. Examples of the various additives include: deodorizers, antimicrobial agents, perfumes, foaming agents, pigments, dyes, plasticizers, adhesives, surfactants, fertilizers, oxidizing agents, reducing agents, water, salts, chelating agents, germicides, hydrophilic polymers such as polyethylene glycol and polyethylene imine, hydrophobic polymers such as paraffin, thermoplastic resins such as polyethylene and polypropylene, and thermosetting resins such as polyester resins and urea resins. The amount of an additive to be added may be between 0 and 30 parts by weight, is preferably between 0 and 10 parts by weight, and more preferably between 0 and 1 part by weight, relative to 100 parts by weight of the water absorbing resin particles.

[6] Physical Properties of the First to Third (and Further the Fourth) Particulate Water Absorbing Agents According to the First to Third Embodiments <Moisture Content and Polyvalent Metal Cation>

The third (and further the first, second and fourth) particulate water absorbing agent(s) of the present invention is a particulate water absorbing agent which contains a water absorbing resin and a metallic soap and which has a moisture content of between 5 wt % and 20 wt %, preferably between 5 wt % and 18 wt %, and more preferably between 6 wt % and 18 wt %. The particulate water absorbing agent shows excellent fluidity after moisture absorption and excellent AAP, and in addition, shows excellent stability to shock.

<Particle Size>

Further, during production of the particulate water absorbing agent of the present invention, an extremely small number of particles are bound to one another (e.g., the percentage of particles having a particle size of not less than 850 μm in a hardened product is extremely small) when water is added, and the particle size is easily controlled to a desired particle size. The metallic soap and the dispersion stabilizer (surfactant) are contained inside the water absorbing resin or in the surface of the water absorbing resin, preferably contained at least in the surfaces of particles.

Specifically, the particulate water absorbing agent of the present invention (i) includes particles of not less than 106 μm but less than 850 μm in diameter in an amount between 90 wt % and 100 wt % relative to the total amount of particles, and particles of not less than 300 μm in diameter in an amount of not less than 60 wt % relative to the total amount of particles, (ii) has an absorbency against pressure (AAP 4.83 kPa) of not less than 10 [g/g], and (iii) has a fluidity after moisture absorption of between 0 wt % and 10 wt %. More preferably, the particulate water absorbing agent of the present invention shows the foregoing absorbency against pressure (4.83 kPa) and the foregoing fluidity after moisture absorption, and has a dusting rate of preferably between 0 wt % and 1.0 wt %, more preferably a dusting rate falling within the range described later.

The absorbency against pressure and stability to shock are physical properties that are in a trade-off relationship, and thus an increase in one of them decreases the other. That is, if the stability to shock is increased, the absorption against pressure decreases, and thus the fluidity after moisture absorption dramatically decreases. On the other hand, if the absorbency against pressure is increased, the stability to shock decreases. According to a conventional technique, it is not possible to improve both of these physical properties that are in a trade-off relationship. In this regard, according to the present invention, it is possible to improve both of these physical properties that are in a trade-off relationship.

The following description discusses preferable physical properties of the first to third (and further the fourth) particulate water absorbing agents of the present invention.

(6-1) Absorbency Against Pressure (AAP 4.83 kPa)

According to the foregoing production methods, no significant change is caused in physical properties by addition of a metallic soap. Therefore, it is possible to obtain a particulate water absorbing agent having high absorbency against pressure. The second and third (and further the first and fourth) particulate water absorbing agents of the present invention each have an absorbency against pressure falling within the range described earlier (in the (4-3)).

If absorbency (AAP) against a pressure of 4.83 kPa is less than 10 [g/g], it may be impossible to obtain a water absorbing agent in which the amount of liquid squeezed out (so-called Re-Wet) is small when the water absorbing agent is used in an absorbent core and pressure is applied to the absorbent core.

The reason why the absorbency against pressure under a load of 4.83 kPa is used is that it is assumed that, in a case where the particulate water absorbing agent of the present invention is used as a sanitary material such as a disposable diaper, such a load is applied to the particulate water absorbing agent when an infant is lying down or is sitting upright.

(6-2) Fluidity after Moisture Absorption

The "fluidity after moisture absorption" of the present invention is determined by evaluating blocking, caking, or fluidity of a powder under the condition where a particulate water absorbing agent is allowed to stand at a temperature of 25° C. with a relative humidity of 90%. The "fluidity after moisture absorption" is determined based on "blocking rate after moisture absorption".

Specifically how the blocking rate after moisture absorption is measured (evaluated) is described later. The blocking rate after moisture absorption of the first to fourth particulate water absorbing agents of the present invention is preferably between 0 wt % and 10 wt %, more preferably between 0 wt % and 5 wt %, and further preferably between 0 wt % and 2 wt %. If the blocking rate after moisture absorption is more than 10 wt %, the particulate water absorbing agent is difficult to handle in humid conditions. Accordingly, there may be a problem in which, during production of a thin absorbent core for sanitary materials etc., the water absorbing agent may aggregate in a transport pipe in a production plant and thus the transport pipe clogs and/or the water absorbing agent cannot be evenly mixed with hydrophilic tissue.

The foregoing blocking rate after moisture absorption is achieved by controlling the particle size of the water absorbing resin and then using a metallic soap or a metal compound (described later).

(6-3) CRC and Extractable Content (Ext)

The first to fourth particulate water absorbing agents of the present invention each preferably have a centrifugal retention capacity (CRC) falling within the range described earlier (in the (4-2)).

If the centrifugal retention capacity (CRC) is less than 10 [g/g], the water absorbency is so low that a resulting water absorbing agent is not suitable for use in sanitary materials such as a disposable diaper. On the other hand, if the centrifugal retention capacity (CRC) is more than 60 [g/g], it may be impossible to obtain a particulate water absorbing agent which is excellent in rate of liquid absorption into an absorbent core when the particulate water absorbing agent is used in the absorbent core.

The present invention provides a suitable absorbing article by achieving the forgoing CRC. According to foregoing production methods, no significant change is caused in CRC by addition of a metallic soap. Therefore, it is possible to obtain a particulate water absorbing agent having the foregoing particle size. Note, however, that classification and/or granulation may be carried out in the production methods as needed.

Further, the amount of extractables (Extr), which is specified in ERT 470.1-02, of the water absorbing resin is not more than 50 wt %, preferably not more than 30 wt %, and more preferably not more than 20 wt %.

(6-4) Dusting Rate

The dusting rate of each of the first to fourth particulate water absorbing agents of the present invention is obtained by evaluating the amount of fine powder generated in the production and transport of the particulate water absorbing agent.

The dusting rate of a particulate water absorbing agent of the present invention is between 0 wt % and 1.0 wt %, preferably between 0 wt % and 0.8 wt %, and more preferably between 0 wt % and 0.5 wt %. If the dusting rate is more than 1.0 wt %, there may be a problem in which a deterioration in operating environments is caused by powder dust generated during the production and transport of the particulate water absorbing agent.

(6-5) Particle Size

Each of the first to fourth particulate water absorbing agents of the present invention includes (i) particles of not less than 106 μm but less than 850 μm in diameter in an amount between 90 wt % and 100 wt % relative to the total amount of particles and (ii) particles of not less than 300 μm in diameter in an amount of not less than 60 wt % relative to the total amount of particles.

In particular, the particulate water absorbing agent preferably includes particles of not less than 106 μm but less than 850 μm in diameter in an amount between 95 wt % and 100 wt %, particularly preferably between 98 wt % and 100 wt %, relative to the total amount of particles. Further, the particulate water absorbing agent preferably includes particles of not less than 300 μm in diameter in an amount of preferably between 65 wt % and 100 wt %, more preferably between wt % and 100 wt %, and particularly preferably between 75 wt % and 100 wt %, relative to the total amount of particles.

Furthermore, the weight median particle size (D50) of the particulate water absorbing agent is preferably between 200 μm and 700 μm, further preferably between 300 μm and 600 μm, and particularly preferably between 400 μm and 500 μm. Moreover, the logarithmic standard deviation (σζ), which is an index of uniformity of particle size distribution, of the particulate water absorbing agent is preferably between 0 and 0.40, more preferably between 0 and 0.35, and most preferably between 0 and 0.30.

If a particulate water absorbing agent contains particles of not less than 850 μm in diameter in an amount of more than 10 wt % relative to the total amount of particles, such a particulate water absorbing agent will cause discomfort in a user, e.g., cause a user a feeling of a foreign body or a feeling of roughness, when used for producing a sanitary material such as a disposable diaper. Further, if a particulate water absorbing agent contains particles of less than 106 μm in diameter in an amount of more than 10 wt % relative to the total amount of particles and/or has a logarithmic standard deviation (σζ) of more than 0.40, such a particulate water absorbing agent is not preferable because many problems occur such as dramatic reductions in absorbency against pressure and fluidity after moisture absorption, deterioration in operating environments due to powder dust generated during production of sanitary materials such as disposable diapers, and an increase in segregation due to wide particle size distribution.

(6-6) Moisture Content of Particulate Water Absorbing Agent

The moisture content of each of the first, third and fourth (and further the second) particulate water absorbing agents in accordance with the first to third embodiments of the present invention is between 5 wt % and 20 wt %, preferably between 5 wt % and 18 wt %, more preferably between 6 wt % and 18 wt %, further preferably between 7 wt % and 15 wt %, and particularly preferably between 8 wt % and 13 wt %. It the moisture content is less than 5 wt %, such a particulate water absorbing agent is not preferable because sufficient stability to shock is not achieved and, in addition, the fluidity after moisture absorption decreases and thus handleability decreases. Further, if the moisture content is more than 20 wt %, such a particulate water absorbing agent is not preferable because water absorbing properties (e.g., AAP, CRC) decrease and the fluidity after moisture absorption decreases.

[7] Fourth Embodiment

The fourth embodiment of the present invention is a method (water absorbing agent production method 3) for producing a particulate water absorbing agent containing a water absorbing resin as a main component, which method includes: surface-treating the water absorbing resin by a surface treatment method including the steps of (a) mixing an acid radical-containing radical-polymerizable monomer, a polyvalent metal compound and water with the water absorbing resin and (b) polymerizing the acid radical-containing radical-polymerizable monomer.

It is preferable that the method be:
(1) a production method in which the step (b) includes irradiating a mixture obtained in the step (a) with activating light and/or heating the mixture obtained;
(2) a production method in which a degree of neutralization of the acid radical-containing radical-polymerizable monomer is between 0 mol % and 60 mol %;
(3) a production method in which the acid radical-containing radical-polymerizable monomer is a (meth)acrylic acid (salt);
(4) a production method in which the acid radical-containing radical-polymerizable monomer further contains a polyfunctional organic crosslinking agent;
(5) a production method in which, in the step (a), at least one type of radical polymerization initiator selected from the group consisting of persulfates, hydrogen peroxides and water-soluble azo compounds is further mixed with the water absorbing resin;
(6) a production method in which, in the step (a), a photodegradable polymerization initiator is further mixed with the water absorbing resin;
(7) a production method in which the water absorbing resin is a powdery polyacrylic acid (salt) water absorbing resin obtained by polymerizing a monomer containing a (meth) acrylic acid (salt) as a main component;
(8) a production method in which the polyvalent metal compound is a water-soluble polyvalent typical metal salt;
(9) a production method in which the polyvalent metal compound is an inorganic or organic water-soluble aluminum salt;
(10) a production method in which the acid radical-containing radical-polymerizable monomer is polymerized in the presence of water in an amount between 5 wt % and 20 wt % relative to the amount of the water absorbing resin;
(11) a production method in which the acid radical-containing radical-polymerizable monomer is mixed in an amount between 0.1 and 20 parts by weight relative to 100 parts by weight of the water absorbing resin, the polyvalent metal compound is mixed in an amount between 0.01 and 10 parts by weight relative to 100 parts by weight of the water absorbing resin, and the water is mixed in an amount between 1 and 50 parts by weight, relative to 100 parts by weight of the water absorbing resin;
(12) a method for producing a particulate water absorbing agent containing, as a main component, a surface-treated polyacrylic acid (salt) water absorbing resin, wherein the absorbency without pressure (CRC) is not less than 28 (g/g), the absorbency against pressure (AAP 4.83 kPa) is not less than 10 (g/g), the vertical diffusion absorbency under pressure (VDAUP) is not less than 20 g, and the moisture content is between 5 wt % and 20 wt %;
(13) a method for producing a water absorbing agent by further surface-treating the water absorbing agent obtained by the method (12) with a polyvalent metal;
(14) a method for producing a water absorbing agent by further surface-treating the water absorbing agent obtained by the method (12) or (13) with a polyvalent metal that is other than a metallic soap;
(15) a method for producing a water absorbing agent by further surface-treating any one of the water absorbing agents obtained by any one of the methods (12) through (14) with a water-soluble aluminum salt;
(16) a method for producing any one of the water absorbing agents obtained by any one of the methods (12) through (15), in which water absorbing agent a residual monomer content is not more than 500 ppm; and/or
(17) a method for producing any one of the water absorbing agents obtained by any of the methods (12) through (16), which water absorbing agent is a powder in a form of irregular fragments.

The following description describes in detail a method of surface-treating a water absorbing resin in accordance with the present invention. Note, however, that the scope of the present invention is not restricted by the following descriptions. Those other than the following descriptions, i.e., appropriate modifications of the following descriptions, can be implemented provided that the objects of the present inventions are attained.

[7-A] Materials for Fourth Embodiment (Water Absorbing Agent Production Method 3)

According to the water absorbing agent production method 3, it is possible to obtain the fourth water absorbing agent, and further possible to obtain the first to third water absorbing agents. The following description discusses the water absorbing agent production method 3 and the third water absorbing agent.

(1) Water Absorbing Resin

A water absorbing resin in accordance with the fourth embodiment of the present invention encompasses, as defined earlier, (i) a water absorbing resin powder (water absorbing resin precursor, base polymer) which is a water absorbing resin that has not yet been surface-treated nor surface-crosslinked and (ii) surface-crosslinked water absorbing resin particles.

It should be noted that the water absorbing resin powder (also referred to as a base polymer) is produced by the method described in the foregoing (3-1) to (3-3) of [3]. Further, the water absorbing resin particles are produced by the method described in the foregoing (3-4) of [3], and preferably has the properties described in the [4].

(2) Radical Polymerizable Compound (Surface-Treatment Agent for Water Absorbing Resin)

(2-1) Acid Radical-Containing Unsaturated Monomer

According to the production method 3 of the present invention, use of a radical polymerizable monomer containing an acid radical (acid radical-containing unsaturated monomer) is essential. Out of radical polymerizable monomers, a monomer containing an acid radical is excellent in water absorbing properties. Examples of the acid radical encompass carboxyl, sulfo, and phosphate groups.

The acid radical-containing radical-polymerizable monomer to be mixed with the water absorbing resin in the present invention is preferably a monomer containing an acid radical, out of the foregoing unsaturated ethylene monomers. Specific examples of the acid radical-containing radical-polymerizable monomer include: (meth)acrylic acid, 2-(meth)acryloyl ethanesulfonic acid, 2-(meth)acryloyl propanesulfonic acid, 2-(meth)acrylamide-2-methylpropanesulfonic acid, vinylsulfonic acid, styrenesulfonic acid and/or their salts. Out of these, in view of water absorbing properties, (meth)acrylic acid and 2-(meth)acrylamide-2-methylpropanesulfonic acid are more preferable, and acrylic acid is particularly preferable. The amount of acrylic acid (salt) is between 50 mol % and 100 mol %, further preferably between 70 mol % and 100 mol %, and particularly preferably between 90 mol % and 100 mol %, relative to the total amount of monomers. The acid radical-containing radical-polymerizable monomer may be used solely or a mixture of two or more types of acid radical-containing radical-polymerizable monomers may be used.

According to the production method 3 of the present invention, the degree of neutralization of the acid radical-containing radical-polymerizable monomer is preferably low. The ratio of the degree of neutralization of the monomer to that of the water absorbing resin falls within the following range (the degree of neutralization of the monomer is preferably not more than 0.8 times, not more than 0.6 times, not more than 0.4 times, and not more than 0.2 times the degree of neutralization of the water absorbing resin that has not yet been surface-treated).

Further, the degree of neutralization of the monomer is preferably between 0 mol % and 80 mol %, more preferably between 0 mol % and 60 mol %, further preferably between 0 mol % and 40 mol %, further preferably between 0 mol % and 25 mol %, particularly preferably between 0 mol % and 15 mol %, and most preferably between 0 mol % and 10 mol %.

The smaller the degree of neutralization of the acid radical-containing radical-polymerizable monomer, the faster the reaction in the subsequent surface treatment caused by irradiation with activating light and/or by heating. This makes it possible to obtain, at low temperatures within a short period of time, a water absorbing resin having excellent water absorbing properties. For example, this provides a significant economic effect in a case of large-scale production (preferably continuous production), e.g., in a case where the water absorbing resin is produced on a commercial scale of 1000 [kg/hr].

The degree of neutralization of the acid radical-containing radical-polymerizable monomer to be mixed is preferably not more than 80 mol % relative to the degree of neutralization of the water absorbing resin that has not yet been surface-treated (in other words, not more than 8/10 of the degree of neutralization of the water absorbing resin), more preferably not more than 60 mol % (not more than 6/10), further preferably not more than 40 mol % (not more than 4/10), particularly preferably not more than 20 mol % (not more than 2/10), and most preferably not more than 10 mol % (not more than 1/10).

It should be noted that the degree of neutralization means a ratio of the number of a neutralized acid radical(s) to the total number of acid radicals in the acid radical-containing radical-polymerizable monomer. The "total number of acid radicals in the acid radical-containing radical-polymerizable monomer" and the "number of neutralized acid radical" mean, in a case where two or more types of acid radical-containing radical-polymerizable monomers are used, the total number of acid radicals and the number of a neutralized acid radical(s) in each acid radical-containing polymerizable compound, respectively. For example, in a case of using an acid radical-containing radical polymerizable compound containing acrylic acid and sodium acrylate at a molar ratio of 1:1, the degree of neutralization of the acid radical-containing radical polymerizable compound is 50 mol %. That is, according to this method, the present invention provides a water absorbing resin in which preferably the degree of neutralization is lower in the surface than inside of the polyacrylic acid (salt) water absorbing resin powder.

In a case where the acid radical-containing radical-polymerizable monomer is neutralized (in a case where it is in the form of a salt), the compound is preferably a nomovalent salt selected from alkali metal salts, ammonium salts, and amine salts. The compound is more preferably an alkali metal salt, and particularly preferably a salt selected from sodium salts, lithium salts, and potassium salts.

The amount of the acid radical-containing radical-polymerizable monomer to be used is, but not particularly limited to, preferably between 0.1 and 20 parts by weight, more preferably between 0.5 and 15 parts by weight, further preferably between 1 and 10 parts by weight, particularly preferably between 1.5 and 8 parts by weight, and most preferably between 2 and 7 parts by weight, relative to 100 parts by weight of the water absorbing resin. Since the amount of the acid radical-containing radical-polymerizable monomer falls within the foregoing range, the effect of the present invention becomes noticeable. Since the amount of the acid radical-containing radical-polymerizable monomer is not less than 0.1 parts by weight, the water absorbing property under pressure of the water absorbing resin is sufficiently improved. Further, since the amount of the acid radical-containing radical-polymerizable monomer is not more than 20 parts by weight, no significant reduction occurs in water absorbency of a resulting surface-treated water absorbing resin.

(2-2) Monomer

According to the production method 3 of the present invention, an unsaturated ethylene monomer that can be used in addition to the acid radical-containing radical-polymerizable monomer is an unsaturated monomer usable in polymerization of the water absorbing resin (base polymer). Specific examples of the unsaturated ethylene monomer include: nonionic hydrophilic group-containing monomers such as (meth) acrylamide, N-substituted (meth)acrylamide, 2-hydroxyethyl (meth)acrylate, and 2-hydroxypropyl (meth)acrylate; and amino group-containing unsaturated monomers such as N,N-dimethylaminoethyl (meth)acrylate, N,N-diethylaminoethyl (meth)acrylate, N,N-diethylaminopropyl (meth) acrylate, and N,N-dimethylaminopropyl (meth)acrylamide; and their quaternary compounds.

The amount of the unsaturated ethylene monomer in such a case can be selected as appropriate depending on a desired property. Note, however, that the amount of the unsaturated ethylene monomer is preferably between 0 wt % and 100 wt %, more preferably between 1 wt % and 50 wt %, relative to 100 wt % of the acid radical-containing radial-polymerizable monomer.

Further, by appropriately selecting a radical polymerizable compound to be mixed with the water absorbing resin, it is possible to impart, to the surfaces of surface-treated water absorbing resin particles, various properties such as a hydrophilic property, hydrophobic property, adhesion property, biocompatibility, and/or the like. Patent Literature 30 describes an unsaturated ethylene monomer that imparts a hydrophilic property to the surfaces of water absorbing resin particles.

(2-3) Crosslinking Agent

According to the production method 3 of the present invention, it is preferable that a crosslinking agent (for example, a crosslinking agent that reacts with a carboxyl group) that is copolymerized with or reacts with a monomer (particularly acrylic acid) be used. That is, a crosslinkable unsaturated monomer that is crosslinkable with an acrylic acid and/or a crosslinking agent reactive with an acrylic acid (non-polymerizable crosslinking agent) are/is used.

As a crosslinkable unsaturated monomer that is copolymerizable with an acrylic acid, it is possible to use a crosslinking agent having a plurality of groups, in particular 2 to 10 groups, within a molecule. Examples of the groups include acrylate, acrylamide, and allyl groups. Further, as a crosslinking agent that is reactive with acrylic acid, it is possible to use a crosslinking agent having a plurality of groups, in particular 2 to 10 groups, within a molecule. Examples of the groups include epoxy, hydroxy, and amino groups. Each of the above can be used as a surface crosslinking agent. Further, a crosslinking agent having both of the above properties is for example a crosslinking agent having both a polymerizable group and a reactive group within a molecule, e.g., hydroxyethyl acrylate.

The crosslinkable unsaturated monomer is for example, but not particularly limited to, a crosslinking agent usable in polymerization of the water absorbing resin. Specific example of the crosslinkable unsaturated monomer includes a monomer to be used as an internal crosslinking agent in production of the water absorbing resin. Out of these, it is preferable to use polyethylene glycol diacrylate, trimethylolpropane tri(meth)acrylate, N,N'-methylenebis (meth)acrylamide, glycerin acrylate methacrylate and/or the like, in which the average number of ethylene oxides is between 2 and 50. In order for the crosslinkable unsaturated monomer to be efficiently copolymerized with an unsaturated ethylene monomer on the surface of the water absorbing resin, it is desirable that the crosslinkable unsaturated monomer and the unsaturated ethylene monomer have similar dispersibility in the water absorbing resin during the step of mixing with the water absorbing resin. To this end, it is desirable that the crosslinkable unsaturated monomer (polymerizable crosslinking agent) be similar in molecular weight and hydrophilic property to the unsaturated ethylene monomer to be used. Alternatively, it is possible to use for example a polyhydric alcohol or a polyhydric glycidyl compound exemplified as a surface crosslinking agent. That is, it is possible to use for example a non-polymerizable crosslinking agent such as ethylene glycol diglycidyl ether, (poly)glycerol glycidyl ether, or polyethylene glycol diglycidyl ether.

Two or more of the internal crosslinking agents may be used in combination. The amount of an internal crosslinking agent (preferably a crosslinkable unsaturated monomer) to be used can be selected as appropriate depending on a desired property. The amount of the internal crosslinking agent is preferably between 0 wt % and 20 wt %, more preferably between 0.1 wt % and 10 wt %, and most preferably between 0.5 wt % and 5 wt %, relative to 100 wt % of a radical polymerizable compound. Using also the internal crosslinking agent (particularly preferably a crosslinkable unsaturated monomer) makes it possible to further improve the vertical diffusion absorbency under pressure (VDAUP) and the absorbency against pressure (AAP). The reason why the VDAUP and the AAP are improved is unknown, but the reason is probably that the water-soluble unsaturated ethylene monomer forms a crosslinked structure during polymerization and the crosslinked structure is introduced into the surface of the water absorbing resin.

It should be noted here that the molar composition ratio of the internal crosslinking agent may be the same as or different from that of the water absorbing resin serving as a base polymer. Note, however, that it is preferable that the amount of crosslinkable monomers be larger than the amount of unsaturated ethylene monomers in a base polymer. For example, it is preferable that the amount of crosslinkable monomers be 1.01 to 1000 times the amount of the unsaturated ethylene monomers in the base polymer in mol %.

The amount of the crosslinkable unsaturated monomer to be used is preferably between 0.001 mol % and 100 mol %, more preferably between 0.01 mol % and 50 mol %, further preferably between 0.05 mol % and 30 mol %, particularly preferably between 0.1 mol % and 20 mol %, and most preferably between 0.5 mol % and 10 mol %, relative to the total amount of unsaturated ethylene monomers. It is particularly preferable that an acrylic acid (salt) serving as an unsaturated ethylene monomer be contained as a main component and the crosslinkable unsaturated monomer be used in combination with the acrylic acid (salt), because excellent water absorbing properties are achieved. Note that, instead of the crosslinkable unsaturated monomer, it is possible to use a compound having two or more unsaturated polymerizable groups other than a vinyl group and/or two or more reactive functional groups within a molecule.

(2-4) Other Monomer, Other Component

According to the production method 3 of the present invention, a radical polymerizable compound may be contained other than the acid radical-containing radical-polymerizable monomer. For example, the radical polymerizable compound other than the acid radical-containing radical-polymerizable monomer is preferably the foregoing unsaturated ethylene monomer (monomer) or a crosslinkable unsaturated monomer (crosslinking agent).

Further, it is possible to use the following radical polymerizable compound as a compound other than the unsaturated ethylene monomer and the internal crosslinking agent which are for use in production of the water absorbing resin and are described in the foregoing (a). That is, it is possible to use a radical polymerizable compound containing an unsaturated ethylene monomer that contains at least one hetero atom other than oxygen, which hetero atom is selected from the group consisting of nitrogen, sulfur, phosphorus, silicon and boron.

The amount of the radical polymerizable compound to be used is, but not particularly limited to, preferably between 0.1 and 20 parts by weight, more preferably between 0.5 and 15 parts by weight, further preferably between 1 and 10 parts by weight, particularly preferably between 1.5 and 8 parts by weight, and most preferably between 2 and 7 parts by weight, relative to 100 parts by weight of the water absorbing resin.

(3) Polyvalent Metal Compound

A polyvalent metal compound according to the production method 3 of the present invention is a compound containing a bivalent or multivalent metal atom. The polyvalent metal compound is preferably a water-soluble, polyvalent typical metal salt, and further preferably an inorganic or organic water-soluble aluminum salt. For example, aluminum sulfate ($Al_2(SO_4)_3$) is a polyvalent metal compound, because the aluminum sulfate is a compound containing trivalent aluminum (Al).

According to the production method 3 of the present invention, using such a polyvalent metal compound provides a water absorbing agent containing a polyvalent metal cation(s). This is the same as the water absorbing agent production method 2 in which a metallic soap is used. An oxide of a polyvalent metal (e.g., $Al_2O_3$), which serves as a polyvalent metal compound, is not soluble in water, and therefore cannot become a cation in water. Therefore, according to the present invention, a hydroxide or a salt, in particular a salt, of a polyvalent metal is used as a polyvalent metal compound. That is, an inorganic salt or organic salt, in particular a water-soluble inorganic or organic salt (a polyvalent metal salt of an organic acid), and further a water-soluble inorganic salt (a polyvalent metal salt of an inorganic acid), is used (these are described later).

A polyvalent metal component in the polyvalent metal compound, which component is usable in the production method 3 of the present invention, preferably contains at least one metal (polyvalent metal cation) selected from typical metals and transition metals of groups 4 to 11. Out of these polyvalent metal components, Mg, Ca, Ti, Zr, V, Cr, Mn, Fe, Co, Ni, Pd, Cu, Zn, Cd, and Al are more preferable. Out of these, Mg, Ca, Zn, and Al are further preferable, and Al is particularly preferable. It is preferable not to use transition metals, because some of them are polyvalent metal components having relatively high toxicity.

Further, the polyvalent metal compound is preferably soluble in water. According to the present invention, the "water-soluble" means that a compound dissolves, in 100 g of water (25° C.), in an amount of not less than 1 g and preferably not less than 10 g.

Examples of the polyvalent metal compound which can be used in the present invention include: water-soluble aluminum salts such as aluminium acetate, aluminum lactate, aluminum acrylate, aluminium chloride, polyaluminium chloride, aluminium sulfate, aluminium nitrate, bis aluminium potassium sulfate, and bis aluminium sodium sulfate; water-soluble alkaline earth metal salts such as calcium chloride, calcium nitrate, magnesium chloride, magnesium sulfate, and magnesium nitrate; and transition metal salts such as zinc chloride, zinc sulfate, zinc nitrate, copper sulfate, cobalt chloride, zirconium chloride, zirconium sulfate, and zirconium nitrate.

In a case where a polyvalent metal salt of an organic acid is used, examples of a particularly preferable anion include bases corresponding to the following acids: anisic acid, benzoic acid, formic acid, valeric acid, citric acid, glycolic acid, glycerol phosphate, glutaric acid, chloroacetic acid, chloropropionic acid, cinnamic acid, succinic acid, acetic acid, tartaric acid, lactic acid, pyruvic acid, fumaric acid, propionic acid, 3-hydroxypropionic acid, malonic acid, maleic acid, butyric acid, isobutyric acid, imidino acetic acid, malic acid, isothionic acid, methyl maleic acid, adipic acid, itaconic acid, crotonic acid, oxalic acid, salicylic acid, gluconic acid, gallic acid, sorbic acid, gluconic acid, and fatty acid, in particular stearic acid, adipic acid and p-hydroxy benzoic acid. Out of these bases, a base corresponding to tartaric acid and a base corresponding to lactic acid are preferable, and a base corresponding to lactic acid such as aluminum lactate or calcium lactate is most preferable.

Further, in view of solubility, it is preferable to use a salt having water of crystallization of those listed above. It is particularly preferable to use an aluminum compound, that is, a water-soluble inorganic salt of or water-soluble organic salt of aluminum. Out of these, aluminum sulfate is preferable, and a powder of a hydrate crystal of for example aluminum sulfate 14-18 hydrate can be used most preferably.

Note here that the polyvalent metal compound may remain in the water absorbing agent or may change for example through a reaction with a water absorbing resin. Note however that, usually, a resulting water absorbing agent will contain almost all the polyvalent metal cation(s) (e.g., aluminum cation) derived from the polyvalent metal compound. For example, the amount of the polyvalent metal cation(s) is between 0.001 wt % and 5 wt %, and further between 0.005 wt % and 3 wt %. These amounts can be easily determined in the method described later.

The amount of the polyvalent metal compound to be used is preferably between 0.001 and 20 parts by weight, more preferably between 0.01 and 10 parts by weight, and particularly preferably between 0.05 and 5 parts by weight, relative to 100 parts by weight of the solid content of a water absorbing resin composition. Since the amount of the polyvalent metal compound to be used is not less than 0.001 parts by weight, water absorbing properties such as absorbency against pressure are improved. Since the amount of the polyvalent metal compound to be used is not more than 20 parts by weight, no significant reduction occurs in free swelling capacity (CRC).

(4) Radical Polymerization Initiator

According to the production method 3 of the present invention, a radical polymerization initiator is preferably used in the step (a) of mixing the water absorbing resin, acid radical-containing radical-polymerizable monomer, polyvalent metal compound and water. Using a radical polymerization initiator cause a decrease in time taken to irradiate with activating light and the heating time in the step (b). The radical polymerization initiator is not particularly limited. Specifically, the radical polymerization initiator is for example a pyrolytic radical polymerization initiator or a photodegradable polymerization initiator for use in polymerization of the water absorbing resin.

(4-1) Pyrolytic Radical Polymerization Initiator

According to the production method 3 of the present invention, the amount of the pyrolytic radical polymerization initiator to be used is not particularly limited. Note however that, according to the present invention, the amount of the pyrolytic radical polymerization initiator is preferably between 0.01 and 20 parts by weight, more preferably between 0.05 and 10 parts by weight, and further preferably between 0.1 and 5 parts by weight, relative to 100 parts by weight of the water absorbing resin. Since the amount of the radical polymerization initiator falls within the above range, it is possible to obtain a water absorbing resin that is excellent in water absorbing properties, and further possible to achieve excellent productivity because the reaction speed is improved in surface treatment. The radical polymerization initiator may be used solely or two or more radical polymerization initiators may be used in combination.

The pyrolytic radical polymerization initiator is a compound that generates a radical when heated. Out of such compounds, a compound having a ten-hour half-life temperature of between 0° C. and 120° C. is preferable, a compound having a ten-hour half-life temperature of between 20° C. and 100° C. is more preferable, and a compound having a ten-hour half-life temperature of between 40° C. and 80° C. is particularly preferable. Since the ten-hour half-life temperature is not less than 0° C. (lower limit), the water absorbing agent suffers little degradation during storage. Since the ten-hour half-life temperature is not more than 120° C. (upper limit), a reaction proceeds efficiently and thus productivity can be improvised.

The pyrolytic radical polymerization initiator is relatively reasonable as compared to a compound that is sold as a photodegradable polymerization initiator, and does not necessarily require complete light shielding. Therefore, it is possible to simplify a production process and a production apparatus. Examples of typical pyrolytic radical polymerization initiators include: persulfates such as sodium persulfate, ammonium persulfate and potassium persulfate; hydrogen peroxide; and azo compounds such as 2,2'-azobis(2-amidinopropane)dihydrochloride, 2,2'-azobis[2-2(-imidazoline-2-yl) propane]dihydrochloride, and 2,2'-azobis(2-methylpropionitrile). Out of these, persulfates such as sodium persulfate, ammonium persulfate and potassium persulfate; and azo compounds such as 2,2'-azobis(2-amidinopropane)dihydrochloride, 2,2'-azobis[2-2(-imidazoline 2-yl)propane]dihydrochloride and 2,2'-azobis(2-methylpropionitrile), each of which has a ten-hour half-life temperature of between 40° C. and 80° C., are preferable. Out of these, it is particularly preferable to use a persulfate, because resulting absorbency against pressure, liquid permeability and free swelling capacity are all excellent. Not only one type of persulfate can be used, but also two or more persulfates having different counter ions can be used in combination.

(4-2) Other Polymerization Initiator

According to the production method 3 of the present invention, an oil-soluble photodegradable polymerization initiator and/or an oil-soluble organic peroxide may be used. Examples of the oil-soluble photodegradable polymerization initiator include benzoin derivatives, benzyl derivatives and acetophenone derivatives which are soluble in oil. Examples of the oil-soluble organic peroxide include: ketone peroxide, peroxyketal, hydroperoxide, dialkyl peroxide, peroxyester and peroxycarbonate which are soluble in oil. The photodegradable polymerization initiator may be a commercially-available product. Examples of a commercially-available photodegradable polymerization initiator include: IRGACURE (registered trademark) 184 (hydroxycyclohexyl-phenyl ketone) and IRGACURE (registered trademark) 2959 (1-[4-(2-hydroxyethoxy)-phenyl]-2-hydroxy-2-methyl-1-propane-1-one), which are manufactured by Ciba Specialty Chemicals Inc. The amount of the photodegradable polymerization initiator to be used is preferably between 0.0001 and 1 part by weight, more preferably between 0.001 and 0.5 part by weight, and further preferably between 0.005 and 0.1 part by weight, relative to 100 parts by weight of the water absorbing resin.

The radical polymerization initiator for use in the present invention can either be oil-soluble or water-soluble. An oil-soluble radical polymerization initiator is characterized in that its decomposition speed is less affected by pH and ionic strength as compared to a water-soluble radical polymerization initiator. Note however that, since the water absorbing resin is hydrophilic, it is more preferable to use a water-soluble radical polymerization initiator, in view of permeability into the water absorbing resin. Note that the "water-soluble" means the one that dissolves in water (25° C.) in an amount of not less than 1 wt %, preferably not less than 5 wt %, and more preferably not less than 10 wt %.

The water-soluble radical polymerization initiator is for example preferably a radical polymerization initiator selected from the group consisting of persulfates, hydrogen peroxides and azo compounds. Specific examples of the water-soluble radical polymerization initiator include: persulfates such as ammonium persulfate, sodium persulfate and potassium persulfate; hydrogen peroxide; and water-soluble azo compounds such as 2,2'-azobis-2-amidinopropane dihydrochloride and 2,2'-azobis[2-2(-imidazoline-2-yl)propane] dihydrochloride. Out of these, it is particularly preferable to use a persulfate, because absorbency against pressure, liquid permeability and free swelling capacity of the resulting surface-treated water absorbing resin are all excellent.

In addition to the radical polymerization initiator or instead of the radical polymerization initiator, it is possible to further use a percarbonate such as sodium percarbonate; and/or a peracetate such as peracetic acid or sodium peracetate, etc.

According to the present invention, in a case where another radical polymerization initiator such as a photodegradable polymerization initiator, which is other than the pyrolytic radical polymerization initiator, is used as needed in combination with the pyrolytic radical polymerization initiator, the amount of the another radical polymerization initiator to be used is between 0 and 20 parts by weight, preferably between 0 and 15 parts by weight, and particularly between 0 and 10 parts by weight, relative to 100 parts by weight of the water absorbing resin. Further, the amount of the another radical polymerization initiator to be used is smaller than the amount of the pyrolytic radical polymerization initiator. For example, the amount of the another radial polymerization initiator is not more than ½, further not more than ⅒, and particularly not more than ¹⁄₅₀ by weight of the amount of the pyrolytic radical polymerization initiator.

[7-B] Production Method of Fourth Embodiment (Water Absorbing Agent Production Method 3)

(1) Step of Mixing Water Absorbing Resin, Radical Polymerizable Monomer, Polyvalent Metal Compound and Water (Step (a))

According the surface treatment method of the present invention in the production method 3 of the present invention, an acid radical-containing radical-polymerizable monomer, a polyvalent metal compound and water are mixed with a water absorbing resin in the step (a).

In the step (a), there is no particular limitation on the order in which the radical polymerizable monomer, polyvalent metal compound, water, and if needed a radical polymerization initiator are mixed with the water absorbing resin. Accordingly, each of these constituents may be individually mixed with the water absorbing resin. Alternatively, an aqueous solution containing the radical polymerizable monomer, polyvalent metal compound and radical polymerization initiator may be prepared in advance, and the aqueous solution may be mixed with the water absorbing resin. Note however that, in order for the radical polymerizable monomer etc. to be evenly dispersed on the surface of the water absorbing resin, it is preferable to prepare an aqueous solution containing the radical polymerizable monomer, polyvalent metal compound and radical polymerization initiator in advance and then mix the aqueous solution with the water absorbing resin. Alternatively, the radical polymerizable monomer, polyvalent metal compound, radical polymerization initiator and the water absorbing resin may be mixed together to obtain a mixture, and thereafter the mixture may be mixed with water.

Note, however, that the scope of the present invention does not encompass the case where the polyvalent metal compound is added to the water absorbing resin after "the step of polymerizing the acid radical-containing radical-polymerizable monomer (i.e., the step (b), described later)". In this case, the absorbency against pressure (AAP) is not improved or is reduced.

A solvent in which the radical polymerizable monomer, polyvalent metal compound and if needed the radical polymerization initiator are dissolved is preferably water alone, although another solvent may be contained provided that their solubility is not lost. That is, it is preferable to use the radical polymerizable monomer and/or the polyvalent metal compound and/or the radical polymerization initiator in the form of an aqueous solution, in the absence of a hydrophobic organic solvent.

(2) Amount of Water to be Used

The amount of water to be mixed with the water absorbing resin in the mixing step (a) is preferably between 1 and 50 parts by weight, more preferably between 3 and 30 parts by weight, further preferably between 5 and 20 parts by weight, and particularly preferably between 6 and 15 parts by weight, relative to 100 parts by weight (equivalent to 100 wt % of solid content) of the water absorbing resin. An amount of water to be mixed falling within the above range is preferable, because (i) the reaction speed is improved in surface treatment carried out by irradiation with activating light and/or by heat treatment, (ii) the amount of energy needed is small in the drying step after the treatment by irradiation with activating light and/or the heat treatment, and further (ii) the water absorbing resin is hardly decomposed. In a case where the radical polymerizable monomer etc. are to be mixed in the form of an aqueous solution, the amount of water in the aqueous solution can be controlled so that the amount of water in a resulting water absorbing agent (in particular, the fourth water absorbing agent, further the first water absorbing agent) falls within the foregoing range.

It should be noted that how to mix water with the water absorbing resin is not necessarily limited to mixing the water in the form of an aqueous solution that contains a radical polymerizable monomer etc. For example, water may be mixed after a radical polymerizable monomer, a polyvalent metal compound, if needed a radical polymerization initiator, and the water absorbing resin are mixed with each other. Accordingly, a water absorbing agent may be obtained by (i) preparing a polymer by polymerizing a monomer component to obtain a hydrous gel crosslinked polymer and thereafter drying the hydrous gel crosslinked polymer until the hydrous gel crosslinked polymer has a moisture content that causes the resultant water absorbing agent to have the moisture content falling within the above range and then (ii) directly mixing a radical polymerizable compound, a polyvalent metal compound and if needed a radical polymerization initiator with the polymer.

(3) Mixing Auxiliary Agent

Meanwhile, in order to improve mixability of a water absorbing resin composition, it is preferable to add a mixing auxiliary agent to the water absorbing resin composition. Note here that water is not encompassed in the mixing auxiliary agent. When to add the mixing auxiliary agent is not particularly limited. The mixing auxiliary agent is preferably added during or before the step (a). Note here that the mixing auxiliary agent other than water is a water-soluble or water-dispersible compound that is other than radical polymerizable monomers, polyvalent metal compounds and radical polymerization initiators. The mixing auxiliary agent other than water is preferably a water-soluble or water-dispersible compound capable of suppressing aggregation by water of the water absorbing resin and capable of improving mixability of the water absorbing resin with an aqueous solution.

Specifically, surfactants, water-soluble polymers, hydrophilic organic solvents, water-soluble inorganic compounds, inorganic acids, inorganic salts, organic acids and organic salts exemplified in Patent Literature 30 each can be used as such a water-soluble or water-dispersible compound. Adding a mixing auxiliary agent other than water makes it possible to suppress aggregation by water of the water absorbing resin and thus to evenly mix an aqueous solution and the water absorbing resin. This makes it possible to evenly surface-treat the entire water absorbing resin when the water absorbing resin is subjected to treatment by irradiation with activating light and/or heat treatment in the subsequent step. It is preferable that a mixing auxiliary agent exemplified in the foregoing water absorbing agent production methods 1 and 2 be used as a mixing auxiliary agent also in the production method 3.

As described earlier, the amount of a mixing auxiliary agent to be added is not particularly limited, provided that the mixing auxiliary agent is capable of suppressing aggregation by water of the water absorbing resin and thus improving mixability of the water absorbing resin with an aqueous solution. For example, the amount of the mixing auxiliary agent to be added is between 0.001 and 40 parts by weight, more preferably between 0.01 and 10 parts by weight, and particularly preferably between 0.05 and 5 parts by weight, relative to 100 parts by weight of the water absorbing resin. Alternatively, according to the present invention, the mixing auxiliary agent may be used in an amount of preferably between 0 wt % and 40 wt %, more preferably between 0.01 wt % and 20 wt %, and further preferably between 0.05 wt % and 10 wt %, relative to the total amount of an aqueous solution.

In a case where a mixing auxiliary agent exemplified in Patent Literature 30 etc. is used, there is no particular limitation on how to use the mixing auxiliary agent. The mixing auxiliary agent may be used in powder form or may be used after being dissolved, dispersed or suspended in a solution. It is preferable that the mixing auxiliary agent be used in the form of an aqueous solution.

Further, in the case where the mixing auxiliary agent is used, there is no particular limitation on the order in which the mixing auxiliary agent is added. The mixing auxiliary agent can be mixed by any method such as (i) a method of adding the mixing auxiliary agent to the water absorbing resin in advance to obtain a mixture and thereafter adding an aqueous solution to the mixture or (ii) a method of dissolving the mixing auxiliary agent in an aqueous solution and then simultaneously mixing the mixing auxiliary agent and the aqueous solution with the water absorbing resin.

(4) Mixing Conditions

In the step (a) in accordance with the present invention, there is no particular limitation on the mixing conditions in which the water absorbing resin, a radial polymerizable monomer, a polyvalent metal compound, water, and if needed a radical polymerization initiator and a mixing auxiliary agent are to be mixed. For example, the mixing temperature in the step (a) is preferably between 0° C. and 150° C., more preferably between 10° C. and 120° C., and further more preferably between 20° C. and 100° C. Since the mixing temperature is not more than 150° C., it is possible to suppress deterioration by heat in the water absorbing resin. On the other hand, since the mixing temperature is not less than 0° C., it is possible to carry out stable operations without trouble such as condensation of water.

It should be noted that, in a case where the mixing step is carried out at high temperatures, the radical polymerization initiator reacts in response to heat even with low doses of irradiation. If this is the case, it is preferable to prevent excessive leakage of water vapor by for example sealing a mixing/irradiation system.

Further, the temperature of the water absorbing resin and the temperature of water before the step (a) are not particularly limited. For example, the temperature of the water absorbing resin before the step (a) is preferably between 0° C. and 150° C., more preferably between 10° C. and 120° C., and further more preferably between 20° C. and 100° C. Since the temperature of the water absorbing resin before the step (a) is not more than 150° C., it is possible to suppress deterioration by heat in the water absorbing resin. On the other hand, since the temperature of the water absorbing resin before the step (a) is not less than 0° C., it is possible to carry out stable operations without trouble such as condensation of water.

Further, the temperature of water before the step (a) is preferably between 5° C. and 80° C., more preferably between 10° C. and 60° C., and particularly preferably between 20° C. and 50° C. Since the temperature of water before the step (a) is not more than 80° C., it is possible to mix a sufficient amount of water with the water absorbing resin by preventing excessive evaporation of the water before the mixing step (a), and thus possible to bring about the effects of the present invention. On the other hand, since the temperature of water is not less than 5° C., it is possible to carry out stable operations without trouble such as condensation of water.

Further, the mixing time in the step (a) is not particularly limited, provided that those described above can be evenly mixed together. Specifically, the mixing time is preferably between 0.1 second and 60 minutes, more preferably between 1 second and 30 minutes, further preferably between 2 seconds and 20 minutes, and most preferably between 5 seconds and 10 minutes. If the mixing time is shorter than the lower limit, the water absorbing resin, a radical polymerizable monomer, a polyvalent metal compound and water etc. may not be evenly mixed. On the other hand, if the mixing time is longer than the upper limit and becomes excessive, the water excessively permeates into the water absorbing resin. This may inhibit the surface treatment to proceed, which surface treatment is carried out by irradiation with activating light and/or by heat treatment.

It should be noted that, when the water absorbing resin, radical polymerizable monomer, polyvalent metal compound and water are to be mixed together to obtain a water absorbing resin composition, these constituents can be mixed for example with use of an usual mixer such as a V-shaped mixer, a ribbon mixer, a screw-type mixer, a rotating disk mixer, an air mixer, a batch-type kneader, a continuous-type kneader, a paddle-type mixer, or a spade mixer.

(5) Step of Polymerizing Acid Radical-Containing Radical-Polymerizable Compound (Step (b))

The present invention includes the step of polymerizing, by use of radical generating means such as irradiation with activating light and/or heating, an acid radical-containing radical-polymerizable monomer mixed in the water absorbing resin. It is preferable that the acid radical-containing radical-polymerizable monomer be polymerized in its surface and/or shallow surface.

The polymerization makes the crosslink density higher in the shallow surface of the water absorbing resin than inside the water absorbing resin. This achieves excellent properties desired for practical use of the water absorbing resin, such as excellent absorbency against pressure.

The following description discusses two polymerization methods h and i: (5-1) Irradiation with activating light and (5-2) Heating.

(5-1) Irradiation with Activating Light (Polymerization Method h in Water Absorbing Agent Production Method 3)

According to the present invention, irradiation with activating light may be carried out (i) while the water absorbing resin, radial polymerizable monomer, polyvalent metal compound and water are being mixed or (ii) after two or more of the above are mixed together. Note however that, in order to carry out the surface treatment uniformly, it is preferable to (a) obtain a water absorbing resin composition that contains the water absorbing resin, radical polymerizable monomer, polyvalent metal compound and water and thereafter (b) irradiate such a water absorbing resin composition with activating light.

The activating light is for example one or more types selected from ultraviolet rays, electron beams and gamma rays, and is preferably an ultraviolet ray and/or an electron beam. Taking into consideration an effect caused by the activating light on human bodies, the activating light is more preferably an ultraviolet ray, further preferably an ultraviolet ray having a wavelength of not more than 300 nm, and particularly preferably an ultraviolet ray having a wavelength between 180 nm and 290 nm. The irradiation is carried out under the condition in which, in a case where an ultraviolet ray is used, the irradiation intensity is preferably between 3 and 1000 [mW/cm$^2$] and the irradiance is preferably between 100 and 10000 [mJ/cm$^2$].

The ultraviolet ray can be emitted with use of for example a high-pressure mercury lamp, a low-pressure mercury lamp, a metal halide lamp, a Xenon lamp or a halogen lamp. How the ultraviolet ray is emitted is not particularly limited. Therefore, some other radiation or wavelength may be included provided that a ultraviolet ray, preferably a ultraviolet ray having a wavelength of not more than 300 nm, is emitted. It should be noted that, in a case where an electron beam is used, it is preferable that the acceleration voltage be between 50 kV and 800 kV and the absorbed dose be between 0.1 Mrad and 100 Mrad.

The irradiation time during which the water absorbing resin is irradiated with activating light depends on the amount of the water absorbing resin to be treated. In a case of the method described in the following Examples, the irradiation time may be preferably not less than 0.1 minute but less than 60 minutes, more preferably not less than 0.5 minute but less than 20 minutes, further preferably not less than 0.5 minute but less than 5 minutes, and particularly preferably not less than 1 minute but less than 3 minutes. In a case where a conventional surface crosslinking agent is used, for example an irradiation time of more than 60 minutes is required. That is, the method in accordance with the present invention makes it possible to shorten the time taken to carry out the surface treatment, as compared to a conventional method in which the crosslink density is the same as in the present invention.

According to the present invention, it is not necessary to carry out heating when carrying out the surface treatment by irradiation with activating light. Note, however, that the irradiation with activating light can be carried out during heating. This makes it possible to obtain a water absorbing resin that is excellent in water absorbing properties. The heating temperature is preferably between 0° C. and 150° C., more preferably between 10° C. and 120° C., further preferably between room temperature and 100° C., and particularly preferably between 50° C. and 100° C.

It should be noted that irradiation with activating light may cause radiant heat to be emitted. If this is the case, the irradiation with activating light is to be carried out during heating. According to the present invention, since the surface treatment is carried out by irradiation with activating light, the heating is carried out in an auxiliary manner. Therefore, the temperature for surface treatment can be set to be lower than that for a conventional surface treatment. The heating is carried out by for example (i) a method of introducing heated air into an activating light irradiator, (ii) a method of heating by enclosing the activating light irradiator with a jacket etc., (iii) a method of heating by utilizing radiant heat emitted when irradiation with activating light is carried out or (iv) a method of irradiating, with activating light, a water absorbing resin having been heated in advance.

It is preferable that the water absorbing resin be irradiated with activating light with stirring. Stirring makes it possible to irradiate, evenly with activating light, a water absorbing resin composition containing the water absorbing resin, radical polymerizable monomer, polyvalent metal compound and water. The water absorbing resin can be stirred, when being irradiated with activating light, with use of for example a vibration-type mixer, a vibration feeder, a ribbon mixer, a conical ribbon mixer, a screw-type mixing extruder, an air mixer, a batch-type kneader, a continuous-type kneader, a paddle-type mixer, a high-speed fluid-type mixer, a floating flow-type mixer or the like.

Alternatively, the water absorbing resin composition may be caused to flow in an apparatus having a shape of a cylinder or a box etc., and the apparatus may be externally irradiated with activating light. In order to cause the mixture to flow, the pressure of a gas such as air may be utilized like those used in pneumatic transportation of powder. In a case where air is used, it is preferable to humidify the air in order to prevent the water absorbing resin composition from drying. It is possible to carry out the surface treatment evenly within a short period of time by irradiating the apparatus with activating light from multiple directions. Note that the apparatus is not particularly limited on its constituents and therefore may be constituted by any material, provided that the material does not inhibit irradiation of the water absorbing resin composition with the activating light. The apparatus is constituted by for example quartz glass etc.

It has been generally known that a reaction in which a radical acts as an active center is inhibited by oxygen. In this regard, according to the production method of the present invention, the physical properties of the surface-treated water absorbing resin did not decrease even though oxygen was present inside the system. This demonstrates that it is not essential that the atmosphere be inert atmosphere during irradiation with activating light.

Note however that, by causing the atmosphere during the irradiation with activating light to be inert atmosphere and/or removing dissolved oxygen in agents that are to be mixed with the water absorbing resin in the step (a), it is possible to shorten the time taken to irradiate with activating light. This is preferable because this makes it possible to achieve high productivity and low costs. Further, this makes it possible to reduce the amount of a radical-polymerizable monomer(s) remaining in the surface-treated water absorbing resin, and thus possible to cause the water absorbing resin to be suitably used in disposable diapers etc. in the field of sanitary materials. Moreover, this provides the same effects also in the following (5-2), i.e., in the surface treatment by heating (polymerization method i in water absorbing agent production method 3).

(5-2) Heating (Polymerization Method i in Water Absorbing Agent Production Method 3)

As described earlier, the acid radical-containing radical-polymerizable monomer mixed with the water absorbing resin can be polymerized by heating. In a case where the polymerization is carried out by heating only, it becomes unnecessary to separately provide an activating light irradiator. Accordingly, a production apparatus is excellent in design. Further, it becomes possible to improve, at low cost in a safe manner, the water absorbing properties (in particular, absorbency against pressure) of a resulting surface-treated water absorbing resin.

The mixture obtained in the foregoing step (a) may be prepared under the same conditions as those for the polymerization by irradiation with activating light, and a radical polymerization initiator is not essential. It is preferable that an acid radical-containing radical-polymerizable monomer, a polyvalent compound, water and a radical polymerization initiator be mixed with the water absorbing resin in respective predetermined amounts relative to the amount of the water absorbing resin. It is preferable that the mixture then be heated at a temperature falling within a predetermined range.

In a case where the step (b) is a step of heating a mixture, the mixture obtained in the step (a) can be prepared under the conditions different from those for the polymerization by irradiation with activating light. This makes it possible to prevent generation of radicals. The following description discusses a preferred embodiment for heating.

According to the preferred embodiment of the present invention, a water absorbing resin is mixed with an aqueous solution containing an acid radical-containing radical-polymerizable monomer, a polyvalent metal compound and a radical polymerization initiator (hereinafter, such an aqueous solution is also referred to as a "treatment liquid") to obtain a mixture, i.e., a water absorbing resin composition. Then, the water absorbing resin composition is subjected to heat treatment. This seems to cause a crosslinked structure to be introduced in the surface of the water absorbing resin. Note, however, that the technical scope of the present invention is not limited to such an embodiment. Therefore, there is no particular limitation on the order in which various components existing in a reaction system are to be added and on timings of addition of the various components and heat treatment. For example, a radical polymerizable monomer, a polyvalent metal compound, water and a radical polymerization initiator may be separately added to the water absorbing resin (base polymer). Alternatively, these components may be added to the water absorbing resin (base polymer) during heat treatment.

According to the present invention, there is no particular limitation on a difference between moisture contents before and after the step of polymerizing the acid radical-containing radical-polymerizable monomer (hereinafter, such a step is also referred to as a "surface treatment step"). Note, however, that it is preferable that the moisture content after the surface treatment step be not lower than that before the surface treatment step, and more preferable that the moisture content after the surface treatment step be higher than that before the surface treatment step.

(5-2-1) Heating Temperature

The heat treatment is carried out preferably at a temperature of not less than 80° C. but not more than 250° C., more preferably at a temperature between 90° C. and 180° C., and further preferably at a temperature between 100° C. and 150° C. A heating temperature of not less than 80° C. allows the surface treatment to proceed efficiently. On the other hand, a heating temperature of not more than 250° C. can prevent deterioration by heat in the water absorbing resin. Heating the water absorbing resin under the above condition makes it possible to produce a surface-treated water absorbing resin at low cost in a safe manner, which water absorbing resin is excellent in water absorbing properties (in particular, absorbency against pressure and liquid permeability).

When the surface treatment of a water absorbing resin is to be carried out by heating, the surface treatment may be carried out by heating a water absorbing resin that contains the foregoing components. An atmosphere in which the heat treatment is carried out is not limited to a particular kind, and it is preferable that heating be carried out in an atmosphere of relatively high humidity. Specifically, it is preferable to carry out heating in saturated steam or in superheated steam. In a case of heating at a temperature of not less than 100° C., it is preferable that an atmosphere be filled with superheated steam, and more preferable that the water absorbing resin be directly heated with use of superheated steam.

(5-2-2) Pressure

The pressure of an atmosphere during the heat treatment is not particularly limited, and therefore may be reduced pressure, normal pressure or increased pressure. The pressure is preferably between 1013 hPa and 43030 hPa, more preferably between 1013 hPa and 14784 hPa, further preferably between 1013 hPa and 10498 hPa, and particularly preferably between 1013 hPa and 4906 hPa. Further, the relative humidity of the atmosphere is preferably between 50% RH and 100% RH, more preferably between 70% RH and 100% RH, further preferably between 90% RH and 100% RH, and particularly preferably between 95% RH and 100% RH, and most preferably 100% RH (saturated steam).

Further, the oxygen concentration in an atmosphere during the heat treatment is preferably between 0% by volume and 25% by volume, more preferably between 0% by volume between 15% by volume, further preferably between 0% by volume and 10% by volume, further more preferably between 0% by volume and 5% by volume, particularly preferably between 0% by volume and 1% by volume, and most preferably between 0% by volume and 0.5% by volume. It is preferable that the oxygen concentration in the atmosphere be controlled to relatively low concentration like above, because oxidative degradation in the water absorbing resin during the heat treatment can be prevented.

(5-2-3) Specific Embodiment of Heating Time and Irradiation with Activating Light The heating time for the heat treatment is not particularly limited either. The heating time is preferably between 1 minute and 90 minutes, more preferably between 2 minutes and 60 minutes, and further preferably between 3 minutes and 30 minutes. A heating time of not less than 1 minute allows the crosslinked structure to be introduced in the surface of the water absorbing resin. On the other hand, a heating time of not more than 90 minutes can prevent the water absorbing resin from deteriorating by heating.

Further, according to the surface treatment step in a surface treatment method in accordance with the present invention, a treatment to irradiate with activating light such as a radiation, an electron beam, an ultraviolet ray, or an electromagnetic beam etc. may be carried out in addition to the foregoing heat treatment.

An apparatus for use in the heat treatment to surface-treat the water absorbing resin is not particularly limited, and can be a known dryer. For example, a heat-conduction-type dryer, a heat-radiation-type dryer, a hot-air-heat-conduction-type dryer or a dielectric-heating-type dryer is preferably used. Specifically, a belt-type dryer, an agitated trough dryer, a fluidized bed-type dryer, an air jet dryer, a rotating dryer, a kneading dryer, an infrared dryer and an electron beam dryer can be preferably used.

(6) Other Treatment

Heat treatment may be carried out not only in the polymerization method i but also in the polymerization method h in the water absorbing agent production method 3. That is, after irradiation with activating light, the water absorbing resin may be subjected to heat treatment at a temperature between 50° C. and 250° C. to be dried etc. as needed.

Further, after the irradiation with activating light and/or heating, a surface crosslinkage may be formed with use of a surface crosslinking agent such as a well-known polyhydric alcohol, polyhydric epoxy compound or alkylene carbonate.

In addition, an additive may be added in an amount between 0.001 and 20 parts by weight, more preferably between 0.01 and 10 parts by weight, and particularly preferably between 0.1 and 5 parts by weight, relative to 100 parts by weight of the water absorbing resin. Examples of the additive include: water-insoluble fine particles such as hydrophilic amorphous silica; reducing agents; antimicrobial agents; deodorizers; chelating agents; and polyvalent metal compounds.

[7-C] Particulate Water Absorbing Agent of Fourth Embodiment (Fourth Water Absorbing Agent)

According to the present invention, it is possible to produce a novel surface-treated water absorbing resin by carrying out, with respect to a water absorbing resin, both (i) a surface treatment method including polymerizing an acid radical-containing radical-polymerizable monomer and (ii) a surface treatment method using a polyvalent metal compound. The present invention improves not only absorbency against pressure (AAP) but also vertical diffusion absorbency under pressure (VDAUP) of a resulting water absorbing resin. The vertical diffusion absorbency under pressure (VDAUP) is a novel parameter.

That is, according to for example the foregoing production method in which polymerization is carried out in the presence of water in an amount between 5 wt % and 20 wt % relative to the amount of the water absorbing resin, it is possible to provide a novel water absorbing resin that is particularly high in water absorbency and also in moisture content, in particular a high-moisture-content particulate water absorbing agent that is high in vertical diffusion absorbency under pressure (VDAUP).

The fourth water absorbing agent has a VDAUP satisfying the following condition. It is preferable that each of the first to fourth water absorbing agents also have a VDAUP satisfying the following condition. It is possible to obtain the first and fourth water absorbing agents having a novel VDAUP satisfying the following condition by carrying out, in for example the water absorbing agent production methods 1 to 3, control such that a particulate water absorbing agent obtained by preferably mixing a polyvalent metal compound or a metallic soap (an organic salt of a polyvalent metal) satisfies the following requirements (1), (2) and (4):

(1) a polyvalent metal cation is contained in an amount between 0.001 wt % and 5 wt % relative to the amount of the particulate water absorbing agent;

(2) an absorbency without pressure (CRC) of the particulate water absorbing agent is not less than 28 (g/g) and an absorbency against pressure (AAP 4.83 kPa) of the particulate water absorbing agent is not less than 10 (g/g); and (4) a moisture content of the particulate water absorbing agent is between 5 wt % and 20 wt %.

The present invention provides a surface-treated polyacrylic acid (salt) water absorbing agent (which has been surface-treated preferably with a polyvalent metal compound, particularly preferably with a water-soluble aluminum salt), which water absorbing agent (i) satisfies the inequalities: CRC≥28 [g/g] (preferably CRC≥30 [g/g]), AAP (4.83 kPa)≥10 [g/g] (preferably AAP (4.83 kPa)≥15 [g/g]); and VDAUP≥15 g (preferably VDAUP≥25 g) and (ii) has a moisture content between 5 wt % and 20 wt %. Further, it is preferable that the water absorbing agent satisfy the inequality: AAP (2.07 kPa)≥28 [g/g].

It is preferable that the degree of neutralization of the polyacrylic acid (salt) water absorbing resin be lower in surface than inside thereof. It should be noted that the degree of neutralization inside and in the surface of particles of the water absorbing resin can be calculated by the method described in International Publication No. 2009/048160 or the method described in US Patent Application Publication No. 2008/0027180.

(Vertical Diffusion Absorbency Under Pressure VDAUP)

According to the present invention, it was found that vertical diffusion absorbency under pressure (VDAUP), which is a novel parameter indicative of a physical property, plays an important role in disposable diapers. There have conventionally been proposed, mainly for use in disposable diapers, water absorbing resins in which a lot of physical properties such as absorbency against pressure (AAP), water absorbency (CRC) and liquid permeability (GBP, SFC) etc. are controlled. The inventors of the present invention found out the vertical diffusion absorbency under pressure (VDAUP) which is closely correlated to physical properties of diapers which properties cannot be evaluated with the above parameters, and developed a particulate water absorbing agent of the present invention.

Specifically, according to the fourth water absorbing agent (and further the first to third water absorbing agents), the vertical diffusion absorbency under pressure VDAUP is preferably not less than 15 g, more preferably not less than 20 g, further preferably not less than 25 g, further more preferably not less than 30 g, particularly preferably not less than 33 g, and most preferably not less than 35 g. In order to be balanced with the other physical properties, the upper limit of the VDAUP is not more than 100 g, and further about not more than 80 g. The vertical diffusion absorbency under pressure is measured by the method described in Examples.

The vertical diffusion absorbency under pressure (VDAUP) is a parameter based on a novel idea. It was found that the VDAUP was closely correlated to Re-Wet and absolute absorbency in diapers.

The absorbency against pressure (AAP) is defined as a ratio by mass of 0.900 g of a water absorbing resin to an absorbed liquid (i.e., defined as water absorbency g/g). On the other hand, the vertical diffusion absorbency under pressure (VDAUP) is measured in the same manner as in the method of measuring the AAP except that the amount of an absorbed liquid (absolute amount (g)) is measured with use of 10.000 g of a water absorbing resin (i.e., defined as absolute amount (g)).

That is, the VDAUP is measured with use of a water absorbing resin having more than 11 times (=10.0/0.9) as much basis weight per unit area as those used in measuring the AAP. Therefore, interlayer liquid diffusibility and interlayer liquid permeability in swollen gel layers play important roles for the liquid to be evenly absorbed in an entire sample. That is, the vertical diffusion absorbency under pressure serves as an index indicative of not only the absorption (g) under pressure per sample, but also the liquid diffusibility and liquid permeability in an absorbent core for practical use, in particular in an absorbent core having a high water absorbing resin concentration. The following Examples also describe the fact that the VDAUP is closely correlated to physical properties of diapers.

(Moisture Content)

Further, according to a surface-treated water absorbing resin obtained in the present invention, it is preferable that the moisture content of the water absorbing resin after the surface treatment step be higher than that before the surface treatment step. In particular, it is preferable that the water absorbing resin be subjected to heat treatment with use of saturated steam.

The moisture content of the particulate water absorbing agent of the fourth embodiment (the fourth water absorbing agent) obtained by for example the water absorbing agent production method 3, i.e., the moisture content of a surface-treated water absorbing resin, falls within the range described in the (6-6) of [6].

The moisture content of each of the first, third, and fourth (and further the second) particulate water absorbing agents is between 5 wt % and 20 wt %, preferably between 5 wt % and 18 wt %, more preferably between 6 wt % and 18 wt %, further preferably between 7 wt % and 15 wt %, and particularly preferably between 8 wt % and 13 wt %. A moisture content of less than 5 wt % is not preferable, because sufficient stability to shock is not achieved, and fluidity after moisture absorption decreases and thus handleability decreases. On the other hand, a moisture content of more than 20 wt % is not preferable, because water absorbing properties (e.g., AAP, CRC) decrease and the fluidity after moisture absorption decreases.

To what extent the moisture content after the surface treatment step is higher than that before the surface treatment step is not particularly limited. The moisture content after the surface treatment step is higher preferably by 0.1 wt % to 40 wt %, more preferably by 0.5 wt % to 30 wt %, further preferably by 1 wt % to 20 wt %, and particularly preferably by 2 wt % to 15 wt %, in terms of absolute value of the moisture content.

Since the moisture content and an increase in moisture content of the particulate water absorbing agent are not less than the lower limits of the above ranges, the operation and effect of the present invention are fully achieved and the shock resistance (Patent Literatures 17, 20 and 32) is sufficiently improved. Unlike Patent Literatures 17, 20 and 32, according to the present invention, it is possible to provide a water absorbing resin having a high absorbency against pressure (AAP) and a high rate of water absorption (Vortex), and having a predetermined amount of water (preferably 0.01 wt % to not more than 20 wt %). Accordingly, it is possible to obtain a surface-treated particulate water absorbing agent which is excellent in water absorbing properties such as absorbency against pressure and liquid permeability. On the other hand, since the moisture content and an increase in moisture content are not more than the upper limits of the foregoing ranges, it is possible to prevent a reduction in water absorbing properties, which reduction is caused by increase in moisture content.

(Residual Monomer)

As shown in Patent Literature 33, surface crosslinking seems to result in an increase in amount of residual monomers in the fourth water absorbing agent (and further the first to third water absorbing agents); however, according to the present invention, it is possible to achieve both the high physical properties and the small number of residual monomers, which are in a trade-off relationship. That is, according to a surface-treated water absorbing resin obtained in the present invention, the amount of an acid radical-containing radical-polymerizable compound, which remains particularly in a case where irradiation with activating light is carried out, is dramatically reduced. The amount of the acid radical-containing radical-polymerizable compound is reduced to preferably not more than 500 ppm, more preferably not more than 300 ppm, further preferably not more than 200 ppm, and particularly preferably not more than 100 ppm, relative to the water absorbing resin. Such a water absorbing resin is suitably usable in disposable diapers etc. in the field of sanitary materials.

(Absorbency Against Pressure AAP)

The AAP 4.83 kPa of the particulate water absorbing agent of the fourth embodiment (the fourth water absorbing agent), i.e., the AAP 4.83 kPa of a surface-treated water absorbing resin, falls within the range described in the foregoing (6-1) of [6].

Further, the absorbency against pressure AAP 2.03 kPa of the fourth (and further the first to third) water absorbing agent(s) is preferably not less than 25 [g/g], further not less than 28 [g/g], and particularly not less than 30 [g/g]. There is no particular upper limit on the absorbency against pressure AAP 4.83 kPa and the AAP 2.03 kPa. Note however that, in order to be balanced with the other physical properties, the upper limit is not more than 40 [g/g], and further not more than about 35 [g/g]. The absorbency against pressure is measured in the method described in Examples.

(CRC)

The CRC of the particulate water absorbing agent of the fourth embodiment (the fourth water absorbing agent), i.e., the CRC of a surface-treated water absorbing resin, falls within the range described in the foregoing (6-3) of [6].

(Particle Size)

The particle size of the particulate water absorbing agent of the fourth embodiment (the fourth water absorbing agent), i.e., the particle size of a surface-treated water absorbing resin, falls within the range described in the foregoing (6-5) of [6].

The powder is obtained for example in the form of spheres, in the form of irregular fragments (obtained by the pulverization step after the aqueous polymerization), in the form of substantial spheres or in the form of granulated (combined) particles. In view of the rate of water absorption, the powder is preferably in the form of irregular fragments (obtained by the pulverization step after the aqueous polymerization).

(Other)

A method in accordance with the present invention brings about an effect of granulating fine powders generated during production of a water absorbing resin, when surface-treating the water absorbing resin. Accordingly, even if a water absorbing resin that has not yet been surface-treated contains fine powders, it is possible to obtain a surface-crosslinked water absorbing resin containing less fine powders. This is because the fine powders contained are granulated by the surface treatment method in accordance with the present invention.

Further, according to the present invention, it is possible to sufficiently surface-treat the water absorbing resin even at reaction temperatures around room temperature, depending on conditions. Further, a resulting surface-treated water absorbing resin is very high in properties desired for the water absorbing resin, such as water absorbency, liquid permeability, rate of absorption, gel strength and suction etc. In addition, the amount of impurities such as residual monomers is small. Accordingly, a water absorbing resin obtained by the present invention is suitably used as a sanitary cotton or a disposable diaper which cause little Re-Wet and little leakage or as a sanitary material which absorbs other bodily fluids.

[8] Absorbent Core, Absorbing Article

A particulate water absorbing agent of the present invention is used for absorbing water, and is widely used as an absorbent core or an absorbing article. The particulate water absorbing agent is particularly suitably used as a sanitary material for absorbing bodily fluids such as urine and blood. By using the particulate water absorbing agent of the present invention in an absorbent core or an absorbing article, the absorbent core not only (i) fully demonstrates the properties inherent to the water absorbing agent in the absorbent core by virtue of excellent shock resistance and high absorbing properties (e.g., AAP, CRC) but also (ii) provides excellent effects on the Re-Wet and the rate of absorption of the absorbent core by virtue of excellent blendability with tissue such as pulp.

An absorbent core and an absorbing article of the present invention each contain a particulate water absorbing agent of the present invention.

As used herein, the absorbent core means a shaped absorptive material which contains as main components a particulate water absorbing agent and hydrophilic tissue. The content (core concentration) of the particulate water absorbing agent in the absorbent core relative to the total weight of the particulate water absorbing agent and the hydrophilic tissue is between 20 wt % and 100 wt %, more preferably between 25 wt % and 90 wt %, particularly preferably between 30 wt % and 80 wt %, and most preferably between 40 wt % and 80 wt %. As the core concentration in the absorbent core increases, the absorbent core and the absorbing article etc. become more susceptible to the water absorbing properties of the particulate water absorbing agent during their production.

The absorbing article is constituted by the absorbent core, a top sheet having liquid permeability, and a back sheet having no liquid permeability. The absorbing article is made by for example (i) producing an absorbent core (core) by blending the particulate water absorbing agent with a fiber base such as hydrophilic tissue or by sandwiching the particulate water absorbing agent between fiber bases and (ii) sandwiching the absorbent core between a top sheet having liquid permeability and a back sheet having no liquid permeability. After that, an elastic material, a diffusion layer and/or an adhesive tape etc. are/is provided as needed to obtain an absorbing article such as a diaper for adults or a sanitary napkin. In this case, the absorbent core is compression-molded to have a density of between 0.06 and 0.50 [g/cm$^3$] and a basis weight of between 0.01 and 0.20 [g/cm$^3$]. Examples of the fiber base to be used include: hydrophilic tissue such as fractured wood pulp; cotton linter and crosslinked cellulose fiber; rayon; cotton; wool; acetate; vinylon and the like. The fiber base is preferably those air-laid.

EXAMPLES

The following description more specifically discusses the present invention with reference to Examples and Comparative Examples. Electrical appliances etc. used in Examples and Comparative Examples were all operated at 100 V and 60 Hz. Further, unless otherwise stated, each physical property was measured at room temperature (25±2° C.) with a relative humidity of 50% RH.

It should be noted that physical properties of a particulate water absorbing agent of the present invention are defined by the evaluation methods described below. Further note that, for convenience of description, the term "parts by weight" may be shortened to "parts" and the term "liter" may be shortened to "L".

[Evaluation Method 1] Centrifuge Retention Capacity (CRC)

0.200 g (referred to as weight W0 [g]) of water absorbing resin particles or particulate water absorbing agent is placed uniformly in a bag (85 mm×60 mm) made of nonwoven fabric (manufactured by NANGOKU PULP INDUSTRY CO., LTD, product name: Heatlon Paper Type: GSP-22), and the bag was heat-sealed. After that, the bag was immersed in a large excess (usually, about 500 ml) of 0.90 wt % solution of sodium chloride at room temperature. After 30 minutes, the bag was pulled out, and water was spun off with a centrifugal force (250 G) described in ERT 441.2-02 for 3 minutes, with use of a centrifugal separator (manufactured by KOKUSAN Co. Ltd., Centrifuge: Type H-122). After that, the weight W1 [g] of the bag was measured.

The same operations were carried out except that neither the water absorbing resin particles nor the particulate water absorbing agent was placed in the bag, and the weight W2 [g] of the bag was measured. The centrifuge retention capacity (CRC) was calculated from the W0 [g], W1 [g] and W2 [g] according to the following equation.

$$CRC[g/g] = \{(W1-W2)/W0\} - 1 \qquad \text{[Math. 1]}$$

[Evaluation Method 2] Absorbency Against Pressure (AAP 4.83 kPa)

The absorbency against pressure (AAP 4.83 kPa) was measured in accordance with ERT 441.2-02.

Figure 2:
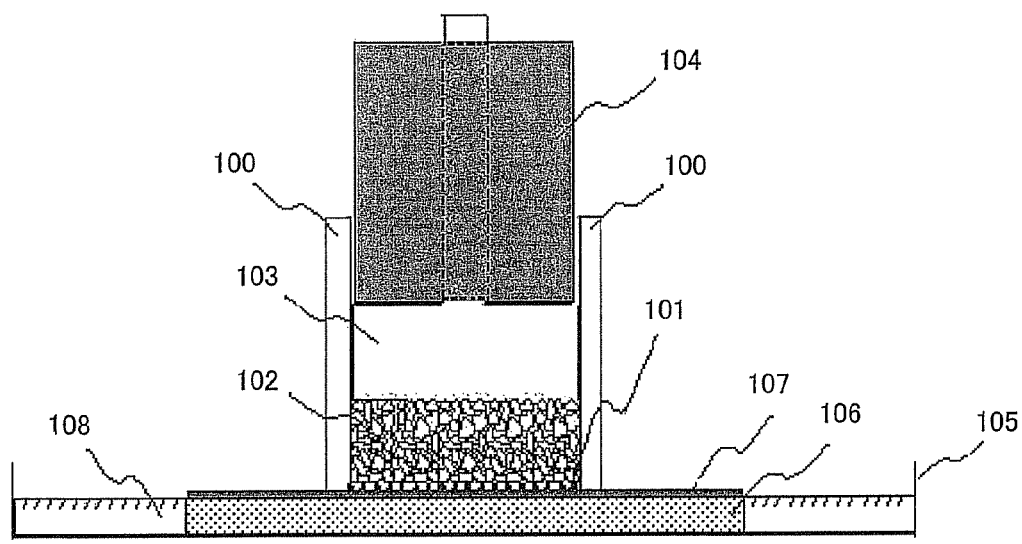
FIG. 2 is a side view schematically illustrating an apparatus for measuring AAP (absorbency against pressure), which is one of the physical properties of a water absorbing resin.

0.9 g (referred to as weight W3 [g]) of water absorbing resin particles or particulate water absorbing agent was placed in a measuring apparatus, and the total weight W4 [g] of the measuring apparatus was measured. Next, a 0.9 wt % solution of sodium chloride was allowed to be absorbed into the water absorbing resin particles or the particulate water absorbing agent under a pressure of 4.83 kPa. After 1 hour, the total weight W5 [g] of the measuring apparatus was measured. The absorbency against pressure (AAP 4.83 kPa) was calculated from the W3 [g], W4 [g] and W5 [g] according to the following equation. (Refer to FIG. 2 for the apparatus.)

$$AAP[g/g]=(W5-W4)/W3 \quad \text{[Math. 2]}$$

Absorbency against pressure (AAP 2.07 kPa) was measured in the same manner, except that the pressure applied on the water absorbing resin particles or the particulate water absorbing agent was 2.07 kPa.

[Evaluation Method 3] Weight Median Particle Size (D50) and Logarithmic Standard Deviation (σζ) of Particle Size Distribution The weight median particle size (D50) and the logarithmic standard deviation (σζ) of particle size distribution were measured in accordance with the measurement method disclosed in the International Publication No. 2004/069404.

Water absorbing resin particles or a particulate water absorbing agent was classified with use of JIS standard sieves (JIS Z8801-1 (2000)) having respective mesh opening sizes of 850 μm, 710 μm, 600 μm, 500 μm, 425 μm, 300 μm, 212 μm, 150 μm, 106 μm and 45 μm or sieves equivalent to the above, and residual percentages R were plotted on logarithmic graph paper. Then, a particle size satisfying R=50 wt % was read as the weight median particle size (D50).

The logarithmic standard deviation (σζ) of particle size distribution is represented by the following equation. The smaller the value, the narrower the particle size distribution. Note that, according to the present invention, it is essential to use the foregoing JIS standard sieves to measure and define the $$\sigma\zeta=0.5\times ln(X2/X1) \quad \text{[Math. 3]}$$

In the equation, X1 represents a particle size satisfying R=84.1 wt %, and X2 represents a particle size satisfying R=15.9 wt %.

[Evaluation Method 4] Amount of Generation of Coarse Particles (Aggregated Particles)

(i) The amount of particles remaining on a JIS standard sieve 850 μm was measured before and after water was added to a water absorbing resin powder to obtain a water absorbing agent. An increase [wt %] in the amount of the particles remaining on the JIS standard sieve 850 μm, which amount increased by addition of water, was used as the amount [wt %] of generated coarse particles (aggregated particles).

[Evaluation Method 5] Moisture Content

The moisture content defines the amount of water contained in water absorbing resin particles or a particulate water absorbing agent. 1 g of water absorbing resin particles or particulate water absorbing agent is dried at 180° C. for 3 hours, and a decrease in the weight of the water absorbing resin particles or the particulate water absorbing agent is measured. The ratio (wt %) of the weight after drying to the weight before drying serves as the moisture content.

The moisture content was measured in the following manner. 1 g (referred to as weight W6 [g]) of water absorbing resin particles or particulate water absorbing agent was placed in an aluminum cup (whose weight is referred to as weight W7 [g]) having a bottom surface of about 5 cm in diameter, and was allowed to stand in a calm dryer at 180° C. After 3 hours, the total weight (referred to as weight W8 [g]) of the aluminum cup and the water absorbing resin was measured, and the moisture content was calculated according to the following equation.

$$\text{Moisture content}[wt \%]=\{W6-(W8-W7)\}/W6\times100 \quad \text{[Math. 4]}$$

[Evaluation Method 6] Paint Shaker Test (PS)

The paint shaker test (PS) is carried out in the following manner. In a glass container which is 6 cm in diameter and 11 cm in height, (i) 10 g of glass beads of 6 mm in diameter and (ii) 30 g of water absorbing resin particles or water absorbing agent are placed, and the glass container is attached to a paint shaker (manufactured by Toyo Seiki Seisaku-sho, Ltd., Product No. 488). Then, the glass container is shaken at 800 [cycle/min] (CPM) for 30 minutes. Details of the apparatus are disclosed in Japanese Patent Application Publication, Tokukaihei, No. 9-235378. After the shaking, the glass beads are removed with use of a JIS standard sieve having a mesh opening size of 2 mm. In this way, damaged water absorbing resin particles or a damaged water absorbing agent are/is obtained.

It should be noted that (i) a paint shaker test in which the shaking is carried out for 30 minutes may be specifically referred to as a paint shaker test 1 and (ii) a paint shaker test in which the shaking is carried out for 10 minutes may be specifically referred to as a paint shaker test 2. Note however that, unless otherwise noted, those merely described as a "paint shaker test" indicate the paint shaker test 1 in which the shaking is carried out for 30 minutes.

[Evaluation Method 7] Fluidity after Moisture Absorption (Blocking Rate after Moisture Absorption)

About 2 g of water absorbing resin particles or particulate water absorbing agent was spread uniformly in an aluminum cup which is 52 mm in diameter, and was allowed to stand for 1 hour in a thermo-hygrostat (manufactured by TABAI ESPEC CORPORATION, PLATINOUS LUCIFFER PL-2G) in which a temperature was 25° C. and a relative humidity was 90±5% RH. After 1 hour, the water absorbing resin particles or the particulate water absorbing agent in the aluminum cup were/was gently transferred onto a JIS standard sieve (THE IIDA TESTING SIEVE: 80 mm in internal diameter) having a mesh opening size of 2000 μm (JIS 8.6 mesh), and was classified for 5 seconds at room temperature (between 20° C. and 25° C.) with a relative humidity of 50% RH, with use of a Ro-Tap sieve shaker (manufactured by iida-seisakusho Japan Corporation., Sieve shaker type ES-65; Rotation speed: 230 rpm, Impact: 130 rpm). The weight (W9 [g]) of water absorbing resin particles or particulate water absorbing agent remaining on the JIS standard sieve and the weight (W10 [g]) of water absorbing resin particles or particulate water absorbing agent having passed through the JIS standard sieve were measured, and the fluidity after moisture absorption (blocking rate after moisture absorption) was calculated according to the following equation. Note that the smaller value of the fluidity after moisture absorption means more excellent fluidity after moisture absorption.

$$\text{Blocking rate after moisture absorption}[wt \%]=\{W10/(W9+W10)\}\times100 \quad \text{[Math. 5]}$$

[Evaluation Method 8] Dusting Rate

A paint shaker test (PS) same as in the evaluation method 6 was carried out except that the shaking was carried out for 60 minutes. In this way, damage was caused to a particulate water absorbing agent.

The percentage of particles generated during the paint shaker test, which particles have a particle size of not more than 105 μm, was evaluated as the dusting rate. That is, the lower the dusting rate is, the more excellent is the stability to shock of the water absorbing agent.

Dusting rate[wt %]={Amount of particles of not more than 150 μm in diameter after PS}−{Amount of particles of not more than 150 μm in diameter before PS} [Math. 6]

[Evaluation Method 9] Evaluation of Stirring Torque

The "evaluation of stirring torque" according to the present invention is evaluation of load applied on a mixer when water or an aqueous dispersion of a metallic soap is added to a water absorbing resin.

Specifically, 50 g of a water absorbing resin was poured into a 600 mL Pack Ace container, and thereafter the container was placed in a HAAKE torque rheometer having four stirring blades. A predetermined amount of water or an aqueous dispersion of a metallic soap was added and mixed over about 10 seconds with stirring at 128 rpm, and the stirring torque during this operation was outputted to a recorder. After the water or the aqueous dispersion of the metallic soap was added, the stirring torque was read at intervals of 2 seconds for 30 seconds. In this way, load applied on the mixer was evaluated.

[Evaluation Method 10] Solid Content

The solid content was calculated using the moisture content found in the evaluation method 5, according to the following equation.

Solid content[wt %]=100−Moisture content [Math. 7]

[Evaluation Method 11] Extractable Content (Ext)

184.3 g of a 0.90 wt % solution of sodium chloride was measured and poured into a 250 mL plastic container with a lid. To this solution, 1.00 g of a particulate water absorbing agent was added, and the mixture was stirred for 16 hours, thereby extractable content in the particulate water absorbing agent was extracted. A liquid thus extracted was filtered with use of a piece of filter paper (manufactured by Advantec Toyo Kaisha, Ltd.; Product name: JIS P3801, No. 2; thickness: 0.26 mm; diameter of retained particles: 5 μm) to obtain filtrate. 50.0 g of the filtrate thus obtained was used as a liquid for measurements.

The liquid for measurements was titrated with a 0.1N NaOH solution until pH 10 was reached, and was then titrated with a 0.1N HCl solution until pH 2.7 was reached. In this way, titers ([NaOH] mL and [HCl] mL) were measured. Further, the same operations were carried out with respect to a 0.90 wt % solution of sodium chloride alone. In this way, blank titers ([bNaOH] mL and [bHCl] mL) were measured.

The Ext (extractable content) was calculated from the titers obtained by the above operations and the average molecular weight of monomers, according to the following equation 8. It should be noted that, in a case where the average molecular weight of monomers was unknown, the average molecular weight of monomers was calculated from a degree of neutralization calculated according to the following equation 9.

Ext(wt %)=0.1×(Average molecular weight of monomer)×184.3×100×([HCl]−[bHCl]) [Math. 8]

Degree of neutralization[mol %]={1−([NaOH]−[bHaOH])/([HCl]−[bHCl])}×100

[Evaluation Method 12] Rate of Water Absorption (Vortex)

Measurement was carried out in accordance with JIS K7224-1996. Note, however, that the temperature of a test liquid (a 0.9 wt % solution of sodium chloride) was controlled to 30±1° C., and a stirrer chip used was 40 mm in length.

[Evaluation Method 13] VDAUP (Vertical Diffusion Absorbency Under Pressure)

The vertical diffusion absorbency under pressure (VDAUP) [g] was calculated in the same manner as in the AAP, except that the load applied on the water absorbing resin was 4.83 kPa, the weight of the water absorbing resin was 10.000 g, and the calculation was carried out according to the following equation.

VDAUP[g]=W5−W4 [Math. 10]

[Evaluation Method 14] Residual Monomer Content

The filtrate obtained in the [Evaluation method 11] was analyzed by liquid chromatography using a UV detector. In this way, residual monomer content (weight ppm relative to water absorbing resin) in the water absorbing resin was measured.

[Evaluation Method 15] Evaluation of Performance of Absorbent Core 1

For the purpose of evaluating performance of an absorbent core made from the water absorbing resin (or particulate water absorbing agent, described later), the absorbent core was produced and Re-Wet was evaluated.

(Method of Producing Absorbent Core for Evaluation)

2 parts by mass of a water absorbing resin (or particulate water absorbing agent, described later) and 2 parts by mass of fractured wood pulp were dry-blended with use of a mixer. Next, a mixture thus obtained was spread on a 400-mesh wire screen (having a mesh opening size of 38 μm), and was molded into a web 90 mm in diameter. Further, the web was pressed at a pressure of 196.14 kPa (2 [kgf/cm$^2$]) for 1 minute. In this way, an absorbent core for evaluation having a basis weight of about 0.06 [g/cm$^2$] was obtained.

(Method of Evaluating Re-Wet)

The absorbent core for evaluation was placed on the bottom of a SUS dish 90 mm in internal diameter, and a piece of nonwoven fabric 90 mm in diameter was placed on the absorbent core. Subsequently, a piston and a weight were placed on the fabric, which piston and weight have been controlled so that a load of 4.8 kPa was evenly applied on the absorbent core. The piston and the weight used here had a hole for liquid injection at their center. The hole was 5 mm in diameter. Next, 25 ml of physiological saline solution (0.90 wt % solution of sodium chloride) was poured into the center of the absorbent core for evaluation, and allowed to be absorbed into the absorbent core. After 30 minutes, another 25 ml of physiological saline solution (0.90 wt % solution of sodium chloride) was poured into the center of the absorbent core for evaluation, and was allowed to be absorbed into the absorbent core for 30 minutes. After 30 minutes, the piston and the weight, which had been controlled so that a load of 4.8 kPa was evenly applied on the absorbent core, were removed. Then, 30 pieces of filter paper (manufactured by Toyo Roshi Kaisha, Ltd., No. 2) each having an external diameter of 90 mm, the total weight (W11 [g]) of which was measured in advance, were quickly placed on the absorbent core for evaluation. Further, a piston and a weight (external diameter: 90 mm, total weight of the piston and the weight: 20 kg) were quickly placed on the filter paper, which piston and weight had been controlled so that load was evenly applied on the nonwoven fabric and the filter paper. The load was applied for 5 minutes to allow squeezed-out liquid to be absorbed into the filter paper. After that, the weight (W12 [g]) of the 30 pieces of filter paper was measured, and the Re-Wet after 10 minutes (ten-minute Re-Wet) was calculated according to the following equation.

Ten-minute Re-Wet[g]=W12−W11 [Math. 11]

[Evaluation Method 16] Evaluation of Performance of Absorbent Core 2

(Method of Evaluating Rate of Absorption (Core Acquisition) and Re-Wet of Absorbent Core)

An absorbent core to be evaluated was produced in the following manner. That is, first, 50 parts by weight of an absorbing agent (or water absorbing resin) and 50 parts by weight of fractured wood pulp were moistened with use of an ultrasonic humidifier for 10 seconds, and thereafter were mixed together with use of a mixer. Next, a mixture thus obtained was placed on a 400-mesh wire screen (having a mesh opening size of 38 µm), and was air-felted to be molded into a web having a size of 120 mm×400 mm. The web was pressed at a pressure of 2 kg/cm² (196.14 kPa) for 1 minute. In this way, an absorbent core having a basis weight of 0.047 g/cm² was obtained.

Meanwhile, a solution containing 1.9 wt % of urea, 0.8 wt % of NaCl, 0.1 wt % of $CaCl_2$, and 0.1 wt % of $MgSO_4$ (the rest is water) was prepared. That is, artificial urine was prepared.

A load of 50 g/cm² (4.9 kPa) was applied evenly on the entire absorbent core, and a cylinder which is 30 mm in diameter and 120 mm in height was pressed against the center of the absorbent core so as to stand vertically. Next, 50 g of artificial urine having a temperature of 25° C. was quickly (at one go) poured into the cylinder. A time from when the artificial urine started being poured to when the entire artificial urine was absorbed into the absorbent core was measured. The time thus measured serves as the first rate of absorption (seconds). After that, with use of the absorbent core used in the above measurement, the same measurements were carried out twice at an interval of 50 minutes to measure the second rate of absorption (seconds) and the third rate of absorption (seconds). 30 minutes after the third artificial urine was poured, the load was removed from the absorbing article, a paper towel (manufactured by: Oji Paper Co., Ltd., Kitchen Towel Extra Dry, a stack of 30 pieces each having a size of 120 mm×450 mm) was placed on the absorbing article, and a load of 50 g/cm² (4.9 kPa) was placed thereon and allowed to stand for 1 minute. A change in weight of the paper towel was measured, thereby the amount of liquid absorbed into the paper towel was found. The amount thus found was used as the Re-Wet (g).

(Method of Evaluating Blendability with Pulp)

To a mixer containing 50 parts by weight of pulp, 50 parts by weight of a water absorbing resin (or water absorbing agent) is added while being moistened with use of an ultrasonic humidifier. After all of the water absorbing resin (or the water absorbing agent) is added, the mixture is stirred for another 1 minute. The blendability of the water absorbing agent (or the water absorbing resin) with pulp during this process was evaluated as follows.

Very Good: Blendability is good (no water absorbing agent was separated from pulp)
Good: Some water absorbing agent was separated from pulp
Poor: A large amount of water absorbing agent was separated from pulp
Very Poor Aggregates of water absorbing agent were present

[How Examples are Related to Water Absorbing Agents and Production Methods of the Present Invention]

The following Examples 1-7, Examples 8-14 and [Table 1] to [Table 4] are specific examples of the water absorbing agent production methods 1 and 2 of the present invention, i.e., specific examples of obtaining the first to third (and further the fourth) water absorbing agents of the present invention by the water absorbing agent production methods 1 and 2.

The following Examples 15-23 and [Table 5] to [Table 7] are specific examples of the water absorbing agent production methods 1 and 2 of the present invention, i.e., specific examples of obtaining the first to third (and further the fourth) water absorbing agents of the present invention by the water absorbing agent production methods 1 and 2.

As will be described, the first to fourth water absorbing agents can be obtained by for example the production methods 1 to 3. Note, however, that methods to obtain the first to fourth water absorbing agents are not limited to the production methods 1 to 3 described earlier. That is, the second water absorbing agent can be obtained by for example the water absorbing agent production method 1.

The third water absorbing agent can be obtained by for example the water absorbing agent production method 2. Further, the first and fourth water absorbing agents can be obtained by for example the water absorbing agent production methods 1 to 3.

(Water Absorbing Agent Production Method 1)

A particulate water absorbing agent production method (the water absorbing agent production method 1) of the present invention is characterized in that an aqueous dispersion containing a metallic soap (an organic salt of a polyvalent metal) and a dispersion stabilizer is mixed with a water absorbing resin.

(Water Absorbing Agent Production Method 2)

A particulate water absorbing agent production method (the water absorbing agent production method 2) of the present invention is characterized as (i) including the step of adding a metallic soap (an organic salt of a polyvalent metal) and water to a water absorbing resin and (ii) controlling the moisture content of the water absorbing agent to between 5 wt % and 20 wt %.

(Water Absorbing Agent Production Method 3)

A particulate water absorbing agent production method (the water absorbing agent production method 3) of the present invention is a method of producing a particulate water absorbing agent, the particulate water absorbing agent containing a water absorbing resin as a main component, said method including: surface-treating the water absorbing resin by a surface treatment method including the steps of (a) mixing an acid radical-containing radical-polymerizable monomer(s), a polyvalent metal compound and water with the water absorbing resin and (b) polymerizing the acid radical-containing radical-polymerizable monomer(s).

Production Example 1

2.8 g (0.025 mol % relative to acrylic acid) of polyethyleneglycol diacrylate (the average number of moles of ethylene oxide added is 8) was dissolved in 5500 g of solution of sodium acrylate (concentration of monomers is 35 wt %) having a degree of neutralization of 75 mol % to form a reaction liquid. The reaction liquid was degassed in a nitrogen gas atmosphere for 30 minutes.

Next, the reaction liquid was supplied to a reactor formed by attaching a cover to a double-arm type stainless kneader having a capacity of 10 liters and equipped with two sigma type blades and a jacket, and the headspace in the reactor was replaced with nitrogen while the temperature of the reaction liquid was kept at 30° C. Subsequently, 2.46 g of sodium persulfate and 0.10 g of L-ascorbic acid were separately added to the reaction liquid with stirring. As a result, polymerization started after about 1 minute. Then, a generated hydrous gel crosslinked polymer was polymerized at a temperature between 30° C. and 90° C. while being crushed.

After 60 minutes after the start of polymerization, the hydrous gel crosslinked polymer was taken out.

The hydrous gel crosslinked polymer thus obtained had been crushed and had a particle size of about 5 mm. The hydrous gel crosslinked polymer thus crushed was spread on a 50-mesh metal net (having a mesh opening size of 300 μm), and then hot-air dried at 180° C. for 35 minutes. In this way, a dried polymer was obtained Next, the dried polymer thus obtained was pulverized with use of a roller mill, and was classified with use of JIS standard sieves having respective mesh opening sizes of 850 μm and 150 μm. In this way, a water absorbing resin powder (a) in the form of irregular fragments, which powder has a weight median particle size of 360 μm, was obtained. The water absorbing resin powder (a) had a centrifuge retention capacity (CRC) of 49.0 [g/g] and a solid content of 5.1 wt %.

To 100 parts by weight of the water absorbing resin powder (a) thus obtained, a surface-treatment agent composed of 0.02 parts by weight of diethylene glycol diglycidyl ether, 1.0 parts by weight of propylene glycol and 3 parts by weight of water was evenly mixed. After that, the mixture was subjected to heat treatment at 100° C. for 45 minutes. In this way, surface-crosslinked water absorbing resin particles (a) were obtained.

After the heat treatment, the water absorbing resin particles (a) were disintegrated until the particles pass through the JIS standard sieve having a mesh opening size of 850 μm. Next, the particles were subjected to a paint shaker test. In this way, surface-crosslinked water absorbing resin particles (A) were obtained. The water absorbing resin particles (A) had a centrifuge retention capacity (CRC) of 39.9 [g/g] and a moisture content of 5.2 wt %.

Example 1

A commercially-available aqueous dispersion of calcium stearate (product name: Afco-Disper C; manufactured by ADEKA CHEMICAL SUPPLY CO., LTD.; solid content: 50 wt %; 1 wt % to 2 wt % of polyoxyethylene tridecyl ether is contained) was diluted with water. In this way, an aqueous dispersion of calcium stearate having a solid content of 6 wt % was obtained.

To 100 parts by weight of the water absorbing resin particles (A) obtained in Production Example 1, 5 parts by weight (equivalent to 0.3 parts by weight of calcium stearate and 4.7 parts by weight of water) of the aqueous dispersion of calcium stearate having a solid content of 6 wt % was added with stirring. The mixture was mixed for 1 minute. The stirring torque after 30 seconds from the start of addition was 0.70 [N·m]. FIG. 1 shows how the time from the start of addition is related to the stirring torque.

The mixture thus obtained was hardened at 60° C. for 1 hour to obtain a hardened product. The hardened product contained water absorbing resin particles having a particle size of not less than 850 μm in an amount of 0.1 wt % relative to the total amount of the water absorbing agent. The hardened product was disintegrated until it passed through the JIS standard sieve having a mesh opening size of 850 μm. In this way, a particulate water absorbing agent (1) was obtained.

Example 2

The same operations as in Example 1 were repeated except that 10 parts by weight (equivalent to 0.3 parts by weight of calcium stearate and 9.7 parts by weight of water) of an aqueous dispersion of calcium stearate having a solid content of 3 wt % was added instead of 5 parts by weight of the aqueous dispersion of calcium stearate having a solid content of 6 wt %. In this way, a particulate water absorbing agent (2) was obtained.

The stirring torque after 30 seconds from the start of addition was 0.83 [N·m]. Further, an obtained hardened product contained water absorbing resin particles having a particle size of not less than 850 μm in an amount of 0.1 wt % relative to the total amount of the water absorbing agent.

Production Example 2

To 100 parts by weight of the water absorbing resin powder (a) obtained in Production Example 1, a surface-treatment agent composed of a liquid obtained by mixing 0.015 part by weight of ethylene glycol diglycidyl ether, 1.0 part by weight of propylene glycol and 3.0 parts by weight of water was evenly mixed. After that, the mixture was subjected to heat treatment at 80° C. for 60 minutes. Next, the mixture thus heated was disintegrated until it passed through the JIS standard sieve having a mesh opening size of 850 μm. In this way, surface-crosslinked water absorbing resin particles (B) were obtained. The water absorbing resin particles (B) had a centrifuge retention capacity (CRC) of 43.0 [g/g] and a moisture content of 5.5 wt %.

Example 3

To 100 parts by weight of the water absorbing resin particles (B) obtained in Production Example 2, 15 parts by weight (equivalent to 0.3 parts by weight of calcium stearate and 14.7 parts by weight of water) of an aqueous dispersion of calcium stearate having a solid content of 2 wt %, which was prepared by diluting with water a commercially-available product (product name: Afco-Disper C), was added with stirring. Then, the mixture was mixed for 1 minute. The stirring torque after 30 seconds from the start of addition was 0.93 [N·m]. The mixture thus obtained was hardened at 60° C. for 1 hour to obtain a hardened product. The hardened product contained water absorbing resin particles having a particle size of not less than 850 μm in an amount of 0.4 wt % relative to the total amount of the water absorbing agent. The hardened product was disintegrated until it passed through the JIS standard sieve having a mesh opening size of 850 μm. In this way, a particulate water absorbing agent (3) was obtained.

Example 4

The same operations as in Example 1 were repeated except that 3.3 parts by weight (equivalent to 0.3 parts by weight of calcium stearate and 3.0 parts by weight of water) of an aqueous dispersion of calcium stearate having a solid content of 10 wt % was added instead of 5 parts by weight of the aqueous dispersion of calcium stearate having a solid content of 6 wt %. In this way, a particulate water absorbing agent (4) was obtained.

The stirring torque after 30 seconds from the start of addition was 0.69 [N·m]. Further, an obtained hardened product contained water absorbing resin particles having a particle size of not less than 850 μm in an amount of 0.1 wt % relative to the total amount of the water absorbing agent.

Example 5

The same operations as in Example 1 were repeated except that 10 parts by weight (equivalent to 0.1 parts by weight of calcium stearate and 9.9 parts by weight of water) of an aqueous dispersion of calcium stearate having a solid content of 1 wt % was added instead of 5 parts by weight of the aqueous dispersion of calcium stearate having a solid content of 6 wt %. In this way, a particulate water absorbing agent (5) was obtained.

The stirring torque after 30 seconds from the start of addition was 1.22 [N·m]. Further, an obtained hardened product contained water absorbing resin particles having a particle size of not less than 850 μm in an amount of 0.3 wt % relative to the total amount of the water absorbing agent.

Example 6

100 parts by weight of the water absorbing resin particles (A) obtained in Production Example 1 and 0.5 parts by weight of zinc stearate powder (manufactured by KANTO CHEMICAL CO., INC) were placed in a Loedige mixer (manufactured by Loedige, type: M5R), and were stirred at 330 rpm for 15 seconds to obtain a mixture of the water absorbing resin particles and zinc stearate. To the mixture, 5 parts by weight of water was added with stirring, and the mixture was mixed for 1 minute. Here, the stirring torque after 30 seconds from the start of addition was 0.47 [N·m]. The mixture thus obtained was hardened at 60° C. for 1 hour to obtain a hardened product. The hardened product contained water absorbing resin particles having a particle size of not less than 850 μm in an amount of 0.4 wt % relative to the total amount of the water absorbing agent. The hardened product thus obtained was disintegrated until it passed through the JIS standard sieve having a mesh opening size of 850 μm. In this way, a particulate water absorbing agent (6) was obtained.

Example 7

The same operations as in Example 6 were repeated except that the amount of zinc stearate powder was changed to 0.1 part by weight and the amount of water was changed to 10 parts by weight. In this way, a particulate water absorbing agent (7) was obtained.

The stirring torque after 30 seconds from the start of addition was 0.87 [N·m]. Further, an obtained hardened product contained water absorbing resin particles having a particle size of not less than 850 μm in an amount of 4.7 wt % relative to the total amount of the water absorbing agent.

Comparative Example 1

To 100 parts by weight of the water absorbing resin particles (A) obtained in Production Example 1, 5.0 parts by weight of water was added with stirring. As a result, a stirrer stopped due to overload after 14 seconds from the start of addition. FIG. 1 shows how the time from the start of addition is related to the stirring torque.

Next, a piece of the mixture thus obtained was hardened at 60° C. for 1 hour. In this way, a comparative water absorbing agent (1) was obtained. The hardened product thus obtained contained water absorbing resin particles having a particle size of not less than 850 μm in an amount of 9.1 wt % relative to the total amount of the water absorbing agent.

Comparative Example 2

The same operations as in Example 6 were repeated except that, in accordance with Patent Literature 19, 0.5 part by weight of hydrophilic silicon dioxide (product name: Aerosil 200, manufactured by Nippon Aerosil Co., Ltd.) was used instead of zinc stearate. In this way, a comparative water absorbing agent (2) was obtained.

The stirring torque after 30 seconds from the start of addition was 0.56 [N·m]. Further, an obtained hardened product contained water absorbing resin particles having a particle size of not less than 850 μm in an amount of 20.4 wt % relative to the total amount of the water absorbing agent.

Comparative Example 3

The same operations as in Example 6 were repeated except that, in accordance with Patent Literature 18, 5.0 parts by weight of a 10 wt % solution of sodium alum (manufactured by Wako Pure Chemical Industries, Ltd.) was used instead of zinc stearate. In this way, a comparative water absorbing agent (3) was obtained.

The stirrer stopped due to overload after 24 seconds from the start of addition of the solution of sodium alum. Further, an obtained hardened product contained water absorbing resin particles having a particle size of not less than 850 μm in an amount of 56.9 wt % relative to the total amount of the water absorbing agent.

Comparative Example 4

The same operations as in Example 1 were repeated except that 30 parts by weight (equivalent to 0.1 part by weight of calcium stearate and 29.9 parts by weight of water) of an aqueous dispersion of calcium stearate having a solid content of 0.33 wt % was added instead of 5 parts by weight of the aqueous dispersion of calcium stearate having a solid content of 6 wt %. In this way, a comparative water absorbing agent (4) was obtained.

The stirrer stopped due to overload after 20 seconds from the start of addition of the aqueous dispersion of calcium stearate. Further, an obtained hardened product contained water absorbing resin particles having a particle size of not less than 850 μm in an amount of 25.1 wt % relative to the total amount of the water absorbing agent.

Production Example 3

To 100 parts by weight of the water absorbing resin powder (a) obtained in Production Example 1, a surface-treatment agent composed of a liquid obtained by mixing 0.03 parts by weight of ethylene glycol diglycidyl ether, 0.5 parts by weight of propylene glycol, 0.3 parts by weight of 1,4-butanediol, and 3 parts by weight of water was evenly mixed. After that, the mixture was subjected to heat treatment at 200° C. for 40 minutes. Next, the particles were subjected to the paint shaker test. In this way, surface-crosslinked water absorbing resin particles (C) were obtained. The water absorbing resin particles (C) had a centrifuge retention capacity (CRC) of 37.4 [g/g] and a moisture content of 2.4 wt %.

Example 8

The same operations as in Example 1 were repeated except that the water absorbing resin particles (C) were used instead of the water absorbing resin particles (A). In this way, a particulate water absorbing agent (8) was obtained.

The stirring torque after 30 seconds from the start of addition was 0.65 [N·m]. Further, an obtained hardened product contained water absorbing resin particles having a particle size of not less than 850 μm in an amount of 0.1 wt % relative to the total amount of the water absorbing agent.

Example 9

The same operations as in Example 1 were repeated except that an aqueous dispersion of zinc stearate (prepared by diluting with water a commercially-available product (product name: Afco-Disper ZD; manufactured by ADEKA CHEMICAL SUPPLY CO., LTD.; solid content: 42.5 wt %; a surfactant is contained)) was used instead of the aqueous dispersion of calcium stearate. In this way, a particulate water absorbing agent (9) was obtained.

The stirring torque after 30 seconds from the start of addition was 0.60 [N·m]. Further, an obtained hardened product contained water absorbing resin particles having a particle size of not less than 850 μm in an amount of 0.3 wt % relative to the total amount of the water absorbing agent.

Example 10

20 parts by weight of zinc stearate (manufactured by KANTO CHEMICAL CO., INC.), 8 parts by weight of sodium polyoxyethylene laurylether sulfate (product name: EMAL 20C, manufactured by Kao Corporation, solid content: 25 wt %) and 72 parts by weight of water were mixed to obtain an aqueous dispersion of zinc stearate (a).

To 100 parts by weight of the water absorbing resin particles (C) obtained in Production Example 3, 5.0 parts by weight (equivalent to 1.0 parts by weight of zinc stearate, 3.6 parts by weight of water, and 0.4 parts by weight of dispersion stabilizer) of the aqueous dispersion of zinc stearate (a) was added with stirring. Then, the mixture was mixed for 1 minute. The stirring torque after 30 seconds from the start of addition was 0.42 [N·m]. The mixture thus obtained was hardened at 60° C. for 1 hour to obtain a hardened product. The hardened product contained water absorbing resin particles having a particle size of not less than 850 μm in an amount of 0.1 wt % relative to the total amount of the water absorbing agent. The hardened product thus obtained was disintegrated until it passed through the JIS standard sieve having a mesh opening size of 850 μm. In this way, a particulate water absorbing agent (10) was obtained.

Example 11

20 parts by weight of zinc stearate (manufactured by KANTO CHEMICAL CO., INC.), 2 parts by weight of sodium dodecyl sulfate (manufactured by KANTO CHEMICAL CO., INC.) and 78 parts by weight of water were mixed to obtain an aqueous dispersion of zinc stearate (b).

The same operations as in Example 10 were repeated except that the aqueous dispersion of zinc stearate (b) was used as an aqueous dispersion of zinc stearate. In this way, a particulate water absorbing agent (11) was obtained.

The amount of zinc stearate added was substantially 1.0 parts by weight, the amount of water added was substantially 3.9 parts by weight, and the amount of dispersion stabilizer added was substantially 0.1 part by weight, relative to 100 parts by weight of the water absorbing resin particles (C). The stirring torque after 30 seconds from the start of addition was 0.45 [N·m]. Further, an obtained hardened product contained water absorbing resin particles having a particle size of not less than 850 μm in an amount of 0.1 wt % relative to the total amount of the water absorbing agent.

Comparative Example 5

To 100 parts by weight of the water absorbing resin particles (C) obtained in Production Example 3, 1.4 parts by weight of water was added with stirring. Then, the mixture was mixed for 1 minute. The stirring torque after 30 seconds from the start of addition was 0.84 [N·m]. The mixture thus obtained was hardened at 60° C. for 1 hour to obtain a hardened product. The hardened obtained contained water absorbing resin particles having a particle size of not less than 850 μm in an amount of 2.3 wt % relative to the total amount of the water absorbing agent.

After that, the hardened product was disintegrated until it passed through the JIS standard sieve having a mesh opening size of 850 μm. Next, a disintegrated product thus obtained and 0.6 parts by weight of zinc stearate (manufactured by KANTO CHEMICAL CO., INC.) were placed in a Loedige mixer (manufactured by Loedige, Type: M5R), and were stirred at 330 rpm for 15 seconds. In this way, a comparative water absorbing agent (5) was obtained.

Table 1 shows physical properties of the water absorbing resin particles (A) to (C), the particulate water absorbing agents (1) to (11) and the comparative water absorbing agents (1) to (5). That is, Table 1 shows a comparison of the water absorbing agent production methods 1 and 2 of the present invention and the obtained first to fourth water absorbing agents with conventional techniques.

TABLE 1

|  | Type of additive | Concentration of water dispersion [wt %] | Amount of additive (Solid content) [wt %] | Amount of water added [wt %] | Evaluation of stirring torque [N·m] | Percentage of particles 1) [wt %] | CRC [g/g] |
| --- | --- | --- | --- | --- | --- | --- | --- |
| Water absorbing resin particles (A) |  |  |  |  |  |  | 39.9 |
| Water absorbing resin particles (B) |  |  |  |  |  |  | 43.0 |
| Water absorbing resin particles (C) |  |  |  |  |  |  | 37.4 |
| Particulate water absorbing agent (1) | StCa sus. | 6.0 | 0.3 | 4.7 | 0.7 | 0.1 | 38.1 |
| Particulate water absorbing agent (2) | StCa sus. | 3.0 | 0.3 | 9.7 | 0.83 | 0.1 | 36.5 |
| Particulate water absorbing agent (3) | StCa sus. | 2.0 | 0.3 | 14.7 | 0.93 | 0.4 | 36.8 |
| Particulate water absorbing agent (4) | StCa sus. | 10.0 | 0.3 | 3 | 0.69 | 0.1 | 38.8 |
| Particulate water absorbing agent (5) | StCa sus. | 1.0 | 0.1 | 9.9 | 1.22 | 0.3 | 36.4 |
| Particulate water absorbing agent (6) | StZn |  | 0.5 | 5 | 0.47 | 0.4 | 38.1 |

TABLE 1-continued

| | | | | | | | |
|---|---|---|---|---|---|---|---|
| Particulate water absorbing agent (7) | StZn | | 0.1 | 10 | 0.87 | 4.7 | 36.4 |
| Particulate water absorbing agent (8) | StCa sus. | 6.0 | 0.3 | 4.7 | 0.65 | 0.1 | 36.5 |
| Particulate water absorbing agent (9) | StCa sus. | 6.0 | 0.3 | 4.7 | 0.6 | 0.3 | 36.5 |
| Particulate water absorbing agent (10) | StCa sus. | 20 | 1.0 | 3.6 | 0.42 | 0.1 | 36.9 |
| Particulate water absorbing agent (11) | StCa sus. | 20 | 1.0 | 3.9 | 0.45 | 0.1 | 36.9 |
| Comparative water absorbing agent (1) | | | | 5 | Stopped after 14 seconds | 9.1 | 38.1 |
| Comparative water absorbing agent (2) | Silica | | 0.5 | 5 | 0.56 | 20.4 | 38.0 |
| Comparative water absorbing agent (3) | Sodium alum | | 0.5 | 4.5 | Stopped after 24 seconds | 56.9 | 37.7 |
| Comparative water absorbing agent (4) | StCa sus. | 0.33 | 0.1 | 29.9 | Stopped after 20 seconds | 25.1 | 32.3 |
| Comparative water absorbing agent (5) | StZn | | 0.6 | 1.4 | 0.84 | 2.3 | 38.0 |

| | AAP 4.83 kPa [g/g] | VDAUP [g/g] | Moisture content [wt %] | Blocking Rate after moisture absorption | Dusting rate [wt %] | AAP + 1.8CRC |
|---|---|---|---|---|---|---|
| Water absorbing resin particles (A) | 14.0 | | 5.2 | 100 | 2.4 | |
| Water absorbing resin particles (B) | 13.8 | | 5.5 | 100 | 2.3 | |
| Water absorbing resin particles (C) | 16.6 | | 2.4 | 100 | 3.0 | |
| Particulate water absorbing agent (1) | 13.1 | | 9.7 | 0 | 0.7 | 81.8 |
| Particulate water absorbing agent (2) | 12.6 | | 13.6 | 0 | 0.4 | 78.3 |
| Particulate water absorbing agent (3) | 12.1 | | 17.2 | 0 | 0.4 | 78.3 |
| Particulate water absorbing agent (4) | 13.4 | | 8.1 | 0 | 0.7 | 83.2 |
| Particulate water absorbing agent (5) | 12.6 | | 13.7 | 5 | 0.4 | 78.1 |
| Particulate water absorbing agent (6) | 13.1 | | 9.8 | 0 | 0.6 | 81.7 |
| Particulate water absorbing agent (7) | 12.5 | | 13.8 | 6 | 0.4 | 78.1 |
| Particulate water absorbing agent (8) | 15.8 | 22.4 | 7.2 | 0 | 0.8 | 81.6 |
| Particulate water absorbing agent (9) | 15.8 | 22.3 | 7.3 | 0 | 0.8 | 81.5 |
| Particulate water absorbing agent (10) | 16.0 | 23.1 | 6.2 | 0 | 0.7 | 82.4 |
| Particulate water absorbing agent (11) | 15.9 | 23.0 | 6.3 | 0 | 0.7 | 82.4 |
| Comparative water absorbing agent (1) | 13.5 | | 9.8 | 100 | 2.9 | 82.1 |
| Comparative water absorbing agent (2) | 8.0 | | 9.7 | 0 | 1.2 | 76.4 |
| Comparative water absorbing agent (3) | 8.5 | | 9.2 | 0 | 1.6 | 76.4 |
| Comparative water absorbing agent (4) | 11.1 | | 25.9 | 20 | 0.2 | 69.2 |
| Comparative water absorbing agent (5) | 16.4 | | 3.6 | 0 | 1.3 | 84.7 |

1) Percentage of particles not less than 850 μm in diameter in a hardened product It should be noted that the abbreviations in Table 1 represent the following terms:
StCa sus.: Aqueous dispersion (suspension) of calcium stearate
StZn: Zinc stearate powder
StZn sus.: Aqueous dispersion (suspension) of zinc stearate Example 12

The water absorbing resin particles (A) obtained in Production Example 1 were continuously supplied at 120 [kg/h] to a continuous-type high-speed stirring mixer (Turbulizer, manufactured by Hosokawa Micron Corporation) while the aqueous dispersion of calcium stearate having a solid content of 6 wt % (used in Example 1) was sprayed at 6.0 [kg/h] (the amount of calcium stearate added was substantially 0.3 wt % and the amount of water added was substantially 4.7 wt %, relative to the amount of the water absorbing resin particles (A)). In this way, the water absorbing resin particles (A) and the aqueous dispersion of calcium stearate having a solid content of 6 wt % were continuously mixed.

The continuous mixing was carried out for 10 hours. As a result, load applied on a motor of a mixer apparatus remained constant even after 10 hours, and no adhesion was found inside the mixer. Further, the mixture thus obtained was continuously heated and hardened with use of a paddle dryer at 60° C. for 30 minutes. Furthermore, classification was carried out with use of a sieving apparatus to separate particles that passed through a 850-μm sieve. Particles that did not pass through the 850-μm sieve were pulverized again with use of a roller granulator, and thereafter were mixed with the particles that passed through the 850-μm sieve. In this way, a sized particulate water absorbing agent (12) consisting only of the particles having passed through the 850-μm sieve was obtained. As to the sieving apparatus and the roller granulator, load applied on their motor was constant even after 10 hours.

Examples 13

The same operations as in Example 12 were repeated except that the aqueous dispersion of calcium stearate having a solid content of 2 wt % (used in Example 3) was added at 18.0 [kg/h] (the amount of calcium stearate added was substantially 0.3 wt % and the amount of water added was substantially 14.7 wt %, relative to the amount of the water absorbing resin particles (A)) instead of the aqueous dispersion of calcium stearate having a solid content of 6 wt %. In this way, a particulate water absorbing agent (13) was obtained.

Even after 10 hours of continuous mixing, load applied on the motor of the mixer remained constant and no adhesion was found inside the mixer. Further, also as to the sieving apparatus and the roller granulator, load applied on their motor was constant even after 10 hours.

Example 14

The water absorbing resin particles (A) obtained in Production Example 1 and zinc stearate (manufactured by KANTO CHEMICAL CO., INC.) were poured into a continuous Loedige mixer (manufactured by Loedige) at 120 [kg/h] and 0.6 [kg/h], respectively, and were continuously stirred and mixed to obtain a mixture. After that, the mixture was continuously poured into a continuous-type high-speed stirring mixer (Turbulizer, manufactured by Hosokawa Micron Corporation), and water was sprayed at 6.0 [kg/h] (the amount of water added was substantially 5.0 wt % relative to the amount of the water absorbing resin particles (A)). Then, the mixture was continuously mixed. Subsequent operations were the same as those as in Example 12. In this way, a particulate water absorbing agent (14) was obtained.

Even after 10 hours of continuous mixing, load applied on the motor of the mixer remained constant and no adhesion was found inside the mixer. Further, also as to the sieving apparatus and the roller granulator, load applied on their motor was constant even after 10 hours.

Comparative Example 5

The same operations as in Example 12 were repeated except that water was added at 6.0 [kg/h] (the amount of water added was substantially 5.0 wt % relative to the amount of the water absorbing resin particles (A)) instead of the aqueous dispersion of calcium stearate having a solid content of 6 wt %. As a result, load applied on the motor of the mixing apparatus started to gradually increase soon after the start of addition of water. After 5 minutes, the motor stopped due to overload. After the stirring mixer was stopped, inside of the mixer was checked. It was found that a lot of moistened products were adhered around a stirring rod of the mixing apparatus, and a space between stirring blades and a body was partly blocked with the water absorbing resin.

Comparative Example 6

The same operations as in Example 14 were repeated except that hydrophilic silicon dioxide (product name: Aerosil 200, manufactured by Nippon Aerosil Co., Ltd.) was added at 0.6 [kg/h] (the amount of hydrophilic silicon dioxide added was substantially 0.5 wt % relative to the amount of the water absorbing resin particles (A)) instead of zinc stearate. In this way, a comparative water absorbing agent (6) was obtained.

Even after 6 hours of continuous mixing, load applied on the motor of the mixer remained constant and no adhesion was found inside the stirring mixer. However, as to the sieving apparatus and the roller granulator, load applied on their motor gradually increased, and then the roller granulator stopped due to overload after 6 hours. This was because there were a lot of water absorbing resin particles having a particle size of not less than 850 μm.

Comparative Example 7

The same operations as in Example 12 were repeated except that the 10 wt % solution of sodium alum used in Comparative Example 3 was added at 6.0 [kg/h] instead of the aqueous dispersion of calcium stearate having a solid content of 6 wt %. As a result, load applied on the motor of the mixer started to gradually increase soon after the start of addition of water. After 21 minutes, the motor stopped due to overload. After the stirring mixer was stopped, inside of the mixing apparatus was checked. It was found that a lot of moistened products were adhered around the stirring rod of the mixing apparatus, and a space between the stirring blades and body was partly blocked with the water absorbing resin.

Table 2 shows physical properties of the particulate water absorbing agents (12) to (14) and the comparative water absorbing agent (6). It should be noted in Table 2 that the "AAP+1.8 CRC" means that "Absorbency against pressure (AAP 4.83 kPa)+1.8×Absorbency without pressure (CRC)". The same applies to the other tables shown as below.

That is, Table 2 shows a comparison of the first water absorbing agent of the present invention obtained by the water absorbing agent production methods 1 and 2 of the present invention with a conventional technique.

TABLE 2

|  | CRC [g/g] | AAP 4.83 kPa [g/g] | Moisture content [wt %] | AAP + 1.8CRC |
|---|---|---|---|---|
| Water absorbing agent (12) | 38.3 | 13.4 | 9.2 | 82 |
| Water absorbing agent (13) | 36.1 | 12.6 | 15.3 | 78 |
| Water absorbing agent (14) | 38.2 | 13.3 | 9.3 | 82 |
| Comparative water absorbing agent (6) | 38.0 | 8.0 | 9.0 | 76 |

(Regarding Table 1, Table 2 and FIG. 1)

As is clear from Table 1, each of the particulate water absorbing agents (1) to (11) obtained by adding a metallic soap and water to the water absorbing resin (A) or (B) and controlling the moisture content to between 5 wt % and 15 wt % is excellent in absorbency against pressure (AAP), fluidity after moisture absorption (blocking rate after moisture absorption) and dusting rate (stability to shock). Since each of the particulate water absorbing agents (1) to (11) applies only a light load on a mixing apparatus when water is added (i.e., the stirring torque is low), formation of coarse particles having a particle size of not less than 850 μm is suppressed when water is added.

Further, the following is clear from Example 1 and Comparative Examples 1, 3 and 4 shown in FIG. 1. That is, according to Example 1, the load applied on the mixing apparatus when water is added changes little over time. In contrast, according to Comparative Examples 1, 3 and 4, the load applied on the mixing apparatus dramatically increases over time.

Further, as shown in Examples 12 to 14, according to the water absorbing agents (12) to (14) which apply only a light load on the mixing apparatus when water is added (i.e., the stirring torque is low) and which produce few coarse particles having a particle size of not less than 850 μm when water is added, it is possible to stably and efficiently produce a water absorbing agent even after many hours of continuous operation.

As to the comparative water absorbing agent (2) which was obtained by mixing hydrophilic silicon dioxide with the water absorbing resin particles (A) in accordance with Patent Literature 17, the comparative water absorbing agent (2) shows a significant decrease (by about 4 g/g to 5 g/g) in absorbency against pressure (AAP). Further, in order to obtain a water absorbing agent having a target particle size, it is necessary to pulverize coarse particles having a particle size of not less than 850 μm, which coarse particles are generated in a large amount when water is added (refer to Comparative Example 6). Since this applies a heavy load on a pulverizer, the comparative water absorbing agent (2) is not suited for continuous operation. Further, the comparative water absorbing agent (2) shows a further decrease in absorbency against pressure (AAP) due to pulverization.

The same applies to the comparative water absorbing agent (3), which was obtained by mixing a solution of sodium alum with the water absorbing resin particles (A) in accordance with Patent Literature 16. The comparative water absorbing agent (3) shows a significant decrease (by about 4 g/g to 5 g/g) in absorbency against pressure (AAP), and is not suited for continuous operation due to a heavy load applied to the mixer when mixing is carried out.

It was confirmed that, unlike Patent Literatures 14 to 17, the present invention provides a water absorbing agent which (i) has high absorbency against pressure (AAP), (ii) is excellent in stability to shock, (iii) applies only a light load on a mixing apparatus and is capable of being sized under a light load when water is added, and (iv) is capable of being produced continuously over a long period of time.

(Result of Evaluation of Absorbent Core)

Each of the water absorbing agents obtained in Examples 1, 3, and 10 and Comparative Examples 1, 4 and 5 was evaluated for blendability with pulp, Re-Wet of an absorbent core, and rate of absorption (core acquisition) of the absorbent core. The evaluation and measurement were carried out in accordance with Evaluation of performance of absorbent core 2 described in Evaluation method 16. The results are shown in Table 3.

TABLE 3

Evaluation of absorbent core (diaper) including water absorbing agent of the present invention

| | Absorbing agent | | | Absorbent core | | | | |
|---|---|---|---|---|---|---|---|---|
| | CRC | AAP 4.83 kPa | Moisture content | Blendability | Re-Wet | Rate of absorption [Seconds] | | |
| | [g/g] | [g/g] | [wt %] | with pulp | [g] | First time | Second time | Third time |
| Particulate water absorbing agent (1) | 38.1 | 13.1 | 9.7 | Very Good | 5 | 32 | 54 | 80 |
| Particulate water absorbing agent (3) | 36.8 | 12.1 | 17.2 | Very Good | 8 | 33 | 72 | 96 |
| Particulate water absorbing agent (10) | 36.9 | 16.0 | 6.2 | Good | 6 | 33 | 66 | 88 |
| Comparative water absorbing agent (1) | 38.1 | 13.5 | 9.8 | Very poor | 12 | 37 | 138 | 165 |
| Comparative water absorbing agent (4) | 32.3 | 11.1 | 25.9 | Good | 11 | 36 | 112 | 129 |
| Comparative water absorbing agent (5) | 38.0 | 16.4 | 3.6 | Poor | 10 | 36 | 107 | 121 |

As is clear from the results shown in Table 3, it was confirmed that satisfying the requirements of claim 1, like a water absorbing agent such as those obtained in Examples 1, 3 and 10 does, makes it possible to improve stability to shock and blendability with pulp and thus possible to improve Re-Wet and rate of absorption of an absorbent core, as compared to the water absorbing agents obtained in Comparative Examples 1, 4 and 5.

Production Example 4

To a 1-liter polypropylene container which is 80 mm in internal diameter and is enclosed by styrene foam (heat insulator), a solution (A) prepared by mixing 257.6 g of acrylic acid, 0.84 g (0.045 mol % relative to acrylic acid) of polyethyleneglycol diacrylate (molecular weight: 523) and 1.58 g of a 1.0 mass % solution of pentasodium diethylenetriamine pentaacetic acid, and a solution (B) prepared by mixing 215.2 g of a 48.5 mass % solution of sodium hydroxide and 210.4 g of ion exchanged water having been controlled to have a temperature of 50° C. were poured. Here, the solution (B) was quickly added to the solution (A) with stirring with a magnetic stirrer in an open system so that the solution (A) and the solution (B) were mixed. In this way, a monomer solution, whose temperature had risen to about 102° C. due to heat of neutralization and heat of dissolution, was obtained.

After the temperature of the monomer solution thus obtained decreased to 95° C., 14.30 g of a 3 mass % solution of sodium persulfate was added, and the mixture was stirred for several seconds. After that, in an open system, the mixture was poured into a tray-shaped stainless container which has a bottom surface of about 250 mm×250 mm, inside surface of which is coated with Teflon (registered trademark) and whose surface temperature had been raised to 100° C. with use of a hot plate (NEO HOTPLATE H1-1000, manufactured by IUCHI SEIEIDO CO., LTD.). The tray-shaped stainless container had a bottom surface of 250 mm×250 mm, a top surface of 640 mm×640 mm and a height of 50 mm, had a trapezoidal cross-sectional surface when cut in the middle, and had the top surface opened.

Upon pouring of the monomer solution into the tray, polymerization of the monomer solution started. The polymerization proceeded while the monomer solution was generating water vapor and expanding and foaming in all directions, and thereafter the monomer solution was shrunk to a size of somewhat larger than the bottom surface. Such expansion and shrinkage completed within about 1 minute. After being allowed to remain in a polymerization container for 4 minutes, a hydrous polymer was taken out.

The hydrous polymer thus obtained was crushed with use of a meat chopper having a dice diameter of 9.5 mm (ROYAL MEAT CHOPPER VR400K, manufactured by Iiduka Kogyo Co., Ltd.) to obtain a crushed hydrous polymer. The crushing was carried out by providing a gel at about 340 g/min and, in the meantime, adding deionized water at 48 g/min. The crushed gel contained a non-volatile matter in an amount between 50 mass % and 55 mass %.

A crushed hydrous gel crosslinked polymer thus obtained was spread on a 50-mesh metal net, and hot-air dried at 180° C. for 35 minutes to obtain a dried polymer. The dried polymer was pulverized with use of a roller mill, and was further classified with use of the JIS standard sieves having respective mesh opening sizes of 850 μm and 150 μm. In this way, a water absorbing resin (D) in the form of irregular fragments, which has a weight median particle size of 360 μm, was obtained. The water absorbing resin (D) had a centrifuge retention capacity (CRC) of 36.0 [g/g] and an extractable content of 12.0 mass %.

To 100 parts by mass of the water absorbing resin (D) thus obtained, a surface-treatment agent composed of a liquid obtained by mixing 0.4 parts by mass of 1,4-butanediol, 0.6 parts by mass of propylene glycol and 3.0 parts by mass of pure water was evenly mixed. After that, the mixture was subjected to heat treatment at 200° C. for 30 minutes. Further, particles of the mixture were disintegrated until they passed through the JIS standard sieve having a mesh opening size of 850 μm. Next, the particles were subjected to the paint shaker test 1. In this way, surface-crosslinked water absorbing resin particles (D) were obtained.

Example 15

20 parts by mass of zinc stearate (manufactured by KANTO CHEMICAL CO., INC), 8 parts by mass of sodium polyoxyethylene laurylether sulfate (product name: EMAL 20C, manufactured by Kao Corporation, solid content is 25 mass %) and 72 parts by mass of water were mixed to obtain an aqueous dispersion of zinc stearate.

To 100 parts by mass of the water absorbing resin particles (D), 5.0 parts by mass of the aqueous dispersion of zinc stearate was evenly mixed with stirring, and the mixture was dried at 60° C. for 1 hour to obtain a dried product. The dried product was disintegrated until it passed through the JIS standard sieve having a mesh opening size of 850 μm. In this way, a water absorbing agent (15) was obtained.

Example 16

20 parts by mass of zinc stearate (manufactured by KANTO CHEMICAL CO., INC.), 2 parts by mass of sodium dodecyl sulfate (manufactured by KANTO CHEMICAL CO., INC.) and 78 parts by mass of water were mixed to obtain an aqueous dispersion of zinc stearate.

To 100 parts by mass of the water absorbing resin particles (D), 5.0 parts by mass of the aqueous dispersion of zinc stearate was evenly mixed with stirring, and the mixture was dried at 60° C. for 1 hour to obtain a dried product. The dried product was disintegrated until it passed through the JIS standard sieve having a mesh opening size of 850 μm. In this way, a water absorbing agent (16) was obtained.

Comparative Example 8

In accordance with Patent Literature 9, 100 parts by mass of the water absorbing resin particles (D) and 0.6 parts by mass of zinc stearate (manufactured by KANTO CHEMICAL CO., INC.) were placed in a Loedige mixer (manufactured by Loedige, type: M5R), and were stirred at 330 rpm for 15 seconds. In this way, a comparative water absorbing agent (8) was obtained.

Comparative Example 9

In accordance with Patent Literature 9, 100 parts by mass of the water absorbing resin particles (D) and 1.0 parts by mass of zinc stearate (manufactured by KANTO CHEMICAL CO., INC.) were placed in a Loedige mixer (manufactured by Loedige, type: M5R), and were stirred at 330 rpm for 15 seconds. In this way, a comparative water absorbing agent (9) was obtained.

Comparative Example 10

To 100 parts by mass of the water absorbing resin particles (D), 1.4 parts by mass of water was evenly mixed with stirring, and the mixture was dried at 60° C. for 1 hour to obtain a dried product. The dried product was disintegrated until it passed through the JIS standard sieve having a mesh opening size of 850 μm to obtain a disintegrated product. Next, the disintegrated product and 0.6 pats by mass of zinc stearate (manufactured by KANTO CHEMICAL CO., INC.) were placed in a Loedige mixer (manufactured by Loedige, type: M5R), and were stirred at 330 rpm for 15 seconds. In this way, a comparative water absorbing agent (10) was obtained.

Comparative Example 11

In accordance with Patent Literatures 1 to 4, the same operations as in Comparative Example 8 were repeated except that 0.5 parts by mass of hydrophilic silicon dioxide (product name: Aerosil 200, manufactured by Nippon Aerosil Co., Ltd.) was used instead of zinc stearate. In this way, a comparative water absorbing agent (11) was obtained.

Comparative Example 12

In accordance with Patent Literatures 1 to 4, the same operations as in Comparative Example 8 were repeated except that 1.0 parts by mass of hydrophilic silicon dioxide (product name: Aerosil 200, manufactured by Nippon Aerosil Co., Ltd.) was used instead of zinc stearate. In this way, a comparative water absorbing agent (12) was obtained.

Table 4 shows physical properties of the water absorbing resin particle (D), the water absorbing agents (15) and (16) and the comparative water absorbing agents (8) to (12). That is, Table 4 shows a comparison of the water absorbing agent production methods 1 and of the present invention and the obtained first to fourth water absorbing agents of the present invention with conventional techniques.

(Water Absorbing Agent Production Method 3)

A particulate water absorbing agent production method (the water absorbing agent production method 3) of the present invention is a method of producing a particulate water absorbing agent, the particulate water absorbing agent containing a water absorbing resin as a main component, said method including: surface-treating the water absorbing resin by a surface treatment method including the steps of (a) mixing an acid radical-containing radical-polymerizable

TABLE 4

|  | CRC [g/g] | AAP 4.83 kPa [g/g] | VDAUP [g/g] | Blocking rate after moisture absorption [wt %] | D50 [μm] | σζ | 150-pass amount [wt %] | Moisture content [wt %] | Vortex [sec] |
|---|---|---|---|---|---|---|---|---|---|
| Water absorbing resin particles (D) | 31.9 | 26.4 |  | 100 | 359 | 0.37 | 2.04 | 2.4 | 58.1 |
| Water absorbing agent (15) | 30.4 | 23.9 | 30.2 | 0 | 360 | 0.37 | 2.18 | 6.2 | 60.8 |
| Water absorbing agent (16) | 30.5 | 24 | 29.9 | 0 | 363 | 0.37 | 2.2 | 6.3 | 60.4 |
| Comparative water absorbing agent (8) | 31.7 | 25.1 |  | 0.2 | 362 | 0.37 | 1.99 | 2.4 | 68.2 |
| Comparative water absorbing agent (9) | 31.8 | 25.4 |  | 0 | 358 | 0.37 | 1.91 | 2.4 | 68.2 |
| Comparative water absorbing agent (10) | 31.7 | 25.2 |  | 0 | 380 | 0.34 | 0.81 | 3.6 | 67.3 |
| Comparative water absorbing agent (11) | 32.4 | 22.6 |  |  | 381 | 0.34 | 0.93 | 2.4 |  |
| Comparative water absorbing agent (12) | 32.2 | 21.8 |  |  | 405 | 0.35 | 0.97 | 2.4 |  |

(Closing)

As is clear from Table 4, each of the water absorbing agents (15) and (16) obtained by mixing an aqueous dispersion containing a metallic soap and a dispersion stabilizer to the water absorbing resin particles (D) is excellent in absorbency against pressure (AAP) and fluidity after moisture absorption (blocking resistance) and has excellent rate of water absorption (Vortex).

As to the comparative water absorbing agents (8) and (9) obtained by mixing a metallic soap to the water absorbing resin particles (D) in accordance with Patent Literature 9, each of the comparative water absorbing agents (8) and (9) shows a significant decrease in rate of water absorption (Vortex) (i.e., it took about 10 more seconds). The same applies to the comparative water absorbing agent (10) obtained by mixing each separately a metallic soap and water. The comparative water absorbing agent (10) shows a significant decrease in rate of water absorption (Vortex) (i.e., it took about 10 more seconds).

Further, as to the comparative water absorbing agents (11) and (12) obtained by mixing hydrophilic silicon dioxide with the water absorbing resin particles (D) in accordance with Patent Literatures 1 to 4, each of the comparative water absorbing agents (11) and (12) shows a significant decrease (by about 4 g/g to 5 g/g) in absorbency against pressure (AAP). Unlike Patent Literatures 14 to 16, the present invention is capable of providing a water absorbing agent which is high in absorbency against pressure (AAP) and rate of water absorption (Vortex) and contains a predetermined amount of water (preferably between 0.01 wt % and not more than 20 wt %).

The foregoing description discussed Examples 1 to 16 of the water absorbing agent production methods 1 and 2. On the other hand, the following description discusses Examples 17 to 22 which are specific examples of the water absorbing agent production method 3.

monomer(s), a polyvalent metal compound and water with the water absorbing resin and (b) polymerizing the acid radical-containing radical-polymerizable monomer(s).

Production Example 5

A solution of acrylic acid monomers (concentration of monomers: 38 wt %, degree of neutralization: 75 mol %) composed of sodium acrylate, acrylic acid and water was prepared and placed in a kneader equipped with two sigma type blades. Then, polyethyleneglycol diacrylate (the average number of ethylene oxide units: n=9) serving as an internal crosslinking agent was dissolved so that the amount of the polyethyleneglycol diacrylate was 0.023 mol % relative to the amount of the monomers.

Next, a nitrogen gas was blown into the solution to reduce oxygen concentration in the solution and to replace the headspace in a reaction container by nitrogen. Subsequently, 0.05 mol % (relative to the monomers) of sodium persulfate and 0.0006 mol % (relative to the monomers) of L-ascorbic acid, which serve as polymerization initiators, were added while the two sigma type blades were rotated. The mixture was stirred and polymerized in the kneader. After 40 minutes, a hydrous gel polymer having a median particle size of 2 mm was obtained.

The hydrous gel polymer thus obtained was dried for 45 minutes in a hot air dryer in which a temperature was set to 170° C. After that, the dried polymer was pulverized with use of a roller mill pulverizer. The dried polymer was classified with use of a sieve having a mesh opening size of 500 μm so that particles having a particle size of more than 500 μm were removed, and classified with use of a sieve having a mesh opening size of 125 μm so that particles having a particle size of less than 125 μm were removed. In this way, a water absorbing resin (E) serving as a base polymer was obtained.

Table 5 shows particle size distribution of the water absorbing resin (E) serving as a base polymer thus obtained. Table 6 shows the results of evaluations of the water absorbing resin (E) serving as a base polymer.

Production Example 6

The same operations as in Production Example 5 were repeated except that the step of removing small particles by classification was omitted. In this way, a water absorbing resin (F) serving as a base polymer was obtained.

Table 5 shows particle size distribution of the water absorbing resin (F) serving as a base polymer thus obtained. Table 7 shows the results of evaluations of the water absorbing resin (F) serving as a base polymer thus obtained.

Production Example 7

The same operations as in Production Example 5 were repeated except that the sieve for removing large particles was changed to a sieve having a mesh opening size of 850 µm and the sieve for removing small particles was changed to a sieve having a mesh opening size of 180 µm. In this way, a water absorbing resin (G) serving as a base polymer was obtained. Table 5 shows particle size distribution of the water absorbing resin (G) serving as a base polymer thus obtained. Table 7 shows the results of evaluations of the water absorbing resin (G) serving as a base polymer thus obtained. Note that all the particles were in the form of irregular fragments.

TABLE 5

|  | Production Example | | |
|---|---|---|---|
|  | 5 | 6 | 7 |
| Water absorbing resin | E | F | G |
| D50 (µm) | 250 | 178 | 474 |
| Particle size distribution |  |  |  |
| 850 µm or greater (wt %) | 0 | 0 | 0 |
| 850 µm to 500 µm (wt %) | 0 | 0 | 45.1 |
| 500 µm to 300 µm (wt %) | 33.3 | 23.5 | 40.0 |
| 300 µm to 150 µm (wt %) | 55.4 | 40.2 | 14.2 |
| 150 µm or less (wt %) | 11.3 | 36.3 | 0.7 |
| Total (wt %) | 100 | 100 | 100 |

It should be noted in Table 5 that the (A µm or greater) means a particulate water absorbing resin remaining on a sieve having a mesh opening size of A µm after the classification operation. The (B µm or less) means a particulate water absorbing resin having passed through a sieve having a mesh opening size of B µm. The (C µm to D µm) means a particulate water absorbing resin which has passed through a sieve having a mesh opening size of C µm but remained on a sieve having a mesh opening size of D µm.

Example 17

30 g of the water absorbing resin (E) serving as a base polymer was added in a 500 mL separable flask made of quartz. Then, a solution prepared in advance by mixing 0.033 g of glycerin dimethacrylate (manufactured by SHIN-NAKAMURA CHEMICAL CO., LTD., NK Ester 701), 0.90 g of acrylic acid, 2.10 g of water, 0.003 g of IRGACURE (registered trademark) 2959 (manufactured by Ciba Specialty Chemicals Inc.) and 0.09 g of aluminum sulfate 14-18 hydrate was added with stirring by use of a stirring blade. After 10 minutes of stirring, the mixture was irradiated with UV light at room temperature for a total of 1.5 minutes at 65 [mW/cm$^2$] (measured in a position, on a wall of the separable flask made of quartz, which is nearest to a UV lamp, with use of a uviometer UIT-150 and a light receiving part UVD-S254 manufactured by USHIO INC.), with use of a UV light irradiator (UV-152/1MNSC3-AA06, manufactured by USHIO INC.) to which a metal halide lamp (UVL-1500M2-N1, manufactured by USHIO INC.) was attached. In this way, a surface-crosslinked water absorbing resin serving as a particulate water absorbing agent (17) was obtained.

Table 6 shows the results of evaluations of the particulate water absorbing agent (17) thus obtained. It should be noted that, in the present example and subsequent Examples and Comparative Examples, the evaluation of an absorbent core was carried out in accordance with Evaluation of performance of absorbent core 1 of Evaluation method 15.

Example 18

The same operations as in Example 17 were repeated except that the amount of acrylic acid used was 1.20 g. In this way, a surface-crosslinked water absorbing resin serving as a particulate water absorbing agent (18) was obtained. Table 6 shows the results of evaluations of the particulate water absorbing agent (18) thus obtained. Table 8 shows the results obtained by evaluating performance of an absorbent core including the particulate water absorbing agent (18).

Example 19

The same operations as in Example 17 were repeated except that the amount of acrylic acid used was 1.50 g. In this way, a surface-crosslinked water absorbing resin serving as a particulate water absorbing agent (19) was obtained. Table 6 shows the results of evaluations of the particulate water absorbing agent (19) thus obtained.

Example 20

The same operations as in Example 17 were repeated except that the amount of aluminum sulfate 14-18 hydrate used was 0.15 g. In this way, a surface-crosslinked water absorbing resin serving as a particulate water absorbing agent (20) was obtained. Table 6 shows the results of evaluations of the particulate water absorbing agent (20) thus obtained.

Example 21

The same operations as in Example 18 were repeated except that 30 g of the water absorbing resin (F) serving as a base polymer was used and the amount of aluminum sulfate 14-18 hydrate used was 0.30 g. In this way, a surface-crosslinked water absorbing resin serving as a particulate water absorbing agent (21) was obtained. Table 7 shows the results of evaluations of the particulate water absorbing agent (21) thus obtained.

Example 22

The same operations as in Example 21 were repeated except that the amount of water in the solution was 4.20 g. In this way, a surface-crosslinked water absorbing resin serving as a particulate water absorbing agent (22) was obtained.

Table 7 shows the results of evaluations of the particulate water absorbing agent (22) thus obtained.

Example 23

The same operations as in Example 18 were repeated except that 30 g of the water absorbing resin (C) serving as a base polymer was used. In this way, a surface-crosslinked water absorbing resin serving as a particulate water absorbing agent (23) was obtained. Table 7 shows the results of evaluations of the particulate water absorbing agent (23) thus obtained.

Comparative Example 13

The same operations as in Example 17 were repeated except that the aluminum sulfate 14-18 hydrate was not contained in the solution. In this way, a comparative water absorbing agent (13) was obtained. Table 6 shows the results of evaluations of the comparative water absorbing agent (13) thus obtained.

Comparative Example 14

The same operations as in Example 17 were repeated except that polyethyleneglycol monomethyl ether (manufactured by Aldrich, $CH_3(OCH_2CH_2)_nOH$, the number average molecular weight Mn: 2000) was used in stead of the aluminum sulfate 14-18 hydrate in the solution. In this way, a comparative water absorbing agent (14) was obtained. Table 6 shows the results of evaluations of the comparative water absorbing agent (14) thus obtained.

Comparative Example 15

The same operations as in Comparative Example 14 were repeated except that the amount of acrylic acid used was 1.20 g. In this way, a comparative water absorbing agent (15) was obtained. Table 6 shows the results of evaluations of the comparative water absorbing agent (15) thus obtained. Table 8 shows the results obtained by evaluating performance of an absorbent core including the comparative water absorbing agent (15).

Comparative Example 16

To 30 g of the comparative water absorbing agent (13) obtained in Comparative Example 13, 0.39 g of a solution obtained by mixing a 50 wt % solution of aluminum sulfate 14-18 hydrate and a 60 wt % solution of sodium lactate in proportions of 10:3 by weight was added. In this way, a comparative water absorbing agent (16) was obtained. Table 6 shows the results of evaluations of the comparative water absorbing agent (16) thus obtained.

Comparative Example 17

The same operations as in Comparative Example 15 were repeated except that 30 g of the water absorbing resin (F) was used as a base polymer. In this way, a comparative water absorbing agent (17) was obtained. Table 7 shows the results of evaluations of the comparative water absorbing agent (17) thus obtained.

Comparative Example 18

The same operations as in Comparative Example 17 were repeated except that the amount of water in the solution was 4.20 g. In this way, a comparative water absorbing agent (18) was obtained. Table 7 shows the results of evaluations of the comparative water absorbing agent (18) thus obtained.

Note that all the particles of the water absorbing agents shown in Tables 6 to 8 were in the form of irregular fragments.

TABLE 6

| | | Treatment agent | | | | | | |
|---|---|---|---|---|---|---|---|---|
| | Water absorbing resin | 701 [wt %] | AA [wt %] | W [wt %] | IRGA-CURE [wt %] | ASH [wt %] | PEGOMe [wt %] | Moisture content [wt %] |
| Production Example 5 | Water absorbing resin (E) | | | | | | | 6.9 |
| Example 17 | Particulate water absorbing agent (17) | 0.11 | 3 | 7 | 0.01 | 0.3 | | 12.4 |
| Example 18 | Particulate water absorbing agent (18) | 0.11 | 4 | 7 | 0.01 | 0.3 | | 11.0 |
| Example 19 | Particulate water absorbing agent (19) | 0.11 | 5 | 7 | 0.01 | 0.3 | | 11.8 |
| Example 20 | Particulate water absorbing agent (20) | 0.11 | 3 | 7 | 0.01 | 0.5 | | 13.1 |
| Comparative Example 13 | Comparative water absorbing agent (13) | 0.11 | 3 | 7 | 0.01 | | | 12.8 |
| Comparative Example 14 | Comparative water absorbing agent (14) | 0.11 | 3 | 7 | 0.01 | | 0.01 | 12.8 |
| Comparative Example 15 | Comparative water absorbing agent (15) | 0.11 | 4 | 7 | 0.01 | | 0.01 | 12.3 |
| Comparative Example 16 | Comparative water absorbing agent (16) | 0.11 | 3 | 7 | 0.01 | | | 13.1 |

| | Physical properties | | | | | |
|---|---|---|---|---|---|---|
| | CRC [g/g] | AAP 2.07 kPa [g/g] | AAP 4.83 kPa [g/g] | VDAUP [g] | Res. M [ppm] | AAP + 1.8CRC |
| Production Example 5 | 54.7 | | | | | |

TABLE 6-continued

|  | | | | | | |
|---|---|---|---|---|---|---|
| Example 17 | 35.5 | 29.0 | 17.0 | | | 81 |
| Example 18 | 34.0 | 30.7 | 21.1 | 33.4 | 312 | 82 |
| Example 19 | 32.6 | 30.9 | 22.5 | | | 81 |
| Example 20 | 35.8 | 28.8 | 16.9 | | | 81 |
| Comparative Example 13 | 36.0 | 26.9 | 12.0 | | | |
| Comparative Example 14 | 37.0 | 25.7 | 10.0 | | | |
| Comparative Example 15 | 35.2 | 27.9 | 12.9 | 12.1 | 2378 | |
| Comparative Example 16 | 35.2 | 25.2 | 10.8 | | | |

TABLE 7

First or fourth water absorbing agent obtained by water absorbing agent production method 3

| | | Treatment agent | | | | | | |
|---|---|---|---|---|---|---|---|---|
| | Water absorbing resin | 701 [wt %] | AA [wt %] | W [wt %] | IRGA-CURE [wt %] | ASH [wt %] | PEGOMe [wt %] | Moisture content [wt %] |
| Production Example 6 | Water absorbing resin (F) | | | | | | | 7.2 |
| Production Example 7 | Water absorbing resin (G) | | | | | | | 5.3 |
| Example 21 | Particulate water absorbing agent (21) | 0.11 | 4 | 7 | 0.01 | 1 | | 14.2 |
| Example 22 | Particulate water absorbing agent (22) | 0.11 | 4 | 14 | 0.01 | 1 | | 19.1 |
| Example 23 | Particulate water absorbing agent (23) | 0.11 | 4 | 7 | 0.01 | 0.3 | | 12.4 |
| Comparative Example 17 | Comparative water absorbing agent (17) | 0.11 | 4 | 7 | 0.01 | | 0.01 | 11.3 |
| Comparative Example 18 | Comparative water absorbing agent (18) | 0.11 | 4 | 14 | 0.01 | | 0.01 | 14.1 |

| | Physical properties | | | | | |
|---|---|---|---|---|---|---|
| | CRC [g/g] | AAP 2.07 kPa [g/g] | AAP 4.83 kPa [g/g] | VDAUP [g] | Res. M [ppm] | AAP + 1.8CRC |
| Production Example 6 | 50.7 | | | | | |
| Production Example 7 | 52.6 | | | | | |
| Example 21 | 35.3 | 16.5 | | | | |
| Example 22 | 29.5 | 22.0 | | | | |
| Example 23 | 33.0 | 29.0 | 22.0 | 52.4 | 332 | 81 |
| Comparative Example 17 | 44.2 | 6.5 | | | | |
| Comparative Example 18 | 41.6 | 8.3 | | | | |

It should be noted that the abbreviations in Tables 6 and 7 represent the following terms:

701: NK Ester 701 (manufactured by SHIN-NAKAMURA CHEMICAL CO., LTD., glycerin dimethacrylate)

AA: Acrylic acid

W: Pure water

IRGACURE: IRGACURE 2959 (manufactured by Ciba Specialty Chemicals Inc.)

ASH: Aluminum sulfate 14-18 hydrate

PEGOMe: Polyethyleneglycol monomethyl ether (manufactured by Aldrich, $CH_3(OCH_2CH_2)_nOH$, the number average molecular weight Mn: 2000)

Res.M: Residual monomer content

TABLE 8

Evaluation of absorbent core (diaper) including first or fourth water absorbing agent obtained by water absorbing agent production method 3

| | Water absorbing agent | Re-Wet (g) |
|---|---|---|
| Example 18 | Particulate water absorbing agent (18) | 5 |
| Comparative Example (15) | Comparative water absorbing agent (15) | 11 |

INDUSTRIAL APPLICABILITY

A water absorbing agent production method in accordance with the present invention is suitable for producing a water absorbing agent containing as a main component a water absorbing resin having excellent physical properties. A water absorbing agent of the present invention is suitable for use in sanitary materials such as disposable diapers, sanitary napkins and incontinence pads.

REFERENCE SIGNS LIST

100 Supporting cylinder made of plastic
101 400-mesh metal net made of stainless steel
102 Swollen gel
103 Piston
104 Load (weight)
105 Petri dish
106 Glass filter
107 Filter paper
108 0.90 wt % solution of sodium chloride

The invention claimed is:

1. A particulate water absorbing agent comprising:
a water absorbing resin as a main component, wherein the water absorbing resin comprises a polyacrylic acid (salt) crosslinked polymer;
a polyvalent metal, wherein the polyvalent metal is a metallic soap and/or a water-soluble polyvalent metal salt; and
a dispersion stabilizer;
wherein said particulate water absorbing agent has:
(1) a polyvalent metal cation in an amount between 0.001 wt % and 5 wt % relative to the amount of the particulate water absorbing agent;
(2) an absorbency without pressure (CRC) of not less than 28 (g/g) and not more than 60 (g/g), and an absorbency against pressure (AAP 4.83 kPa) of not less than 10 (g/g) and not more than 40 (g/g);
(3) the absorbency against pressure and the absorbency without pressure satisfy the inequality: 77≤Absorbency against pressure (AAP 4.83 kPa)+1.8×Absorbency without pressure (CRC)≤100;
(4) a moisture content between 5 wt % and 20 wt %; and
(5) a dusting rate between 0 wt % and 0.8 wt %.

2. The particulate water absorbing agent according to claim 1, wherein a vertical diffusion absorbency under pressure (VDAUP) is not less than 15 g.

3. The particulate water absorbing agent according to claim 1, which satisfies any one of the following (A) through (C):

(A) the particulate water absorbing agent is obtained by mixing an aqueous dispersion containing a metallic soap and a dispersion stabilizer with the water absorbing resin;
(B) the particulate water absorbing agent is obtained by a method including the steps of adding a metallic soap and water to the water absorbing resin and controlling a moisture content of the water absorbing agent to between 5 wt % and 20 wt %; and
(C) the particulate water absorbing agent is obtained by carrying out a surface treatment method for water absorbing resin, the method including the steps of (i) mixing an acid radical-containing radical-polymerizable monomer, a polyvalent metal compound and water with the water absorbing resin which is a polyacrylic acid (salt) crosslinked polymer and (ii) polymerizing the acid radical-containing radical-polymerizable monomer.

4. The particulate water absorbing agent according to claim 1, wherein:
the metallic soap is contained in an amount between 0.001 and 5 parts by weight relative to 100 parts by weight of the water absorbing resin; and
the dispersion stabilizer is contained in an amount between 0.0001 and 1 part by weight relative to 100 parts by weight of the water absorbing resin.

5. The particulate water absorbing agent according to claim 1, wherein the dispersion stabilizer is a surfactant.

6. The particulate water absorbing agent according to claim 1, wherein the water absorbing resin is a surface-crosslinked water absorbing resin.

7. The particulate water absorbing agent according to claim 1, wherein a blocking rate after moisture absorption is between 0 wt % and 10 wt %.

8. The particulate water absorbing agent according to claim 1, which is obtained by granulating water absorbing resin particles.

9. An absorbing article comprising a particulate water absorbing agent recited in claim 1.

10. The particulate water absorbing agent according to claim 1, wherein:
the absorbency against pressure and the absorbency without pressure satisfy the inequality: 77≤Absorbency against pressure (AAP 4.83 kPa)+1.8×Absorbency without pressure (CRC)≤90.

* * * * *